US012458577B2

(12) United States Patent
Einziger et al.

(10) Patent No.: US 12,458,577 B2
(45) **Date of Patent: *Nov. 4, 2025**

(54) **PHOTOPROTECTIVE COMPOSITIONS CONTAINING *MALASSEZIA*-DERIVED COMPOUNDS AND/OR CHEMICAL ANALOGS THEREOF**

(71) Applicant: Versicolor Technologies, LLC, Santa Monica, CA (US)

(72) Inventors: Michael Einziger, Malibu, CA (US); Ann Marie Simpson, Malibu, CA (US)

(73) Assignee: VERSICOLOR TECHNOLOGIES, LLC, Santa Monica, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 17/556,778

(22) Filed: Dec. 20, 2021

(65) Prior Publication Data

US 2022/0110848 A1 Apr. 14, 2022

Related U.S. Application Data

(63) Continuation of application No. 16/549,106, filed on Aug. 23, 2019, now Pat. No. 11,202,748.

(60) Provisional application No. 62/722,412, filed on Aug. 24, 2018, provisional application No. 62/742,657, filed on Oct. 8, 2018.

(51) Int. Cl.

| | |
|---|---|
| ***A61K 8/49*** | (2006.01) |
| ***A61K 31/404*** | (2006.01) |
| ***A61K 31/407*** | (2006.01) |
| ***A61K 31/519*** | (2006.01) |
| ***A61P 17/16*** | (2006.01) |
| ***A61Q 17/04*** | (2006.01) |
| ***A61Q 19/02*** | (2006.01) |

(52) U.S. Cl.

CPC ............ *A61K 8/492* (2013.01); *A61K 8/4926* (2013.01); *A61K 8/4953* (2013.01); *A61K 8/4973* (2013.01); *A61K 31/404* (2013.01); *A61K 31/407* (2013.01); *A61K 31/519* (2013.01); *A61P 17/16* (2018.01); *A61Q 17/04* (2013.01); *A61Q 19/02* (2013.01)

(58) Field of Classification Search

CPC .... C07D 209/12; C07D 487/04; A61K 31/59; A61K 31/404; A61K 31/407

See application file for complete search history.

(56) References Cited

U.S. PATENT DOCUMENTS

| | | | | |
|---|---|---|---|---|
| 9,969,686 | B2 | 5/2018 | Tang et al. | |
| 10,131,631 | B2 * | 11/2018 | Einziger | C07D 487/04 |
| 10,730,833 | B2 | 8/2020 | Tang et al. | |
| 11,104,644 | B2 * | 8/2021 | Einziger | A61K 8/492 |
| 11,202,748 | B2 * | 12/2021 | Einziger | A61K 31/519 |
| 11,220,491 | B2 * | 1/2022 | Einziger | A61P 17/00 |
| 11,987,555 | B2 * | 5/2024 | Einziger | A61Q 19/02 |
| 2009/0263339 | A1 | 10/2009 | Kyono et al. | |
| 2010/0324109 | A1 | 12/2010 | Saurat | |
| 2016/0039754 | A1 | 2/2016 | Tang et al. | |
| 2017/0260133 | A1 | 9/2017 | Einziger et al. | |
| 2018/0222861 | A1 | 8/2018 | Tang et al. | |
| 2018/0370913 | A1 | 12/2018 | Einziger et al. | |
| 2019/0337927 | A1 | 11/2019 | Einziger et al. | |
| 2019/0345140 | A1 | 11/2019 | Einziger et al. | |
| 2022/0106297 | A1 | 4/2022 | Einziger et al. | |
| 2022/0110848 | A1 | 4/2022 | Einziger et al. | |

FOREIGN PATENT DOCUMENTS

| | | | |
|---|---|---|---|
| CN | 106916171 | A | 7/2017 |
| KR | 20160128764 | A | 11/2016 |
| WO | 0236561 | A1 | 5/2002 |
| WO | 2014143125 | A1 | 9/2014 |
| WO | WO 2017/156424 | A1 | 9/2017 |
| WO | 2019200232 | A1 | 10/2019 |
| WO | 2020041663 | A1 | 2/2020 |

OTHER PUBLICATIONS

Adachi et al., "Indirubin and Indigo are Potent Aryl Hydrocarbon Receptor Ligands Present in Human Urine," The Journal of Biological Chemistry, vol. 276, No. 34, p. 31475-31478 (Aug. 24, 2001).

Berridge et al., "The Biochemical and Cellular Basis of Cell Proliferation Assays That Use Tetrazolium Salts", Biochemica, vol. 4 pp. 4-19 (1996).

Bergman, J. et al., "Synthesis of indolocarbazole quinones; potent aryl hydrocarbon receptor ligands," Tetrahedron 58 (2002) 1443-1452.

Black, et al. "Athymic Nude Mice and Human Skin Grafting", In: Maibach, et al. (eds.), Models in Dermatology vol. 1., Karger, Basel, pp. 228-239, (1985).

(Continued)

*Primary Examiner* — Kevin E Weddington

(74) *Attorney, Agent, or Firm* — Mintz Levin Cohn Ferris Glovsky and Popeo, P.C.

(57) ABSTRACT

The present invention relates to compounds, compositions, and methods for modulating skin pigmentation and treating or preventing UV-induced skin damage, erythema, aging of the skin, sunburn, and hyperpigmentation in a subject. The compounds, compositions, and methods of the present invention generally involve *Malassezia*-derived compounds, including malassezin and indirubin, and/or chemical analogs thereof. Other applications of the compounds and compositions disclosed herein include, but are not limited to, improving hyperpigmentation caused by a hyperpigmentation disorder, inducing melanocyte apoptosis, and modulating arylhydrocarbon receptor (AhR) activity, melanogenesis, melanin production, melanosome biogenesis, melanosome transfer, melanocyte activity, and melanin concentration.

22 Claims, 23 Drawing Sheets
(9 of 23 Drawing Sheet(s) Filed in Color)

(56) References Cited

OTHER PUBLICATIONS

Costin, et al., "Optimized in vitro pigmentation screening assay using a reconstructed three dimensional human skin model", Rom. J. Biochem, vol. 50 No. 1, pp. 15-27, (2013).
Crisan et al., "QSAR Study and Molecular Docking on Indirubin Inhibitors of Glycogen Synthase Kinase-3," Cent. Eur. J. Chem., 11 (1), pp. 63-77 (2013).
Donato, et al., "A Microassay for Measuring Cytochrome P450IA1 and P450IIB1 Activities in Intact Human and Rat Hepatocytes Cultured on 96-Well Plates", Anal Biochem, vol. 213, No. 1, pp. 29-33, (1993).
Elmore, "Apoptosis: A Review of Programmed Cell Death", Toxicologic Pathology, vol. 35, pp. 495-516, (2007).
English Translation for KR 20160128764 A (2016).
Evdokimov et al., "Isatin derivatives with activity against apoptosis-resistant cancer cells", Bioorganic Medicinal Chemistry Letters, vol. 26, No. 6, pp. 1558-1560, (2016).
Fitzpatrick et al., "The Validity and Practicality of Sun-Reactive Skin Types I Through VI", Arch Dermatol, vol. 124, No. 6, pp. 869-871, (1988).
Gaitanis et al., "Skin Diseases Associated With *Malassezia* Yeasts: Facts and Controversies", Clinics in Dermatology, vol. 31, pp. 455-463, (2013).
Gambichler et al., "Quantification of Ultraviolet Protective Effects of Pityriacitrin in Humans", Archives of Dermatological Research; vol. 299, pp. 517-520, (2007).
Gueho et al., "The Genus *Malassezia* With Description of Four New Species", Antonie Van Leeuwenhoek, vol. 69, pp. 337-355, (1996).
He, Y. et al., "Substrate-Controlled Regioselective Arylations of 2-Indolylmethanols with Indoles: Synthesis of Bis(idolyl)methane and 3,3'-Bisindole Derivatives", The Journal of Organic Chemistry 82 (2017) 2462-2471.
International Search Report and Written Opinion for PCT/US2019/047831, dated Jan. 8, 2020.
Karchner, et al., "Identification and Functional Characterization of Two Highly Divergent Aryl Hydrocarbon Receptors (AHR1 and AHR2) in the Teleost Fundulus heteroclitus", The Journal of Biological Chemistry, vol. 274, No. 47, pp. 33814-33824, (1999).
Kramer et al., "Malassezin, a Novel Agonist of the Aryl Hydrocarbon Receptor from the Yeast *Malassezia furfur*, Induces Apoptosis in Primary Human Melanocytes", Chembiochem, vol. 6, No. 5, pp. 860-865, (2005).
Lee, et al., "Comparison of Gene Expression Profiles Between Keratinocytes, Melanocytes and Fibroblasts", Ann Dermatol, vol. 25, No. 1, pp. 35-45, (2013).
Machowinski et al., "Pityriacitrin—A Potent UV filter Produced by *Malassezia furfur* and its Effect on Human Skin", Mycoses, vol. 49, pp. 388-392, (2006).
Manning, et al., "Maintenance of Skin Xenografts of Widely Divergent Phylogenetic Origin on Congenitally Athymic (Nude) Mice", J Exp Med, vol. 138, pp. 488-494, (1973).
Mayser et al., "Pityriacitrin—An Ultraviolet-Absorbing Indole Alkaloid from the Yeast *Malassezia furfur*", Archives of Dermatological Research, vol. 294, pp. 131-134, (2002).
Mayser et al., "Pityrialactone—A New Fluorochrome from the Tryptophan Metabolism of *Malassezia furfur*", Antonie van Leeuwenhoek; vol. 84, pp. 185-191, (2003).
Nazzaro-Porro, et al., "Identification of Tyrosinase Inhibitors in Cultures of Pityrosporum", The Journal of Investigative Dermatology, vol. 71, pp. 205-208, (1978).
Noakes, "The Aryl Hydrocarbon Receptor: A Review of Its Role in the Physiology and Pathology of the Integument and Its Relationship to the Tryptophan Metabolism", Journal of Tryptophan Research, vol. 8, pp. 17-18, (2015).
Otulakowski et al., "Use of a Human Skin-Grafted Nude Mouse Model for the Evaluation of Topical Retinoic Acid Treatment", J Invest Dermatol, vol. 102, pp. 515-518, (1994).
Park et al., "Inhibitory effect of 2-methyl-naphtho[1,2,3-de]quinolin-8-one on melanosome transport and skin pigmentation", Sci. Rep., vol. 6 No. 29189, Doi: 10.1038/srep29189, (2016).
Pillaiyar, T. et al., "A rapid, efficient and versatile green synthesis of 3,3'-diidolvlmethanes," Arkivoc (2018) Part III, 1-19.
Pillaiyar, T. et al., "Supplementary Material: A rapid, efficient and versatile green synthesis of diindolylmethanes" Arkivoc (2018) Part III, S1-S61.
Plenat et al. "Host-Donor Interactions in Healing of Human Split-Thickness Skin Grafts Onto Nude Mice: In Situ Hybridization, Immunohistochemical and Histochemical Studies", Transplantation, vol. 53, pp. 1002-1010, (1992).
Reed et al., "Long-Term Maintenance of Normal Human Skin on Congenitally Athymic (Nude) Mice", Proc Soc Exp Biol Med, vol. 143, pp. 350-353, (1973).
Scott et al., "The Permeability of Grafted Human Transplant Skin in Athymic Mice", J Pharm Pharmacol, vol. 40, pp. 128-129, (1988).
Song et al., "A Ligand for the Aryl Hydrocarbon Receptor Isolated From Lung", PNAS, vol. 99, No. 23, pp. 14694-14699, (2002).
Taylor et al., "The Taylor Hyperpigmentation Scale: a new visual assessment tool for the evaluation of skin color and pigmentation", Cutis, vol. 76, No. 4, pp. 270-274, (2005).
Wang et al., "Stress-Induced RNASET2 Overexpression Mediates Melanocyte Apoptosis Via the TRAF2 Pathway In Vitro", Cell Death and Disease, 5:e1022, (2014).
Wasmeier, et al. "Melanosomes at a Glance", Journal of Cell Science, vol. 121, pp. 3995-3999, (2008).
Whyte et al., "Ethoxyresorufin-O-deethylase (EROD) Activity in Fish as a Biomarker of Chemical Exposure", Critical Reviews in Toxicology, vol. 30, No. 4, pp. 347-570, (2000).
Wille et al., "Malassezin—A Novel Agonist of the Arylhydrocarbon Receptor From the Yeast *Malassezia furfur*", Bioorganic & Medicinal Chemistry, vol. 9, pp. 955-960, (2001).
Winston-McPherson, et al., "Synthesis and Biological Evaluation of 2,3'-diindolylmethanes as Agonists of Aryl Hydrocarbon Receptor", Bioorganic & Medicinal Chemistry Letters, vol. 24, No. 16, pp. 4023-4025, (2014).
Yamaguchi et al., "Melanocytes and Their Diseases", Cold Spring Harb Perspect Med, vol. 4, a017046, (2014).
Zhang et al., "Environmental adaptability and quorum sensing: Iron uptake regulation during biofilm formation by *Paracoccus dentrificans*", Appl Environ Microbiol, vol. 84, No. 14, pp. e00865-18, (2018).
Zonios et al., "Skin Melanin, Hemoglobin, and Light Scattering Properties can be Quantitatively Assessed In Vivo Using Diffuse Reflectance Spectroscopy", J Invest Dermatol, vol. 117, pp. 1452-1457, (2001).
Tholander et al. (Mar. 19, 1998) "Synthesis of 6-Formylindolo[3,2-b]Carbazole, an Extremely Potent Ligand for the Aryl Hydrogen (Ah) Receptor", Tetrahedron Letters, 39:1619-1622.
Wahlstroem et al. (2004) "Synthesis of 2,3'-Diindolylmethanes and Substituted Indolo[3,2-b]Carbazoles, Synthesis", Synthesis, (8):1187-1197.
Waller et al. (1995) "Three-Dimensional Quantitative Structure-Activity Relationships of Dioxins and Dioxin-like Compounds: Model Validation and Ah Receptor Characterization.", Chemical research in toxicology, 8:847-858.
Zeng et al. (2005) "Novel Method for Synthesis of Unsymmetrical Bis(indolyl)alkanes Catalyzed by Ceric Ammonium Nitrate (CAN) Under Ultrasonic Irradiation", Tetrahedron, 61(43):10235-10241.
Boudreault et al. (Oct. 2010) "Synthesis and characterization of soluble indolo[3,2-b]carbazole derivatives for organic field-effect transistors", Organic Electronics, 11(10):1649-1659.
Colombo et al. (2008) "Three-Component Indium-Mediated Domino Allylation of 1H-Indole-3-carbaldehyde with Electron-Rich (Hetero)arenes: Highly Efficient Access to Variously Functionalized Indolylbutenes", European Journal of Organic Chemistry, (16), 2801-2807.
Liang et al. (Jan. 8, 2015) "A Biomimetic Method to Synthesise Indolo[3,2-a]Carbazoles", Tetrahedron Letters, 56(2): 434-436.
Lin et al. (1998) "Indole-Carbonyl Coupling Reactions Promoted by Samarium Diiodide. Application to the Synthesis of Indole-Fused Compounds", The Journal of Organic Chemistry, 63(9):2909-2917.
Luecke et al. (2010) "The Aryl Hydrocarbon Receptor (AHR), A Novel Regulator of Human Melanogenesis", Pigment Cell Melanoma Research, 23(6):828-833.

(56) References Cited

OTHER PUBLICATIONS

Tholander et al. (1999) "Syntheses of 6, 12-Disubstituted 5,11-Dihydroindolo[3,2-b]Carbazoles, Including 5,11-Dihydroindolo[3,2-b]Carbazole-6,12-Dicarbaldehyde, an Extremely Efficient Ligand for the TCDD (Ah) Receptor", Tetrahedron, 55:12577-12594.
Tholander et al. (1999) "Syntheses of 6-Substituted Indolo[3,2-b]Carbazoles, Including 6-Formylindolo[3,2-b] Carbazole, an Extremely Efficient Ligand for the TCDD (Ah) Receptor", Tetrahedron, 55:6243-6260.
Gibbs et al., "Aminocatalytic Preparation of Bisindolylalkanes", Organic & Biomolecular Chemistry, 2005, 3 (22):4043-4045.
Nguyen et al., "D-Amino Acid Oxidase Generates Agonists of the Aryl Hydrocarbon Receptor from D-Tryptophan", Chemical Research on Toxicology, 2009, 22(12):1897-1904.
Wahlstrom et al., "Synthesis of Metabolites of the Ah Receptor Ligand 6-Formylindolo[3,2-b]carbazole", European Journal of Organic Chemistry, 2004, 2004(12):2593-2602.

* cited by examiner

Fig. 1

| IIVS Test Article Number | Concentration | Sponsor's Designation | pH (Day 0, 2, 4, 6)^ | Mean Tissue Viability (%)[1] | Melanin Concentration (µg/mL) – *from the linear curve* |
|---|---|---|---|---|---|
| | | | | Day 7 | |
| 18AB74 | Neat | 2767-09 84-030118E w/ AB17011 @ 200 ppm | 5.0; 5.0; 5.0; 5.0 | 35.6 | 31.929 |
| 18AB75 | Neat | 2767-07 84-030118C w/ AB17219 @ 200 ppm | 5.0; NCC; 5.0; 5.0 | 54.9 | 31.319 |
| 18AB76 | Neat | 2767-11 84-030118G w/ CV-8685 @ 200 ppm | 5.0; 4.5; 4.5; 4.5 | 30.8 | 33.761 |
| 18AB77 | Neat | 2767-12 84-030118H w/ CV-8687 @ 200 ppm | 5.0; 4.5; 4.5; 4.5 | 67.8 | 36.050 |
| 18AB78 | Neat | 2767-08 84-030118D w/ AB17225 @ 200 ppm | 5.0; 5.0; 5.0; 5.0 | 27.8 | 26.740 |
| 18AB79 | Neat | 2767-10 84-03011D w/ AB17220 @ 200 ppm | 5.0; 5.0; 5.0; 5.0 | 19.1 | 26.587 |
| 18AB80 | Neat | 2767-06 84-030118A w/ BASE @ 200 ppm | 5.0; NCC; 5.0; 5.0 | 71.9 | 37.882 |
| 18AD25 | Neat | 4% Hydroquinone | 3.0; 3.0; 3.0; 4.0 | 34.8 | 408.476 |
| 18AD41 | Neat | BRIGHTENING TREATMENT | 5.0; 5.0; 5.0; 5.0 | 47.0 | 33.761 |
| 18AD42 | 500 µM | Indirubin | 8.5; 8.5; 8.5; 8.5 | 65.2 | 34.219 |
| 17AA70 | 0.5% (v/v) | DMSO | 8.5; 8.5; 8.0; 8.5 | 100.0[4] | 59.556 |
| 17AJ41 | 500 µM | Malassezin (CV-8684) | 8.5; 9.0; 8.0; 8.0 | 73.2 | 42.003 |
| 17AD43 | 500 µM | CV-8804 | 8.5; 8.5; 8.0; 8.5 | 86.6 | 35.898 |
| 17AD45 | 500 µM | CV-8803 | 8.5; 8.5; 8.0; 8.5 | 81.6 | 34.829 |
| 17AJ44/18AD36 | 200 µM/20% (v/v) | Compound E (AB12508)/ Linoleic acid | 7.5; 8.0; 7.5; 8.0 | 70.2 | 38.493 |
| 17AJ44/18AA22/18 AD42 + UV | 200 µM | Compound E (AB12508)/ Pityriacitrin (AB17014)/ Indirubin | 8.0; 8.5; 8.5; 8.0 | 67.1 | 34.371 |
| 17AJ44/18AA22/18 AD42 Dark | 200 µM | Compound E (AB12508)/ Pityriacitrin (AB17014)/ Indirubin | 8.0; 8.5; 8.5; 8.0 | 64.6 | 33.914 |
| 17AJ44/18AA22 + UV | 200 µM | Compound E (AB12508)/ Pityriacitrin (AB17014) | 8.0; 8.0; 8.0; 7.5 | 58.8 | 33.150 |
| 17AJ44/18AA22 Dark | 200 µM | Compound E (AB12508)/ Pityriacitrin (AB17014) | 8.0; 8.0; 8.0; 7.5 | 77.7 | 29.945 |
| 17AJ41/17AJ47 | 200 µM | Malassezin (CV-8684)/ Compound A5 (CV-8819) | 8.0; 8.0; 8.0; 7.5 | 62.3 | 35.287 |

Fig. 1 (Cont'd)

| | | | | | |
|---|---|---|---|---|---|
| 17AJ41/18AB74 | 200 µM/Neat | Malassezin (CV-8684)/ 2767-09 84-030118E w/ AB17011 @ 200 ppm | 8.0/5.0; 7.0/5.0; 7.5/5.0; 7.0/5.0 | 70.8 | 33.456 |
| 17AJ44/18AA14 | 200 µM | Compound E (AB12508)/ (AB17151) | 8.5; 7.5; 8.0; 7.5 | 30.5 | 24.908 |
| Positive Control | 1% (w/v) | Kojic acid | 4.0; 4.5; 4.0; 4.5 | 105.5 | 25.977 |
| Untreated tissues | NA | NA | NA | 100[3] | 21.398 |

1 – Calculated relative to the solvent control (17AA70 – DMSO)

2 – Solvent control value defined as 100% (baseline)

3 – Untreated tissues (Day 0) control value defined as 100% (baseline)

4 – Solvent control (Day 7) viability value defined as 100% (by default)

NA – Not Applicable

NCC – No Color Change (to the pH paper)

Fig. 2

| IIVS Test Article Number | Concentration | Sponsor's Designation | pH (Day 0, 2, 4, 6)^ | Mean Tissue Viability (%)[1] Day 7 | Melanin Concentration (µg/mL) – *from the linear curve* |
|---|---|---|---|---|---|
| 17AA70 | 0.5% (v/v) | DMSO | 8.0; 8.5; 8.5; 8.5 | 100[2] | 67.20 |
| 17AD43 | 750 µM | Compound A | 8.5; 8.5; 8.5; 8.5 | 87.4 | 53.79 |
| 17AJ41 | 500 µM | Malassezin (CV-8684) | 8.5; 8.5; 8.5; 8.5 | 72.4 | 48.07 |
| 18AE73 | 750 µM | Compound II | 8.5; 8.5; 8.5; 8.5 | 92.9 | 50.71 |
| 18AD42 | 500 µM | Indirubin | 8.5; 8.5; 8.5; 8.5 | 62.5 | 44.77 |
| 17AD45 | 650 µM | CV-8803 | 8.5; 8.5; 8.5; 8.5 | 87.6 | 50.93 |
| | 750 µM | | 8.5; 8.5; 8.5; 8.5 | 81.9 | 51.37 |
| 17AJ43 | 650 µM | Compound B (CV-8877) | 8.5; 8.5; 8.5; 8.5 | 63.0 | 36.19 |
| | 750 µM | | 8.5; 8.5; 8.5; 8.5 | 25.9 | 32.89 |
| 17AJ44 | 600 µM | Compound E (AB12508) | 8.5; 8.5; 8.5; 8.5 | 77.4 | 37.95 |
| | 700 µM | | 8.5; 8.5; 8.5 8.5 | 56.9 | 33.11 |
| | 800 µM | | 8.5; 8.5; 8.5; 8.5 | 40.0 | 43.01 |
| 18AA14 | 225 µM | AB17151 | 8.0; 8.0; Day 4*; 8.0 | 107.5 | 37.73 |
| | 300 µM | | 8.0; 8.0; 8.5; 8.0 | 78.8 | 32.01 |
| | 375 µM | | 8.0; 8.0; 8.5; 8.5 | 53.4 | 32.89 |
| | 450 µM | | 8.0; 8.5; 8.5; 8.5 | 36.5 | 35.53 |
| 18AE71 | 650 µM | Unknown Composition | 8.5; 8.5; 8.5; 8.5 | 87.0 | 35.09 |
| | 750 µM | | 9.0; 8.5; 8.5; 8.5 | 83.0 | 38.39 |
| 17AJ41/18AD42 | 250 µM | Malassezin (CV-8684)/ Indirubin | 8.0; 9.0; 8.5; 8.0 | 61.8 | 36.63 |
| 18AD42/18AA14 | 250 µM | Indirubin/AB17151 | 8.5; 8.0; 8.5; 8.5 | 34.3 | 34.43 |
| 17AJ44/17AJ43 | 100 µM | Compound E (AB12508)/ | 8.0; 8.5; 8.0; 8.0 | 105.9 | 47.19 |

| | | | | | |
|---|---|---|---|---|---|
| | | Compound B (CV-8877) | | | |
| 17AJ43/18AA14 | 100 µM | Compound B (CV-8877)/ AB17151 | 8.0; 8.0; 8.0; 8.0 | 108.4 | 42.35 |
| 17AJ44/18AA14 | 100 µM | Compound E (AB12508)/ AB17151 | 8.0; 8.0; 8.0 ; 8.5 | 92.2 | 39.93 |
| **Untreated tissues** | NA | NA | NA | 100[3] | 31.57 |

[1] – Calculated relative to the solvent control (17AA70 – DMSO)

[2] – Solvent control (Day 7) viability value defined as 100% (baseline)

Fig. 2 (Cont'd)

[3] – Untreated tissues (Day 0) control value defined as 100% (baseline)

NA – Not Applicable

Fig. 3
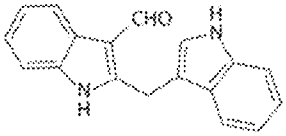
1. Malassezin (336)
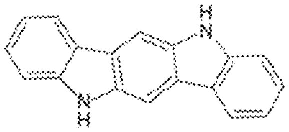
2. Indolo[3,2-b]carbazole (108)
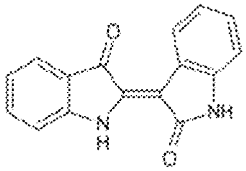
3. Indirubin (120)
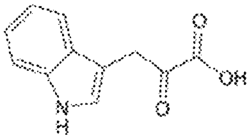
4. (Indol-3-yl)pyruvic acid
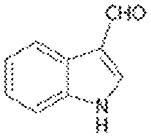
5. Indole-3-carbaldehyde
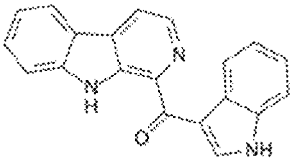
6. Pityriacitrin (215)
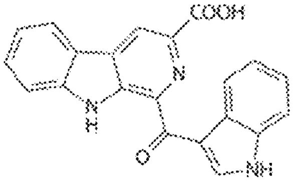
7. Pityriacitrin B (157)
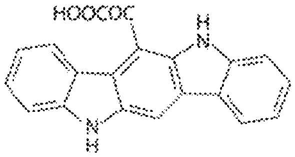
8. Malasseziazole A (158)
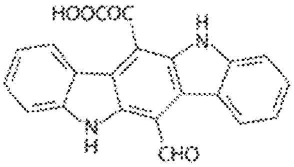
9. Malasseziazole B (158)

Fig. 3 (Cont'd)
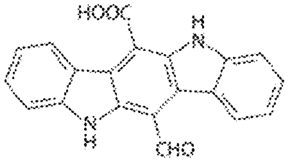
10. Malasseziazole C (158)
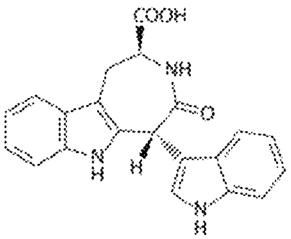
11. Malassezindole A (157)
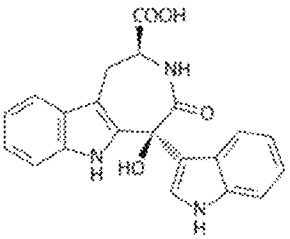
12. Malassezindole B (157)
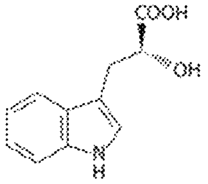
13. D-indole-3-lactic acid
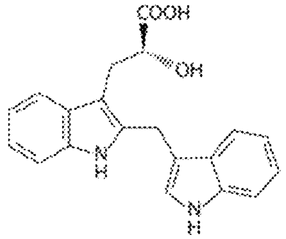
14. Malasseziaiactic acid (157)
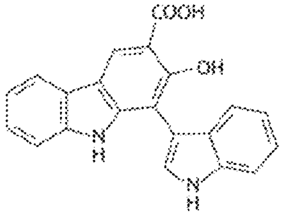
15. Pityriazole (157)

Fig. 3 (Cont'd)
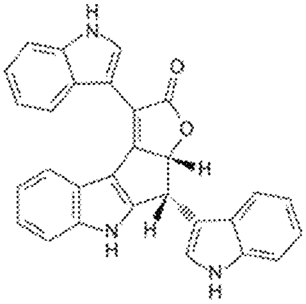
16. Malasseziacitrin (157)
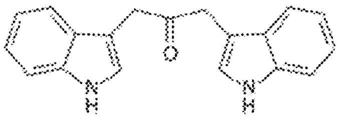
17. Malassezione (157)
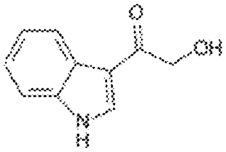
18. 2-hydroxy-1-(1H-indol-3-yl) ethanone (157)
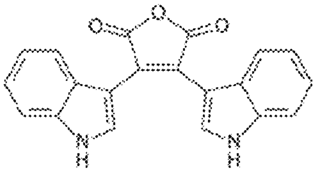
19. Pityrianhydride (157)
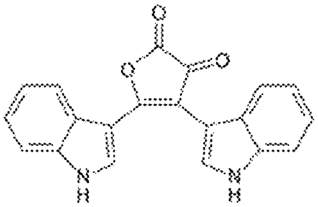
20. Pityrialactone (216)
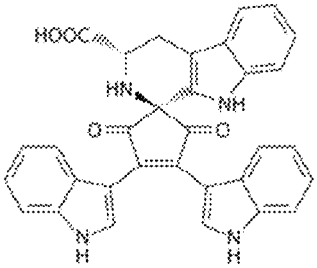
21. Pityriarubine A (158)

Fig. 3 (Cont'd)
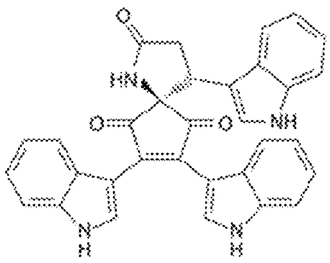
22. Pityriarubine B (158)
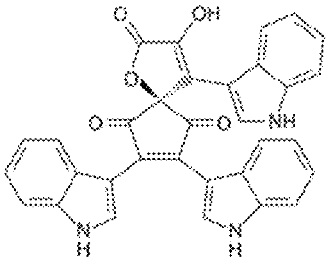
23. Pityriarubine C (158)
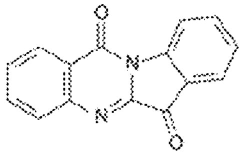
24. Tryptanthrin
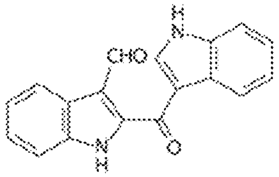
25. Keto-Malassezin (71)

Fig. 4

| IIVS Test Article Number | Concentration | Sponsor's Designation | pH | Mean Tissue Viability (%)[1] Day 7 | Melanin Concentration (μg/mL) – *from the linear curve* |
|---|---|---|---|---|---|
| 18AH47 | 0.5% (v/v) | DMSO (***Solvent control***) | 8.0 | 100[2] | 66.52 |
| 17AJ41 | 500 μM | Malassezin (CV-8684) (***Positive control***) | 8.0 | 78.2 | 42.97 |
| 17AJ55 | 650 μM | O52 (AB129761) | 8.5 | 94.7 | 49.91 |
| 18AA21 | 650 μM | Malassezia Indole A (AB17011) | 8.5 | 100.1 | 55.59 |
| 18AF50 | 300 μM | Compound AB17151 | 8.0 | 57.5 | 30.99 |
| 18AH15 | 300 μM | Compound AB17590 | 8.0 | 28.6 | 34.98 |
| 18AH21 | 650 μM | AB11644 | 8.5 | 95.2 | 66.52 |
| 18AH38 | 500 μM | Indole-3-carbaldehyde | 8.5 | 101.9 | 53.90 |
| 18AH39 | 500 μM | D-indole-3-lactic acid | 8.5 | 98.8 | 64.21 |
| 17AD42/17AJ41/17AJ47/17AJ55/18AA21/18AA22/18AA24/18AD42/18AH16/18AH20/18AH24/18AH38/18AH39/ 18AH44 | See Table 3 | Composition #1 | 8.5 | 61.7 | 32.67 |
| | See Table 4 | Composition #2 | 8.5 | 75.6 | 33.72 |
| **Untreated tissues** | NA | NA | NA | 100[3] | 20.89 |

1 – Calculated relative to the solvent control (18AH47 – DMSO)

2 – Solvent control (Day 7) viability value defined as 100% (baseline)

3 – Untreated tissues (Day 0) control value defined as 100% (baseline)

NA – Not Applicable

Fig. 5

| IIVS Test Article Number | Concentration | Sponsor's Designation | pH | Mean Tissue Viability (%)[1] | Melanin Concentration (µg/mL) – *from the linear curve* |
|---|---|---|---|---|---|
| | | | | Day 7 | |
| 18AH47 | 0.5% (v/v) | DMSO (***Solvent control***) | 8.0 | 100[2] | 53.69 |
| 17AD42/17AJ41/17AD46/17AJ55/18AA21/18AA22/18AA24/18AD42/18AH16/18AH20/ 18AH24/18AH38/18AH39/ 18AH44 | See Table 4 | Composition #2 (***Positive control***) | 7.5 | 64.8 | 30.59 |
| 17AJ41/17AD46/17AJ55/18AA21/18AD42/18AH20/ 18AH24/18AH38/18AH39/ 18AH44 | See Table 5 | Composition #3 | 8.0 | 65.2 | 25.93 |
| 17AD42/17AJ41/17AD46/17AJ55/18AA21/18AA24/18AD42/18AH20/18AH24/18AH38/18AH39/ 18AH44 | See Table 6 | Composition #4 | 7.5 | 63.0 | 31.70 |
| 17AD42/17AJ41/18AA22/18AA24/18AD42/18AH16/ 18AH24/18AH39/18AH44 | See Table 7 | Composition #5 | 8.0 | 63.9 | 34.15 |
| **Untreated tissues** | NA | NA | NA | 100[3] | 16.60 |

[1] – Calculated relative to the solvent control (18AH47 – DMSO)
[2] – Solvent control (Day 7) viability value defined as 100% (baseline)

[3] – Untreated tissues (Day 0) control value defined as 100% (baseline)
NA – Not Applicable

Fig. 8

| Dose Sequence | Skin Type | | | | | |
| --- | --- | --- | --- | --- | --- | --- |
| | I | II | III | IV | V | VI |
| 1st | 40 | 70 | 90 | 120 | 150 | 240 |
| 2nd | 60 | 90 | 120 | 150 | 180 | 270 |
| 3rd | 70 | 105 | 150 | 180 | 210 | 300 |
| 4th | 90 | 120 | 180 | 210 | 240 | 330 |
| 5th | 105 | 150 | 210 | 240 | 270 | 360 |
| 6th | 120 | 180 | 240 | 270 | 300 | 390 |

Fig. 9

| Treatment Area | Melanin | Erythema |
|---|---|---|
| Normal | 471 | 600 |
| | 471 | 611 |
| | 470 | 610 |
| | **470** | **607** |
| Involved Vehicle | 477 | 627 |
| | 477 | 627 |
| | 475 | 627 |
| | **476** | **627** |
| Day 7 | 459 | 615 |
| | 455 | 609 |
| | 453 | 617 |
| | 459 | 611 |
| | 456 | 619 |
| | 453 | 614 |
| | **456** | **614** |
| Day 3 | 468 | 613 |
| | 473 | 608 |
| | 471 | 604 |
| | 469 | 600 |
| | 470 | 595 |
| | **470** | **604** |
| Day 1 | 474 | 579 |
| | 475 | 585 |
| | 474 | 583 |
| | **474** | **582** |

Fig. 10

| Treatment Area | Melanin | Erythema |
|---|---|---|
| Day 9 Vehicle Cream | 473 | 619 |
| | 472 | 622 |
| | 473 | 621 |
| | **472** | **620** |
| Day 7 Vehicle Cream | 473 | 608 |
| | 473 | 610 |
| | 471 | 610 |
| | **472** | **609** |
| M Day 7 | 465 | 638 |
| | 465 | 636 |
| | 465 | 633 |
| | 463 | 639 |
| | **465** | **637** |
| No Treatment | 474 | 594 |
| | 474 | 594 |
| | 474 | 591 |
| | **474** | **593** |
| M Day 14 | 467 | 601 |
| | 471 | 593 |
| | 466 | 600 |
| | 469 | 603 |
| | **468** | **599** |
| M Day 10 | 475 | 590 |
| | 475 | 594 |
| | 473 | 595 |
| | **474** | **593** |

Fig. 10 (Cont'd)

| Treatment Area | Melanin | Erythema |
|---|---|---|
| M Day 8 | 483 | 602 |
| | 483 | 602 |
| | 484 | 605 |
| | **483** | **603** |
| M Day 3 | 474 | 609 |
| | 473 | 610 |
| | 476 | 610 |
| | **474** | **610** |
| M Day 1 | 481 | 585 |
| | 479 | 600 |
| | 474 | 602 |
| | **478** | **596** |
| Immediate 15 Min | 477 | 591 |
| | 482 | 602 |
| | 485 | 599 |
| | 492 | 605 |
| | 491 | 607 |
| | **485** | **601** |

Fig. 11

| | |
|---|---|
| 0 | None-no pink or redness |
| 1 | Minimal-negligibly pink or red |
| 2 | Mild-noticeably pink or red |
| 3 | Moderate-moderately pink or red |
| 4 | Moderately Severe-substantially dark pink or red |
| 5 | Severe-substantially very dark pink or red |

PHOTOPROTECTIVE COMPOSITIONS CONTAINING *MALASSEZIA*-DERIVED COMPOUNDS AND/OR CHEMICAL ANALOGS THEREOF

CROSS-REFERENCE TO RELATED APPLICATIONS

This application is a continuation of U.S. patent application Ser. No. 16/549,106, which claims the benefit of U.S. provisional application No. 62/722,412, filed Aug. 24, 2018, and of U.S. provisional application No. 62/742,657, filed Oct. 8, 2018. The entire contents of the aforementioned applications are incorporated by reference. Additionally, the entire contents of U.S. provisional application No. 62/306,468, filed Mar. 10, 2016, U.S. provisional application No. 62/656,769, filed Apr. 12, 2018, U.S. provisional application No. 62/668,007, filed May 7, 2018, U.S. provisional application No. 62/685,800, filed Jun. 15, 2018, U.S. provisional application No. 62/686,912, filed Jun. 19, 2018, U.S. patent application Ser. No. 15/455,932, filed Mar. 10, 2017, now U.S. Pat. No. 10,131,631, U.S. patent application Ser. No. 16/382,891, filed Apr. 12, 2019, U.S. patent application Ser. No. 16/405,127, filed May 7, 2019, and U.S. patent application Ser. No. 16/441,522, filed Jun. 14, 2019 are hereby incorporated by reference.

FIELD OF INVENTION

The present invention relates to compounds produced by or derived from a *Malassezia* yeast, as well as chemical analogs thereof. Compounds of the present invention, and compositions containing said compounds, have, among other beneficial properties, photoprotective properties. Methods of using the compounds and compositions of the present invention are also contemplated.

BACKGROUND OF THE INVENTION

Individuals around the world use skin brightening agents to achieve a number of cosmetic goals, including producing an anti-aging effect, correcting sun damage, and meeting certain cultural standards of beauty. Many commercially available skin brightening products, while effective to varying degrees, contain harmful ingredients, some of which have been linked to cancer. Thus, there exists a need for novel skin brightening agents and formulations that exhibit higher levels of safety and/or efficacy than agents currently on the market.

*Malassezia* is a genus of lipophilic yeast commonly found in the normal flora of human skin. *Malassezia* is responsible for a number of skin diseases, including *Tinea versicolor* (*pityriasis versicolor*), seborrheic dermatitis, and atopic dermatitis.

The natural habitat for *M. furfur* is the upper epidermis. However, exposure to ultraviolet light destroys the organism in its natural habitat. Therefore, UV filtering agents may be necessary for the survival of the organism. Two such UV-filtering indoles produced by the organism have been identified: pityriacitrin and pityrialactone. Pityriacitrin, first described in Mayser et al., 2002, is synthesized by *M. furfur*. It is a stable yellow lipophilic compound showing broad absorption in the UVA, UVB, and UVC spectrum. A similar compound from the genus *Paracoccus* has been isolated and patented as a UV protective agent. (Zhang et al., 2018).

Gambichler et al., 2007 investigated the UV protective effect of pityriacitrin in humans using in vitro and in vivo test methods. Spectrophotometry of pityriacitrin cream and vehicle was performed in the 290-400 nm wavelength range. UV transmission and the sun protection factor ("SPF") were assessed for different cream formulations. Using colorimetry, the authors evaluated erythema and pigmentation following irradiation of cream-protected and non-protected skin of healthy subjects. UVB as well as UVA transmission decreased with increasing pityriacitrin concentrations. An increase of pityriacitrin concentration of 1.25, 2.5, and 5% was associated with slightly increasing SPFs of 1.4, 1.5, and 1.7, respectively. The in vivo tests confirmed the validity of the SPF of pityriacitrin 5% cream determined in vitro. Overall, the UV protective effect of pityriacitrin was very weak, suggesting that pityriacitrin likely is only an inferior cofactor in the development of hypopigmentation in *pityriasis versicolor* alba lesions following sun exposure.

Further studies of the UV filtering effects of pityriacitrin were performed on human skin microflora. (Machowinski et al., 2006). The authors determined pityriacitrin has a UV-protective effect on *Candida albicans* and staphylococci with no toxicity in the ranges tested. The UV protective properties of pityrialactone have also been confirmed in a yeast model. (Mayser et al., 2003). Pityrialactone appears to be responsible for the yellow fluorescence of *Tinea Versicolor* under Wood's Light examination.

*Tinea versicolor* is a non-contagious skin disease caused by *Malassezia* overgrowth that locally alters pigmentation levels. *Malassezia* yeasts have two metabolic pathways for synthesizing melanin and tryptophan-derived indole pigments. Malassezin and Indirubin are tryptophan metabolites of *Malassezia* that may contribute to the depigmentation characteristic of *Malassezia* overgrowth.

The invention disclosed herein utilizes compounds produced by or derived from *Malassezia* yeast, including Malassezin, Indirubin, and chemical analogs thereof, as the basis for safe and efficacious skin brightening and skin darkening compositions. Photoprotective compositions comprising Malassezin, Indirubin, and chemical analogs thereof are also disclosed herein.

SUMMARY OF THE INVENTION

One embodiment of the present invention is a composition. The composition comprises one or more of the compounds listed in Table 1 or FIG. 3, or a chemical analog, crystalline form, hydrate, or pharmaceutically or cosmetically acceptable salt thereof.

Another embodiment of the present invention is a method for brightening skin in a subject. The method comprises contacting the subject with one or more of the compounds listed in Table 1 or FIG. 3, or a chemical analog, crystalline form, hydrate, or pharmaceutically or cosmetically acceptable salt thereof.

A further embodiment of the present invention is a method for inducing melanocyte apoptosis in a subject. The method comprises contacting the subject with one or more of the compounds listed in Table 1 or FIG. 3, or a chemical analog, crystalline form, hydrate, or pharmaceutically or cosmetically acceptable salt thereof.

An additional embodiment of the present invention is a method for modulating arylhydrocarbon receptor (AhR) activity in a subject. The method comprises contacting the subject with one or more of the compounds listed in Table 1 or FIG. 3, or a chemical analog, crystalline form, hydrate, or pharmaceutically or cosmetically acceptable salt thereof.

Another embodiment of the present invention is a method for modulating melanogenesis in a subject. The method comprises contacting the subject with one or more of the compounds listed in Table 1 or FIG. 3, or a chemical analog, crystalline form, hydrate, or pharmaceutically or cosmetically acceptable salt thereof.

Another embodiment of the present invention is a method for modulating melanin concentration in a subject. The method comprises contacting the subject with one or more of the compounds listed in Table 1 or FIG. 3, or a chemical analog, crystalline form, hydrate, or pharmaceutically or cosmetically acceptable salt thereof.

An additional embodiment of the present invention is a composition. The composition comprises one or more of the compounds listed in Table 1 or FIG. 3, or a chemical analog, crystalline form, hydrate, or pharmaceutically or cosmetically acceptable salt thereof.

A further embodiment of the present invention is a composition for brightening skin. The composition comprises one or more of the compounds listed in Table 1 or FIG. 3, or a chemical analog, crystalline form, hydrate, or pharmaceutically or cosmetically acceptable salt thereof.

Another embodiment of the present invention is a composition for inducing melanocyte apoptosis. The composition comprises one or more of the compounds listed in Table 1 or FIG. 3, or a chemical analog, crystalline form, hydrate, or pharmaceutically or cosmetically acceptable salt thereof.

An additional embodiment of the present invention is a composition for modulating arylhydrocarbon receptor (AhR) activity. The composition comprises one or more of the compounds listed in Table 1 or FIG. 3, or a chemical analog, crystalline form, hydrate, or pharmaceutically or cosmetically acceptable salt thereof.

A further embodiment of the present invention is a composition for modulating melanogenesis. The composition comprises one or more of the compounds listed in Table 1 or FIG. 3, or a chemical analog, crystalline form, hydrate, or pharmaceutically or cosmetically acceptable salt thereof.

Another embodiment of the present invention is a composition for modulating melanin concentration. The composition comprises one or more of the compounds listed in Table 1 or FIG. 3, or a chemical analog, crystalline form, hydrate, or pharmaceutically or cosmetically acceptable salt thereof.

An additional embodiment of the present invention is a method for brightening skin in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

A further embodiment of the present invention is a method for inducing melanocyte apoptosis in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

Another embodiment of the present invention is a method for modulating arylhydrocarbon receptor (AhR) activity in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

An additional embodiment of the present invention is a method for modulating melanogenesis in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

A further embodiment of the present invention is a method for modulating melanin concentration in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

Another embodiment of the present invention is a composition. The composition comprises a *Malassezia* yeast and a cosmetically or pharmaceutically acceptable vehicle, diluent, or carrier.

An additional embodiment of the present invention is a composition. The composition comprises a compound having the structure of the following formula:

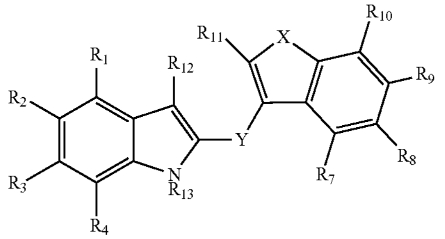

wherein:

X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (═O) group or a $C_{3-6}$ cycloalkyl; $R_{12}$ is selected from the group consisting of hydrogen, —$COR^a$, and $R_{16}$, each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof, and a cosmetically or pharmaceutically acceptable vehicle, diluent, or carrier.

A further embodiment of the present invention is a composition. The composition comprises a compound having the structure of the following formula:

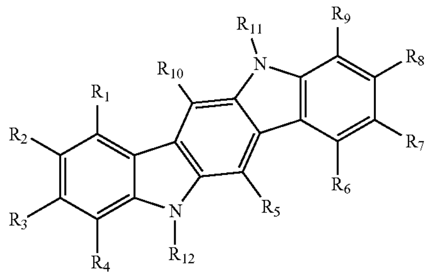

wherein:

$R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_D$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_D$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof, and a cosmetically or pharmaceutically acceptable vehicle, diluent, or carrier.

Another embodiment of the present invention is a composition. The composition comprises a compound listed in Table 1 or FIG. 3, or a chemical analog, crystalline form, hydrate, or cosmetically or pharmaceutically acceptable salt thereof, and a cosmetically or pharmaceutically acceptable vehicle, diluent, or carrier.

An additional embodiment of the present invention is a method of treating or preventing UV-induced skin damage in a subject. The method comprises contacting the subject with any of the compositions disclosed herein.

A further embodiment of the present invention is a method of treating or preventing UV-induced erythema in a subject. The method comprises contacting the subject with any of the compositions disclosed herein.

Another embodiment of the present invention is a method of treating or preventing UV-induced aging of the skin in a subject. The method comprises contacting the subject with any of the compositions disclosed herein.

An additional embodiment of the present invention is a method of treating or preventing sunburn in a subject. The method comprises contacting the subject with any of the compositions disclosed herein.

A further embodiment of the present invention is a method of treating or preventing UV-induced hyperpigmentation in a subject. The method comprises contacting the subject with any of the compositions disclosed herein.

Another embodiment of the present invention is a method for brightening skin in a subject. The method comprises contacting the subject with any of the compositions disclosed herein.

An additional embodiment of the present invention is a method for inducing melanocyte apoptosis in a subject. The method comprises contacting the subject with any of the compositions disclosed herein.

A further embodiment of the present invention is a method for modulating arylhydrocarbon receptor (AhR) activity in a subject. The method comprises contacting the subject with any of the compositions disclosed herein.

Another embodiment of the present invention is a method for modulating melanogenesis in a subject. The method comprises contacting the subject with any of the compositions disclosed herein.

An additional embodiment of the present invention is a method for modulating melanin concentration in a subject. The method comprises contacting the subject with any of the compositions disclosed herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1-2 are tables showing mean tissue viability and melanin concentration data ascertained from separate experiments with MelanoDerm™ substrates treated with varying concentrations of the test articles shown.

FIG. 3 shows compounds produced by *Malassezia.*

FIGS. 4-5 are tables showing mean tissue viability and melanin concentration data ascertained from separate experiments with MelanoDerm™ substrates treated with varying concentrations of the test articles/test compositions shown.

FIG. 8 is a table showing a Dualight scale for Skin Types I-VI.

FIG. 9 is a table showing Mexameter MX 16 measurements of melanin and erythema at Day 8 after Day 7 irradiation.

FIG. 10 is a table showing Mexameter MX 16 measurements of melanin and erythema at Day 15 after Day 14 irradiation.

FIG. 11 is a table showing an erythema scale of numerical values associated with various degrees of erythema.

DETAILED DESCRIPTION OF THE INVENTION

Figure 6A:
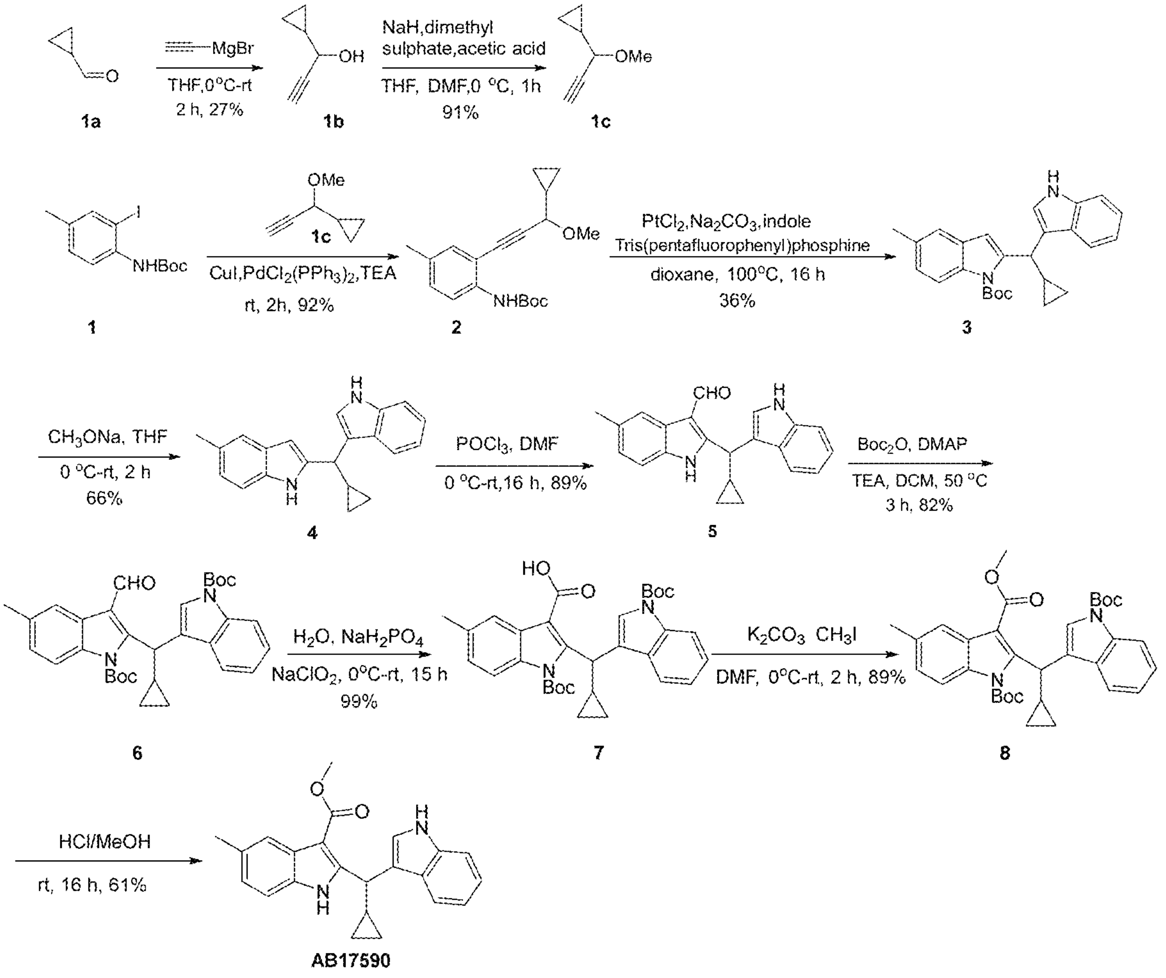
FIGS. 6A-6B show synthesis schemes for AB17590 (FIG. 6A) and AB17653, AB17654, AB17655, AB17656, AB17657, and AB17658 (FIG. 6B).

An additional embodiment of the present invention is a composition. The composition comprises one or more of the compounds listed in Table 1 or FIG. 3, or a chemical analog, crystalline form, hydrate, or pharmaceutically or cosmetically acceptable salt thereof.

Another embodiment of the present invention is a composition for brightening skin. The composition comprises one or more of the compounds listed in Table 1 or FIG. 3, or a chemical analog, crystalline form, hydrate, or pharmaceutically or cosmetically acceptable salt thereof.

A further embodiment of the present invention is a composition for inducing melanocyte apoptosis. The composition comprises one or more of the compounds listed in Table 1 or FIG. 3, or a chemical analog, crystalline form, hydrate, or pharmaceutically or cosmetically acceptable salt thereof.

An additional embodiment of the present invention is a composition for modulating arylhydrocarbon receptor (AhR) activity. The composition comprises one or more of the compounds listed in Table 1 or FIG. 3, or a chemical analog, crystalline form, hydrate, or pharmaceutically or cosmetically acceptable salt thereof.

Another embodiment of the present invention is a composition for modulating melanogenesis. The composition comprises one or more of the compounds listed in Table 1 or FIG. 3, or a chemical analog, crystalline form, hydrate, or pharmaceutically or cosmetically acceptable salt thereof.

A further embodiment of the present invention is a composition for modulating melanin concentration. The composition comprises one or more of the compounds listed in Table 1 or FIG. 3, or a chemical analog, crystalline form, hydrate, or pharmaceutically or cosmetically acceptable salt thereof.

An additional embodiment of the present invention is a method for brightening skin in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

Another embodiment of the present invention is a method for inducing melanocyte apoptosis in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

A further embodiment of the present invention is a method for modulating arylhydrocarbon receptor (AhR) activity in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

An additional embodiment of the present invention is a method for modulating melanogenesis in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

Another embodiment of the present invention is a method for modulating melanin concentration in a subject. The method comprises contacting the subject with a composition, the composition comprising one or more of the compounds listed in Table 1 or FIG. 3, or a chemical analog, crystalline form, hydrate, or pharmaceutically or cosmetically acceptable salt thereof.

In preferred embodiments, the compositions of the present invention comprise the compounds listed in Table 5.

In other preferred embodiments, the compositions of the present invention comprise the compounds listed in Table 6.

In additional preferred embodiments, the compositions of the present invention comprise the compounds listed in Table 7.

In further preferred embodiments, the compositions of the present invention comprise the compounds listed in Table 8.

In other preferred embodiments, the compositions of the present invention comprise the compounds listed in Table 9.

In additional preferred embodiments, the methods of the present invention comprise contacting a subject with a composition comprising the compounds listed in Table 5.

In further preferred embodiments, the methods of the present invention comprise contacting a subject with a composition comprising the compounds listed in Table 6.

In other preferred embodiments, the methods of the present invention comprise contacting a subject with a composition comprising the compounds listed in Table 7.

In additional preferred embodiments, the methods of the present invention comprise contacting a subject with a composition comprising the compounds listed in Table 8.

In further preferred embodiments, the methods of the present invention comprise contacting a subject with a composition comprising the compounds listed in Table 9.

A further embodiment of the present invention is a composition. The composition comprises a *Malassezia* yeast, and a cosmetically or pharmaceutically acceptable vehicle, diluent, or carrier.

An additional embodiment of the present invention is a composition. The composition comprises a compound having the structure of the following formula:

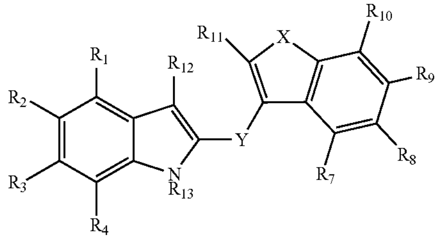

wherein:

X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$, $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$, each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$;

or a crystalline form, hydrate, or cosmetically or pharmaceutically acceptable salt thereof, and a cosmetically or pharmaceutically acceptable vehicle, diluent, or carrier.

Another embodiment of the present invention is a composition. The composition comprises a compound having the structure of the following formula:

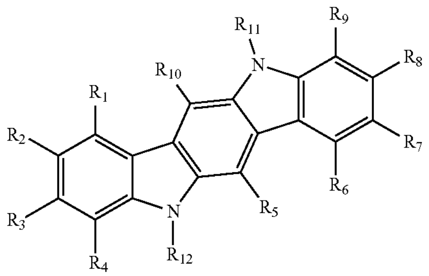

wherein:

$R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_D$ and —CHO; $R_2$ and $R_3$ are independently selected from the group consisting of hydrogen, hydroxyl, halogen, CN, $R_{13}$, $OR_{13}$, $OCOR_D$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_D$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl;

or a crystalline form, hydrate, or cosmetically or pharmaceutically acceptable salt thereof, and a cosmetically or pharmaceutically acceptable vehicle, diluent, or carrier.

A further embodiment of the present invention is a composition. The composition comprises a compound listed in Table 1 or FIG. 3, or a chemical analog, crystalline form, hydrate, or cosmetically or pharmaceutically acceptable salt thereof, and a cosmetically or pharmaceutically acceptable vehicle, diluent, or carrier.

In preferred embodiments, any of the compositions of the present invention prevent UV-induced erythema in a subject.

In preferred embodiments, any of the compositions of the present invention reduce epidermal melanin in a subject.

In preferred embodiments, any of the compositions of the present invention produce a photo-protective or UV-protective effect in a subject.

In preferred embodiments, any of the compositions of the present invention filter, absorb, or reflect UV.

In preferred embodiments, any of the compositions of the present invention prevent hyperpigmentation and/or promote hypopigmentation.

In preferred embodiments, any of the compositions of the present invention is a sunscreening agent, a photo-protective agent, and/or a UV-protective agent.

An additional embodiment of the present invention is a method of treating or preventing UV-induced skin damage in a subject. The method comprises contacting the subject with any of the compositions disclosed herein.

Another embodiment of the present invention is a method of treating or preventing UV-induced erythema in a subject. The method comprises contacting the subject with any of the compositions disclosed herein.

A further embodiment of the present invention is a method of treating or preventing UV-induced aging of the skin in a subject. The method comprises contacting the subject with any of the compositions disclosed herein.

An additional embodiment of the present invention is a method of treating or preventing sunburn in a subject. The method comprises contacting the subject with any of the compositions disclosed herein.

Another embodiment of the present invention is a method of treating or preventing UV-induced hyperpigmentation in a subject. The method comprises contacting the subject with any of the compositions disclosed herein.

A further embodiment of the present invention is a method for brightening skin in a subject. The method comprises contacting the subject with any of the compositions disclosed herein.

An additional embodiment of the present invention is a method for inducing melanocyte apoptosis in a subject. The method comprises contacting the subject with any of the compositions disclosed herein.

Another embodiment of the present invention is a method for modulating arylhydrocarbon receptor (AhR) activity in a subject. The method comprises contacting the subject with any of the compositions disclosed herein.

A further embodiment of the present invention is a method for modulating melanogenesis in a subject. The method comprises contacting the subject with any of the compositions disclosed herein.

An additional embodiment of the present invention is a method for modulating melanin concentration in a subject. The method comprises contacting the subject with any of the compositions disclosed herein.

Definitions

As used herein, the term "compound" refers to two or more atoms that are connected by one or more chemical bonds. In the present invention, chemical bonds include, but are not limited to, covalent bonds, ionic bonds, hydrogen bonds, and van der Waals interactions. Covalent bonds of the present invention include single, double, and triple bonds. Compounds of the present invention include, but are not limited to, organic molecules.

Organic compounds/molecules of the present invention include linear, branched, and cyclic hydrocarbons with or without functional groups. The term "$C_{x-y}$" when used in conjunction with a chemical moiety, such as, alkyl, alkenyl, alkynyl or alkoxy is meant to include groups that contain from x to y carbons in the chain. For example, the term "$C_{x-y}$ alkyl" means substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, and the like. The terms "$C_{x-y}$ alkenyl" and "$C_{x-y}$ alkynyl" refer to substituted or unsubstituted unsaturated aliphatic groups analogous in length and possible substitution to the alkyls described above, but containing at least one double or triple bond, respectively.

The term "aliphatic", as used herein, means a group composed of carbon and hydrogen atoms that does not contain aromatic rings. Accordingly, aliphatic groups include alkyl, alkenyl, alkynyl, and carbocyclyl groups.

As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, Isohexyl, and the like. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —$CO_2R'$, —COOH, —CN, —OH, —OR', —$NH_2$, —NHR', —$N(R')_2$, —SR' or —$SO_2R'$, wherein each instance of R' independently is $C_1$-$C_3$ alkyl. In embodiments, the alkyl is unsubstituted. In embodiments, the alkyl is substituted (e.g., with 1, 2, 3, 4, 5, or 6 substituent groups as described herein). For example, the term "hydroxyalkyl" refers to an alkyl group as described herein comprising a hydroxyl (—OH) substituent and includes groups such as —$CH_2OH$.

As used herein, "alkenyl" means any linear or branched hydrocarbon chains having one or more unsaturated carbon-carbon double bonds that may occur in any stable point along the chain, e g "$C_2$-$C_{20}$ alkenyl" refers to an alkenyl group having 2-20 carbons. For example, an alkenyl group includes prop-2-enyl, but-2-enyl, but-3-enyl, 2-methylprop- 2-enyl, hex-2-enyl, hex-5-enyl, 2,3-dimethylbut-2-enyl, and the like. In embodiments, the alkenyl comprises 1, 2, or 3 carbon-carbon double bonds. In embodiments, the alkenyl comprises a single carbon-carbon double bond. In embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the alkenyl is unsubstituted. In embodiments, the alkenyl is substituted (e.g., with 1, 2, 3, 4, 5, or 6 substituent groups as described herein).

As used herein, "alkynyl" means any hydrocarbon chain of either linear or branched configuration, having one or more carbon-carbon triple bonds occurring in any stable point along the chain, e.g. "$C_2$-$C_{20}$ alkynyl" refers to an alkynyl group having 2-20 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, and the like. In embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the alkynyl is unsubstituted. In embodiments, the alkynyl is substituted (e.g., with 1, 2, 3, 4, 5, or 6 substituent groups as described herein).

As used herein, the term "cycloalkyl" means a nonaromatic, saturated, cyclic group, e.g. "$C_3$-$C_{10}$ cycloalkyl." In embodiments, a cycloalkyl is monocyclic. In embodiments, a cycloalkyl is polycyclic (e.g., bicyclic or tricyclic). In polycyclic cycloalkyl groups, individual rings can be fused, bridged, or spirocyclic. Examples of a cycloalkyl group include cyclopropyl, cyclobutyl, cyclopentyl, cyclohexyl, norbornanyl, bicyclo[3.2.1]octanyl, octahydro-pentalenyl, and spiro[4.5]decanyl, and the like. The term "cycloalkyl" may be used interchangeably with the term "carbocycle". A cycloalkyl group may be unsubstituted or substituted with one or more substituent groups as described herein. For example, a cycloalkyl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the cycloalkyl is unsubstituted. In embodiments, the cycloalkyl is substituted (e.g., with 1, 2, 3, 4, 5, or 6 substituent groups as described herein).

As used herein, the term "halogen" means fluorine, chlorine, bromine, or iodine.

As used herein, an "aromatic compound", "aromatic", or compound containing an "aromatic ring" is an aryl or a heteroaryl compound. The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, indole, imidazole, oxazole, thiazole, pyrazole, pyridine, pyrazine, pyridazine, and pyrimidine, and the like. Preferably, certain compounds of the present invention include at least one, preferably two, indole groups as well as at least one aldehyde group.

The term "substituted" means moieties having at least one substituent that replaces a hydrogen atom on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, and the like. The permissible substituents can be one or more and the same or different for appropriate organic compounds.

As used herein, the term "heterocycle" or "heterocyclic" means a monocyclic, bicyclic, or tricyclic ring system containing at least one heteroatom. Heteroatoms include, but are not limited to, oxygen, nitrogen, and sulfur.

A monocyclic heterocyclic ring consists of, for example, a 3, 4, 5, 6, 7, 8, 9, or 10-membered ring containing at least one heteroatom. Representative examples of monocyclic heterocyclic rings include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxido-thiomorpholinyl (thiomorpholine sulfone), thiopyranyl, and trithianyl.

A bicyclic heterocyclic ring is, by non-limiting example, a monocyclic heterocyclic ring fused to a distal aryl ring or the monocyclic heterocyclic ring fused to a distal cycloalkyl ring or the monocyclic heterocyclic ring fused to a distal cycloalkenyl ring or the monocyclic heterocyclic ring fused to a distal monocyclic heterocyclic ring, or the monocyclic heterocyclic ring fused to a distal monocyclic heteroaryl ring. Representative examples of bicyclic heterocyclic rings include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

A tricyclic heterocyclic ring is, by non-limiting example, a bicyclic heterocyclic ring fused to a phenyl group or the bicyclic heterocyclic ring fused to a cycloalkyl group or the bicyclic heterocyclic ring fused to a cycloalkenyl group or the bicyclic heterocyclic ring fused to another monocyclic heterocyclic ring. Representative examples of tricyclic heterocyclic rings include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

Heterocycles of the present invention can be substituted with substituents independently selected from, by non-limiting example, alkenyl, alkoxy, alkoxyalkyl, alkoxyalkynyl, alkoxycarbonyl, alkoxycarbonylalkyl, alkoxy-NH═C(alkyl)-, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, cycloalkyl, carbonyl, cycloalkylalkyl, formyl, halogen, haloalkyl, hydroxy, hydroxyalkyl, hydroxycycloalkyl, mercapto, nitro, oxo, and phenyl.

As used herein, "skin pigmentation modulating" and grammatical variations thereof refer generally to skin brightening as well as skin darkening effects of the compounds and compositions of the present invention.

As used herein, "skin brightening" and grammatical variations thereof refer generally to any actual or perceived reduction in skin pigmentation. Skin brightening methods have been used to reduce pigmentation of hyperpigmented areas of skin resulting from age, sun exposure, or a hyperpigmentation disorder. Application of the compounds and compositions of the present invention to, for example, a subject's skin, can reduce pigmentation so that the skin appears lighter or whiter than before said application. Skin pigmentation can be assessed in a number of ways, including, but not limited to, visual assessments using, for example, the von Luschan chromatic scale, the Fitzpatrick skin typing test (Fitzpatrick et al., 1988) and the Taylor Hyperpigmentation Scale (Taylor et al., 2005) and reflectance spectrophotometry methods (Zonios, et al., 2001). For example, the Fitzpatrick skin typing test includes six types of skin (I-VI), and Type VI skin that becomes Type V or less has been "brightened" as the term is used herein. As discussed further below, skin brightening can result due to a number of phenomena, including, but not limited to, modulation of melanocyte activity, induction of melanocyte apoptosis, or modulation of arylhydrocarbon receptor (AhR) activity, melanogenesis, melanosome biogenesis, melanosome transfer, or melanin concentration.

Likewise, as used herein, "skin darkening" and grammatical variations thereof refer generally to any actual or perceived increase in skin pigmentation. Skin darkening methods have been used to increase pigmentation of hypopigmented areas of skin resulting from, for example, a hypopigmentation disorder. Application of the compounds and compositions of the present invention to, for example, a subject's skin, can increase pigmentation so that the skin appears darker than before said application.

Certain compounds of the present invention are produced by, derived from, isolated from, or isolatable from a *Malassezia* yeast. *Malassezia* yeasts are yeasts of the genus *Malassezia* and include, but are not limited to, *Malassezia globosa, Malassezia restricta, Malassezia furfur, Malassezia sympodialis, Malassezia slooffiae, Malassezia obtusa, Malassezia pachydermatis, Malassezia dermatis, Malassezia japonica, Malassezia nana, Malassezia yamatoensis, Malassezia equine, Malassezia caprae*, and *Malassezia cuniculi*. (Guého, et al., 1996; Gaitanis, et al., 2013). *Malassezia* yeast are part of the normal human cutaneous flora and typically produce no pathogenic effects. However, *Malassezia* yeast can cause a number of diseases, including, but not limited to *pityriasis versicolor* (both the hyperpigmented and hypopigmented varieties), seborrheic dermatitis, dandruff, atopic dermatitis, *Malassezia* folliculitis, psoriasis, and confluent and reticulated papillomatosis. (Gaitanis, et al., 2013).

As used herein, the term "chemical analog" refers to a compound that is structurally related to a parent compound and contains different functional groups or substituents. For example, parent compounds of the present invention include malassezin and indirubin, and chemical analogs of malassezin and indirubin contain certain functional groups and substituents that are distinct from malassezin and indirubin, respectively. Chemical analogs of the present invention may have significant advantages over a given parent compound, including a pharmacokinetic profile suitable for cosmetic or pharmaceutical use. In some embodiments, a chemical analog is generated from a parent molecule by one or more chemical reactions. In other embodiments, alternative synthesis schemes that do not originate with a parent compound can be used to generate chemical analogs of the present invention.

A compound of the present invention is produced by a *Malassezia* yeast if, over the course of its lifecycle, a *Malassezia* yeast would synthesize, secrete, accumulate, or otherwise generate the compound under appropriate growth conditions. *Malassezia* yeast secrete different compounds depending on what their growth media is supplemented with. (Nazzaro-Porro, et al., 1978). The present invention includes any compound produced by a *Malassezia* yeast under any growth condition, but preferred compounds include, for example, malassezin, indirubin, and chemical analogs thereof.

A compound of the present invention is derived from a *Malassezia* yeast if, at any time over the course of the yeast's lifecycle, the compound existed on or in the yeast.

Malassezin is one example of a compound produced by a *Malassezia* yeast of the present invention. Malassezin, also known as 2-(1H-indol-3-ylmethyl)-1H-indole-3-carbaldehyde, is a tryptophan metabolite originally isolated from *Malassezia furfur*. Malassezin is a known agonist of the arylhydrocarbon receptor (AhR), a receptor implicated in cell growth, differentiation, and gene expression. (Wille et al., 2001). Malassezin also induces apoptosis in primary human melanocytes. (Kramer, et al., 2005). Recently, certain chemical analogs of malassezin were synthesized by Winston-McPherson and colleagues, who examined the analogs' AhR agonist activity. (Winston-McPherson, et al., 2014).

Indirubin is another example of a compound produced by a *Malassezia* yeast of the present invention. Indirubin is a metabolite isolated from *Malassezia furfur* Indirubin is a known agonist of the arylhydrocarbon receptor (AhR), a receptor implicated in cell growth, differentiation, and gene expression.

As used herein, the term "melanocyte" refers to a dendritic cell of the epidermis that normally synthesizes tyrosinase and, within melanosomes, the pigment melanin Melanocytes of the present invention exhibit upregulation of certain genes, including, but not limited to, one or more of the following: tyrosinase (oculocutaneous albinism IA), microphthalmia-associated transcription factor, alpha-2-macroglobulin, tyrosinase-related protein 1, solute carrier family 16, GS3955 protein, v-kit Hardy-Zuckerman 4 feline sarcoma, ocular albinism 1, Rag D protein, glycogenin 2, G-protein-coupled receptor, family C, oculocutaneous albinism II, deleted in esophageal cancer 1, melan-A, SRY-box 10, ATPase, Class V, type 10C, matrix metalloproteinase 1, latent transforming growth factor beta b, ATP-binding cassette, sub-family C, hydroxyprostaglandin dehydrogenase 15, transmembrane 7 superfamily member 1, glutaminyl-peptide cyclotransferase, and other genes identified by Lee and colleagues. (Lee, et al., 2013).

Melanocytes, like many other cell types, undergo programmed cell death or, apoptosis. Melanocyte apoptosis pathways are known to those of skill in the art (Wang, et al., 2014), and apoptosis pathways generally have been reviewed by Elmore (Elmore, 2007). A compound or composition of the present invention "induces" melanocyte apoptosis by, for example, causing the activation of certain pro-apoptotic signal transduction pathways or causing the repression of certain anti-apoptotic pathways in a melanocyte. It is envisioned that the compounds or compositions of the present invention can directly activate/repress an apoptosis-related pathway by directly interacting with a signaling molecule of the pathway or by indirectly interacting with a molecule of the pathway via direct interaction with one or more intermediary molecules that do not typically function within the pathway.

Melanocyte activity can be modulated in a number of ways contemplated in the present invention, including, but not limited to, inducing melanocyte apoptosis or altering melanocyte gene expression, cell motility, cell growth, melanin production, melanosome biogenesis, or melanosome transfer.

As used herein, the terms "modulate", "modulating", and grammatical variations thereof refer to an adjustment of a biological activity or phenomenon to a desired level. It is envisioned that "modulation" of the present invention includes adjustments that increase or decrease the levels of the biological activity or phenomenon.

As used herein, the terms "agonist", "agonizing", and grammatical variations thereof refer to a molecule that triggers (e.g., initiates or promotes), partially or fully enhances, stimulates or activates one or more biological activities. Agonists of the present invention may interact with and activate a receptor, thereby inititating a physiological or pharmacological response characteristic of that receptor. Agonists of the present invention include naturally occurring substances as well as synthetic substances.

As used herein, the terms "antagonist", "antagonizing", and grammatical variations thereof refer to a molecule that partially or fully suppresses, inhibits, or deactivates one or more biological activities. Antagonists of the present invention may competitively bind to a receptor at the same site as an agonist, but does not activate the intracellular response initiated by the active form of the receptor. Antagonists of the present invention may inhibit intracellular responses of an agonist or partial agonist.

An arylhydrocarbon receptor (AhR) of the present invention is any arylhydrocarbon receptor that naturally exists in a subject as described herein. Arylhydrocarbon receptors are known to those of skill in the art. (Noakes, 2015). Agonists of arylhydrocarbon receptors include, but are not limited to, tryptophan-related compounds such as kynurenine, kynurenic acid, cinnabarinic acid, and 6-formylindolo [3,2-1)] carbazole (FICZ). Malassezin is also known as an aryl hydrocarbon receptor agonist. (Wille, et al., 2001).

As used herein, the compounds, compositions, and methods of the present invention can be used to improve hyperpigmentation caused by a hyperpigmentation disorder by, for example, reducing the level of hyperpigmentation in areas affected by a hyperpigmentation disorder, slowing further hyperpigmentation, or preventing further hyperpigmentation from occurring. However, because every subject may not respond to a particular dosing protocol, regimen, or process, improving hyperpigmentation caused by a hyperpigmentation disorder does not require that the desired physiologic response or outcome be achieved in each and every subject or subject population. Accordingly, a given subject or subject population may fail to respond or respond inadequately to dosing, but other subjects or subject populations may respond and, therefore, experience improvement in their hyperpigmentation disorder.

As used herein, the term "hyperpigmentation" is an actual or a perceived skin disorder of excessive dark color. The skin impairment can be actual, for example, attributed to age, excessive sun exposure, or a disease or condition leading to dark skin areas. The dark skin areas can be in the form of spots, blotches, or relatively large areas of dark color. The skin impairment also can be perceived, for example, a perception by an individual that his/her skin shade is too dark. The individual may have a cosmetic desire to lighten the skin shade.

Hyperpigmentation disorders are disorders in which hyperpigmentation is the primary symptom as well as disorders in which hyperpigmentation occurs as a secondary symptom. Hyperpigmentation disorders of the present invention include, but are not limited to, congenital hyperpigmentation disorders and acquired hyperpigmentation disorders. Congenital hyperpigmentation disorders of the present invention include, but are not limited to, those involving epidermal hyperpigmentation (nevus cell nevus, Spitz nevus, and nevus spilus), dermal hyperpigmentation (blue nevus, nevus Ohta, dermal melanosis, nevus Ito, and Mongolian spot), ephelides, acropigmentation reticularis, Spitzenpigment/acropigmentation, and lentiginosis (generalized lentiginosis, LEOPARD syndrome, inherited patterned lentiginosis, Carney complex, Peutz-Jeghers syndrome, Laugier-Hunziker-Baran syndrome, and Cronkhite-Canada syndrome). (Yamaguchi, et al., 2014). Acquired hyperpigmentation disorders of the present invention include, but are not limited to, senile lentigines/lentigo, melasma/chloasma, Riehl's melanosis, labial melanotic macule, penile/vulvovaginal melanosis, erythromelanosis follicularis faciei Kitamura, UV-induced pigmentation (tanning and pigmentation petaloides actinica), postinflammatory pigmentation (friction melanosis and ashy dermatosis), chemical/drug-induced pigmentation (polychlorinated biphenyl, arsenic, 5-FU, bleomycin, cyclophosphamide, methotrexate, chlorpromazine, phenytoin, tetracycline, and chloroquine), pigmentary demarcation lines, and foreign material deposition (such as carotene, silver, gold, mercury, bismuth, and tattoos). Hyperpigmentation related with systemic disorders includes metabolism/enzyme disorders (hemochromatosis, Wilson's disease, Gaucher's disease, Niemann-Pick's disease, amyloidosis, ochronosis, acanthosis *nigricans*, and *porphyria* cutanea *tarda*), endocrine disorders (Addison's disease, Cushing syndrome, and hyperthyroidism), nutritional disorders (pellagra, vitamin B12 deficiency, folic acid deficiency, vagabond's disease, and prurigo pigmentosa), mastocytosis, collagen diseases, liver dysfunction, and kidney dysfunction. Hyperpigmentation can also be related with infectious diseases (measles, syphilis, and *Malassezia furfur*) and syndromes (von Recklinghausen's disease, Sotos syndrome, POEMS syndrome, Naegeli syndrome, Cantu syndrome, McCune-Albright syndrome, Watson syndrome, and Bloom syndrome). (Yamaguchi, et al., 2014).

Melanin is a naturally produced pigment that gives color to skin and hair. Melanin is produced by melanocytes in organelles known as melanosomes by a process known as melanogenesis. A compound or composition of the present invention modulates melanin production (a/k/a melanogenesis) in a subject by, for example, modulating melanosome biogenesis and directly or indirectly inhibiting melanin synthesis at the enzymatic level.

Melanosome biogenesis occurs via four stages: Stage I is characterized by pre-melanosomes, which are essentially non-pigmented vacuoles. In stage II, pre-melanosomes develop striations on which melanin is deposited in stage III. Stage IV results in mature melanosomes that are rich in melanin content. Compounds and compositions of the present invention modulate melanosome biogenesis by inhibiting or attenuating the biological processes that normally promote any or all of these stages. (Wasmeier, et al., 2008).

Melanin synthesis primarily involves three enzymes: tyrosinase, tyrosinase related protein-1, and dopachrome tautomerase. Additional factors that affect intracellular trafficking of these enzymes include, but are not limited to, BLOC-1, OA1, and SLC45A2. The compounds and compositions of the present invention can modulate melanin production by, for example, inhibiting or attenuating the activity of any of these enzymes or factors. (Yamaguchi, et al., 2014).

Once melanosomes have formed and melanin has been synthesized, melanosomes need to be transferred from epidermal melanocytes to skin and hair keratinocytes. Melanosomes originate near the nucleus of melanocytes and are transported to the periphery of melanocytes along microtubules and actin filaments. Compounds and compositions of the present invention modulate melanosome transfer by interfering with any of the biological processes that result in the transport of melanosomes from the perinuclear region, to the melanocyte periphery, and into adjacent keratinocytes.

Melanin concentration may be modulated by, for example, increasing or decreasing melanogenesis or promoting melanin degradation in, or elimination from, a subject.

A compound isolated from a *Malassezia* yeast of the present invention necessarily exists, before isolation, in a *Malassezia* yeast or is produced by a *Malassezia* yeast. Therefore, a compound isolated from a *Malassezia* yeast is derived from actual yeast cells. Standard protocols for extracting compounds from cellular material are known to those of skill in the art.

A compound isolatable from a *Malassezia* yeast need not be derived from actual yeast cells. Instead, synthetic reactions can be used to generate compounds produced in yeast without the involvement of actual yeast cells. Organic synthesis reactions are well known to those of skill in the art and can be used in this regard.

As used herein, the term "epidermal melanin" refers to melanin that is produced in, transported to, or otherwise found in the epidermis.

As used herein, the term "reduce" and grammatical variations thereof mean to cause a decrease in the level of a given biological phenomenon or species. For example, compounds and compositions of the present invention reduce epidermal melanin in a subject, meaning that the compounds and compositions of the present invention elicit a decrease in the level of epidermal melanin in the subject. The term "reduce" and grammatical variations thereof can mean, for example, decreasing the level of a given phenomenon or species by at least 5%, 10%, 25%, 50%, 75%, or 100%.

As used herein, the term "contacting" and grammatical variations thereof refer to bringing two or more materials into close enough proximity that they can interact. Thus, for illustrative purposes only, a compound of the present invention can contact a melanocyte by, for example, interacting with a receptor on the surface of the melanocyte. Similarly, a composition of the present invention can contact a human subject by, for example, being applied directly to the subject's skin.

As used herein, a "subject" means a mammalian cell, tissue, organism, or populations thereof. Subjects of the present invention are preferably human, including human cells, tissues, and beings, but otherwise include, primates, farm animals, domestic animals, laboratory animals, and the like. Some examples of agricultural animals include cows, pigs, horses, goats, and the like. Some examples of domestic animals include dogs, cats, and the like. Some examples of laboratory animals include primates, rats, mice, rabbits, guinea pigs, and the like.

As used herein, a subject "in need" of improvement in hyperpigmentation caused by a hyperpigmentation disorder includes subjects with a real or perceived need of improvement.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "prevent," "preventing," "prevention," and grammatical variations thereof mean that the compounds of the present invention are useful when administered to a patient who has not been diagnosed as possibly having the disorder or disease at the time of administration, but who would normally be expected to develop the disorder or disease or be at increased risk for the disorder or disease. The compounds and compositions of the invention, for example, slow the development of the disorder or disease symptoms, delay the onset of the disorder or disease, or prevent the individual from developing the disorder or disease at all. Preventing also includes administration of the compounds of the invention to those individuals thought to be predisposed to the disorder or disease due to age, familial history, genetic or chromosomal abnormalities, and/or due to the presence of one or more biological markers for the disorder or disease.

As used herein, the term "promote" and grammatical variations thereof mean to allow, enhance, permit, facilitate, foster, encourage, induce, or otherwise help to bring about.

As used herein, the term "produce" and grammatical variations thereof mean to cause a particular result to happen, occur, or come into existence. By non-limiting example, the compounds and compositions of the present invention produce a photoprotective or UV-protective effect in a subject.

As used herein, the term "erythema" refers to redness of the skin. Erythema may be caused by dilation and/or irritation of the superficial capillaries. The term "UV-induced erythema" refers to skin redness that develops as a result of UV exposure. As used herein, "sunburn" and grammatical variations thereof refers to UV-induced erythema caused by exposure to sunlight or artificial UV sources (e.g. tanning beds).

As used herein, the term "hyperpigmentation" refers generally to an area of skin wherein the pigmentation is greater than that of an adjacent area of skin (e.g. a pigment spot, age spot, mole, and the like). Hyperpigmentation of the present invention includes, but is not limited to, regional hyperpigmentation by melanocytic hyperactivity, other localized hyperpigmentation by benign melanocytic hyperactivity and proliferation, disease-related hyperpigmentation, and accidental hyperpigmentations such as those due to photosensitization, genetic makeup, chemical ingestion, or other exposure (e.g. UV exposure), age, and post-lesional scarring. As used herein, "UV-induced hyperpigmentation" refers to any hyperpigmentation caused by exposure to natural or artificial UV.

As used herein, the term "hypopigmentation" refers generally to an area of skin wherein the pigmentation is less than that of an adjacent area of skin. Hypopigmentation of the present invention includes, but is not limited to, vitiligo, depigmentation, *Pityriasis alba*, focal hypopigmentation, post-inflammatory hypopigmentation, piebaldism, albinism, *Tinea versicolor*, photosensitivity, leucism, hypomelanosis, atopic dermatitis, psoriasis, and the like.

As used herein, "UV-induced skin damage" means skin damage resulting from exposure to UV, including UVA, UVB, and UVC. UV-induced skin damage of the present invention includes, but is not limited to, wrinkles, hyperpigmentation, dysplasias, actinic keratosis, and skin cancers.

As used herein, "UV-induced aging of the skin" means skin aging resulting from exposure to UV, including UVA, UVB, and UVC. UV-induced skin aging of the present invention manifests itself as, for example, wrinkles, fine lines, age spots, moles, dryness, thinness, or reduced elasticity of the skin, uneven skin tone, and other reductions in skin radiance, texture, resiliency, firmness, sagginess, and clarity caused, in whole or in part, by UV exposure.

As used herein, the term "photoprotective" and grammatical variations thereof, when used to describe the effects of the compounds and compositions of the present invention, mean that the compound and compositions described herein prevent and/or mitigate damage caused by light, particularly sunlight. Likewise, "photoprotective agents" of the present invention are those compounds and compositions described herein that prevent and/or mitigate damage caused by light, particularly sunlight.

As used herein, the term "UV-protective" and grammatical variations thereof, when used to describe the effects of the compounds and compositions of the present invention, mean that the compound and compositions described herein prevent and/or mitigate damage caused by ultraviolet ("UV") light. Likewise, "UV-protective agents" of the present invention are those compounds and compositions described herein that prevent and/or mitigate damage caused by UV. Ultraviolet light of the present invention includes, for example, UVA (320-240 nm), UVB (290-320 nm), and UVC (200-290 nm).

As used herein, the term "filter" and grammatical variations thereof mean to block, reflect, absorb, or scatter UV. "Sunscreening agents" of the present invention include all compounds and compositions of the present invention that block, reflect, absorb, or scatter UV.

As used herein, the term "absorb" and grammatical variations thereof mean to take in UV or convert UV into heat energy. By non-limiting example, compounds and compositions of the present invention can absorb UV and, as a result, radiate heat energy into their surroundings.

As used herein, the term "reflect" and grammatical variations thereof, when used in the context of UV, mean to throw or bounce UV back without absorbing it.

As used herein, the term "composition" means an entity comprising one or more compounds of the present invention, as well as any entity which results, directly or indirectly, from combinations of one or more compounds of the present invention with other ingredients. Compositions of the present invention can be used as, for example, in vifro or in vivo research reagents. Compositions of the present invention can also be applied directly to the skin of a human or non-human subject for a cosmetic or pharmaceutical effect. Additionally, compositions of the present invention comprise one or more of the compounds listed in Table 1 or FIG. 3, or a chemical analog, crystalline form, hydrate, or pharmaceutically or cosmetically acceptable salt thereof.

A composition of the present invention may be administered in any desired and effective manner for both in vifro and in vivo applications: for oral ingestion or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition of the present invention may be administered in conjunction with other compositions. A composition of the present invention may be encapsulated or otherwise protected against gastric or other secretions, if desired.

The compositions of the invention comprise one or more active ingredients in admixture with one or more cosmetically or pharmaceutically acceptable carriers and, optionally, one or more other compounds, ingredients and/or materials. Regardless of the route of administration selected, the compounds and compositions of the present invention are formulated into cosmetically or pharmaceutically acceptable dosage forms by conventional methods known to those of skill in the art.

Cosmetically or pharmaceutically acceptable vehicles, diluents and carriers are well known in the art and include materials suitable for contact with the tissues of humans and non-humans without undue toxicity, incompatibility, instability, irritation, allergic response and the like. Cosmetically or pharmaceutically acceptable vehicles, diluents and carriers include any substantially non-toxic substance conventionally usable, for example, for topical, oral, peritoneal, or subcutaneous administration of cosmetics or pharmaceuticals in which the compounds and compositions of the present invention will remain stable and bioavailable when applied, ingested, injected, or otherwise administered to a human or non-human subject. Cosmetically or pharmaceutically acceptable carriers suitable for topical application are known to those of skill in the art and include cosmetically or pharmaceutically acceptable liquids, creams, oils, lotions, ointments, gels, or solids, such as conventional cosmetic night creams, foundation creams, suntan lotions, sunscreens, hand lotions, make-up and make-up bases, masks and the like. Carriers suitable for a selected dosage form and intended route of administration are well known in the art, and acceptable carriers for a chosen dosage form and method of administration can be determined using ordinary skill in the art.

The compositions of the present invention can contain other ingredients conventional in cosmetics including perfumes, estrogen, Vitamins A, C and E, alpha-hydroxy or alpha-keto acids such as pyruvic, lactic or glycolic acids, lanolin, vaseline, aloe vera, methyl or propyl paraben, pigments and the like. Non-limiting cosmetically or pharmaceutically acceptable vehicles, diluents and carriers of the present invention include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, and the like.

The compositions of the invention may, optionally, contain additional ingredients and/or materials commonly used in cosmetic compositions. These ingredients and materials are well known in the art and include, for example, (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocathons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more cosmetically or pharmaceutically acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the cosmetic formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include cosmetically or pharmaceutically acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions of the present invention for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions of the present invention which are suitable for vaginal administration also include pessaries, tampons, creams, gels, pastes, foams or spray formulations containing such cosmetically or pharmaceutically acceptable carriers as are known in the art to be appropriate.

Dosage forms for the topical or transdermal administration include powders, sprays, ointments, pastes, creams, lotions, gels, solutions, patches, drops, emulsions, suspensions, aerosols, and inhalants. Any desired conventional vehicles, assistants and optionally further active ingredients may be added to the formulation.

Preferred assistants originate from the group comprising preservatives, antioxidants, stabilisers, solubilisers, vitamins, colorants, odour improvers, film formers, thickeners and humectants.

Solutions and emulsions can comprise the conventional vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, groundnut oil, maize oil, olive oil, castor oil and sesame oil, glycerol fatty acid esters, polyethylene glycols and fatty acid esters of sorbitan, or mixtures of these substances.

The emulsions may exist in various forms. Thus, they can be, for example, an emulsion or microemulsion of the water-in-oil (W/O) type or of the oil-in-water (O/W) type, or a multiple emulsion, for example of the water-in-oil-in-water (W/O/W) type.

The compositions according to the invention may also be in the form of emulsifier-free, disperse preparations. They can be, for example, hydrodispersions or Pickering emulsions.

Suspensions may comprise conventional vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Pastes, ointments, gels and creams may comprise conventional vehicles, for example animal and vegetable fats, waxes, paraffins, starch, tragacanth, cellulose derivatives, polyethylene glycols, silicones, bentonites, silicic acid, talc and zinc oxide, or mixtures of these substances.

Face and body oils may comprise the conventional vehicles, such as synthetic oils, such as fatty acid esters, fatty alcohols, silicone oils, natural oils, such as vegetable oils and oily plant extracts, paraffin oils, lanolin oils, or mixtures of these substances.

Sprays may comprise the conventional propellants, for example chlorofluorocarbons, propane/butane or dimethyl ether.

Compositions of the present invention suitable for parenteral administrations comprise one or more compounds in combination with one or more cosmetically or pharmaceutically acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable cosmetic form may be brought about by the inclusion of agents which delay absorption.

In some cases, in order to prolong the effect, it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered composition may be accomplished by dissolving or suspending the active composition in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The compositions of the present invention may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

In the present invention, the term “crystalline form” means the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

The term “hydrate”, as used herein, means a solid or a semi-solid form of a chemical compound containing water in a molecular complex. The water is generally in a stoichiometric amount with respect to the chemical compound.

As used herein, “cosmetically or pharmaceutically acceptable salt” refers to a derivative of the compounds disclosed herein wherein the compounds are modified by making acid or base salts thereof. Examples of cosmetically or pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2,2',2"-nitrilotris(ethanol)), trometh-amine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further cosmetically or pharmaceutically acceptable salts can be formed with cations from metals like aluminum, calcium, lithium, magnesium, potassium, sodium, zinc and the like.

The cosmetically or pharmaceutically acceptable salts of the present invention can be synthesized from a compound disclosed herein which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

It is envisioned that the compounds and compositions of the present invention may be included in cosmetic or pharmaceutical compositions for both in vitro and in vivo applications.

It is envisioned that the compounds and compositions of the present invention, including one or more compounds listed in Table 1 or FIG. 3, or a chemical analog, crystalline form, hydrate, or pharmaceutically or cosmetically acceptable salt thereof, may be co-administered to a subject to effectuate the skin pigmentation-modulating purposes of the present invention.

It is also envisioned that the compositions of the present invention may comprise one or more compounds listed in Table 1 or FIG. 3, or a chemical analog, crystalline form, hydrate, or pharmaceutically or cosmetically acceptable salt thereof. For example, a composition of the present invention may comprise indirubin or chemical analogs thereof in combination with malassezin or chemical analogs thereof.

Additionally, it is envisioned that the compounds of the present invention include compounds produced by *Malassezia*, or a chemical analog, crystalline form, hydrate, or pharmaceutically or cosmetically acceptable salt thereof. Further, it is envisioned that the compositions and methods of the present invention may involve one or more compounds produced by *Malassezia*, or a chemical analog, crystalline form, hydrate, or pharmaceutically or cosmetically acceptable salt thereof. For example, compounds produced by, or derived from, *Malassezia* include, but are not limited to, the compounds shown in FIG. 3.

It is further envisioned that the methods of the present invention may involve co-administering two or more compounds and/or compositions of the present invention to effectuate the skin pigmentation-modulating purposes described herein.

Co-administered compounds and compositions of the present invention may, for example, contact a subject at substantially the same time or one after another.

The compositions of the present invention containing one or more *Malassezia*-derived compounds or chemical analogs thereof may demonstrate synergistic effects over component compounds alone on various efficacy criteria, including, but not limited to, mean tissue viability, melanin concentration, skin brightening, skin darkening, induction of melanocyte apoptosis, and modulation of arylhydrocarbon (AhR) activity, melanogenesis, or melanin concentration.

The terminology used herein is for the purpose of describing particular embodiments only and is not intended to be limiting. As used in the specification and the appended claims, the singular forms “a,” “an,” and “the” include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6,9, and 7.0 are explicitly contemplated.

The following examples are provided to further illustrate the methods of the present invention. These examples are illustrative only and are not intended to limit the scope of the invention in any way.

EXAMPLES

Example 1

Compound Designations

Table 1 below shows structures and names for compounds of the instant invention.

TABLE 1

| Compound Code | Compound Name | Structure |
|---|---|---|
| CV-8684 | Malassezin | 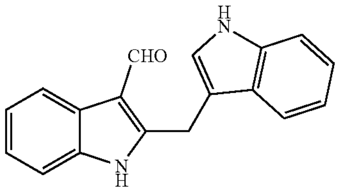 [SMILES: O=Cc1c(Cc2c[nH]c3ccccc23)[nH]c2ccccc12] |

TABLE 1-continued
| Compound Code | Compound Name | Structure |
|---|---|---|
| N/A | Malassezin Precursor | 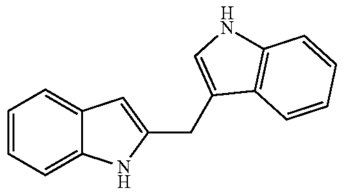 [SMILES: c1ccc2[nH]c(Cc3c[nH]c4ccccc34)cc2c1] |
| CV-8685 | Indolo[3,2-b] carbazole | 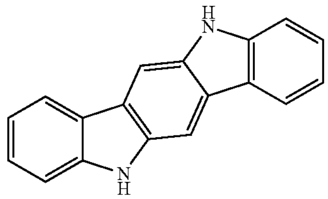 [SMILES: c1ccc2c(c1)[nH]c1cc3c(cc12)[nH]c1ccccc13] |
| CV-8686 | Compound I | 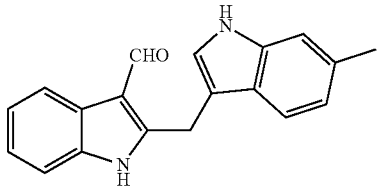 [SMILES: Cc1ccc2c(Cc3[nH]c4ccccc4c3C=O)c[nH]c2c1] |
| CV-8687 | Compound IV | 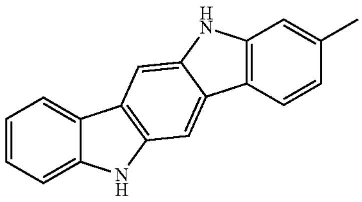 [SMILES: Cc1ccc2c(c1)[nH]c1cc3c(cc12)[nH]c1ccccc13] |
| CV-8688 | Compound II | 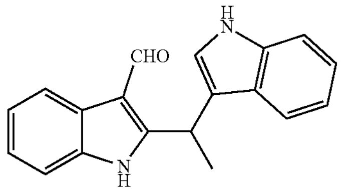 [SMILES: CC(c1[nH]c2ccccc2c1C=O)c1c[nH]c2ccccc12] |
| CV-8802 | Compound C | 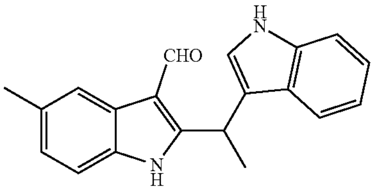 [SMILES: Cc1ccc2[nH]c(C(C)c3c[nH]c4ccccc34)c(C=O)c2c1] |
| CV-8803 | Compound K | 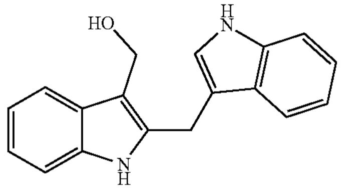 [SMILES: OCc1c(Cc2c[nH]c3ccccc23)[nH]c2ccccc12] |

TABLE 1-continued
| Compound Code | Compound Name | Structure |
|---|---|---|
| CV-8804 | Compound A | 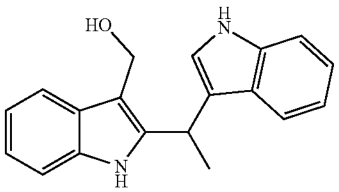 [SMILES: CC(c1[nH]c2ccccc2c1CO)c1c[nH]c2ccccc12] |
| AB12508 | Compound E | 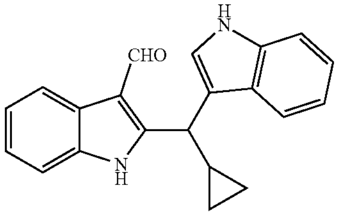 [SMILES: O=Cc1c(C(c2c[nH]c3ccccc23)C2CC2)[nH]c2ccccc12] |
| CV-8819 | Compound A5 | 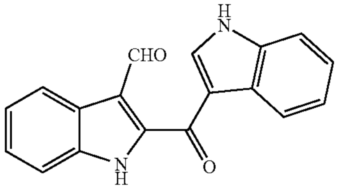 [SMILES: O=Cc1c(C(=O)c2c[nH]c3ccccc23)[nH]c2ccccc12] |
| AB12509 | Compound H | 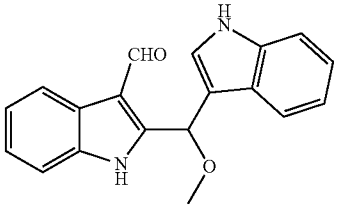 [SMILES: COC(c1[nH]c2ccccc2c1C=O)c1c[nH]c2ccccc12] |
| CV-8877 | Compound B | 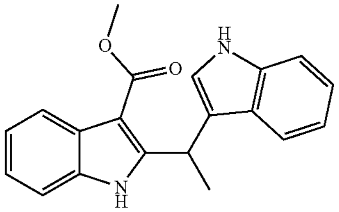 [SMILES: COC(=O)c1c(C(C)c2c[nH]c3ccccc23)[nH]c2ccccc12] |
| N/A | Compound B10 | 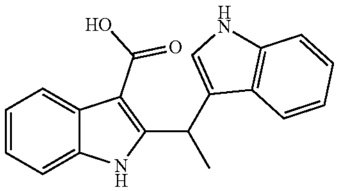 [SMILES: CC(c1[nH]c2ccccc2c1C(=O)O)c1c[nH]c2ccccc12] |
| AB11644 | N/A | 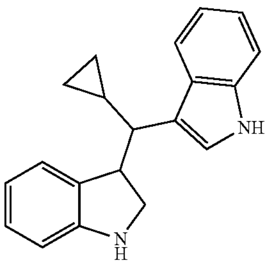 [SMILES: c1ccc2c(c1)NCC2C(c1c[nH]c2ccccc12)C1CC1] |

TABLE 1-continued
| Compound Code | Compound Name | Structure |
|---|---|---|
| AB12976 | O52 | 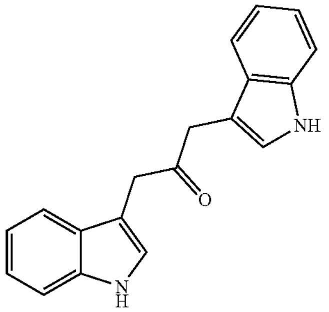 [SMILES: O=C(Cc1c[nH]c2ccccc12)Cc1c[nH]c2ccccc12] |
| AB17011 | Malassezia Indole A | 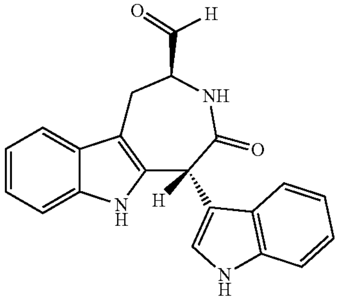 [SMILES: O=C[C@@H]1Cc2c([nH]c3ccccc23)[C@@H](c2c[nH]c3ccccc23)C(=O)N1] |
| AB17014 | Pityriacitrin | 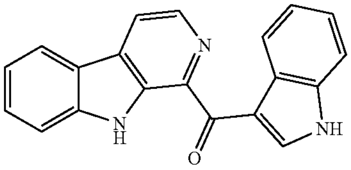 [SMILES: O=C(c1c[nH]c2ccccc12)c1nccc2c1[nH]c1ccccc12] |
| AB17151 | N/A | 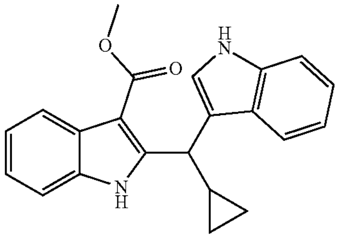 [SMILES: COC(=O)c1c(C(c2c[nH]c3ccccc23)C2CC2)[nH]c2ccccc12] |
| AB17225 | Compound IV | 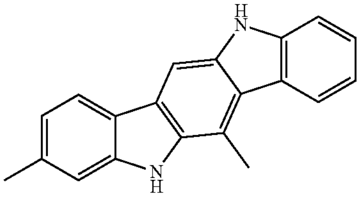 [SMILES: Cc1ccc2c(c1)[nH]c1c(C)c3c(cc12)[nH]c1ccccc13] |
| AB17227 | Malassezialactic Acid | 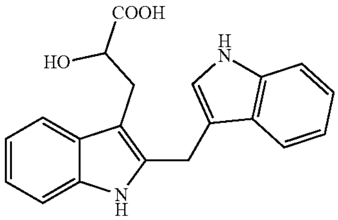 [SMILES: O=C(O)C(O)Cc1c(Cc2c[nH]c3ccccc23)[nH]c2ccccc12] |

TABLE 1-continued
| Compound Code | Compound Name | Structure |
|---|---|---|
| AB12507 | N/A | 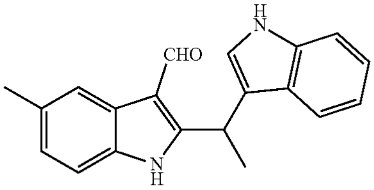 [SMILES: Cc1ccc2[nH]c(C(C)c3c[nH]c4ccccc34)c(C=O)c2c1] |
| AB17219 | Compound V | 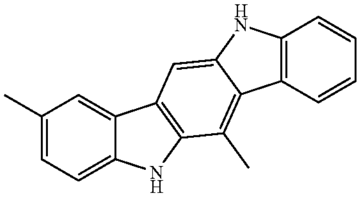 [SMILES: Cc1ccc2[nH]c3c(C)c4c(cc3c2c1)[nH]c1ccccc14] |
| N/A | FICZ | 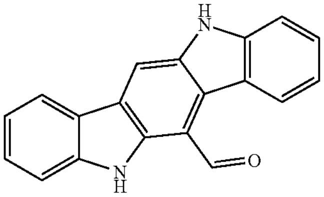 [SMILES: O=Cc1c2[nH]c3ccccc3c2cc2[nH]c3ccccc3c12] |
| AB17220 | Compound VIII | 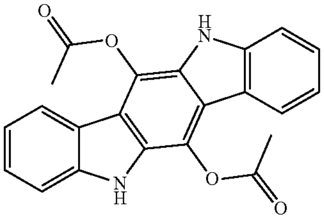 [SMILES: CC(=O)Oc1c2[nH]c3ccccc3c2c(OC(C)=O)c2[nH]c3ccccc3c12] |
| AB17221 | Compound VII | 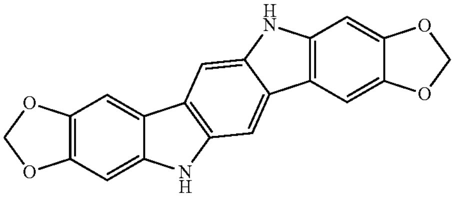 [SMILES: c1c2c(cc3c1[nH]c1cc4c(cc13)[nH]c1cc3c(cc14)OCO3)OCO2] |
| N/A | Indirubin | 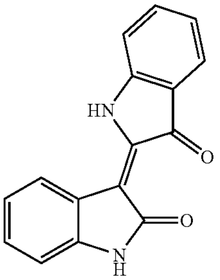 [SMILES: O=C1Nc2ccccc2/C1=C1\Nc2ccccc2C1=O] |
| AB17590 | N/A | 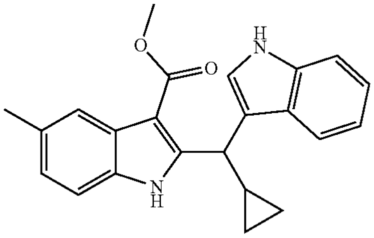 [SMILES: COC(=O)c1c(C(c2c[nH]c3ccccc23)C2CC2)[nH]c2ccc(C)cc12] |

TABLE 1-continued
| Compound Code | Compound Name | Structure |
|---|---|---|
| AB17653 | N/A | 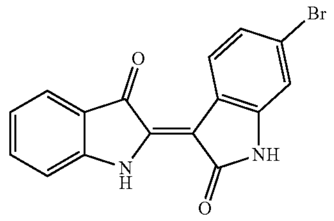 [SMILES: O=C1Nc2cc(Br)ccc2/C1=C1/Nc2ccccc2C1=O] |
| AB17654 | N/A | 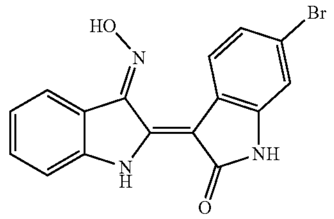 [SMILES: O=C1Nc2cc(Br)ccc2/C1=C1/Nc2ccccc2/C1=N\O] |
| AB17655 | N/A | 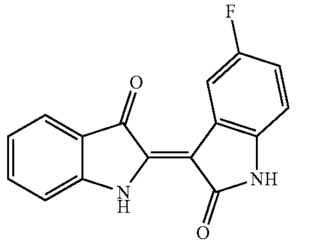 [SMILES: O=C1Nc2ccc(F)cc2/C1=C1/Nc2ccccc2C1=O] |
| AB17656 | N/A | 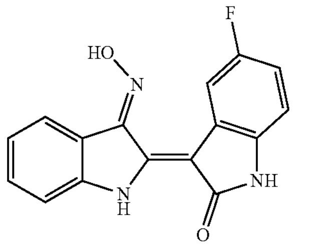 [SMILES: O=C1Nc2ccc(F)cc2/C1=C1/Nc2ccccc2/C1=N\O] |
| AB17657 | N/A | 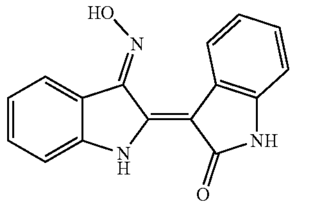 [SMILES: O=C1Nc2ccccc2/C1=C1/Nc2ccccc2/C1=N\O] |
| AB17658 | N/A | 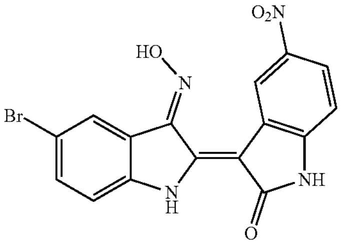 [SMILES: O=C1Nc2ccc([N+](=O)[O-])cc2/C1=C1/Nc2ccc(Br)cc2/C1=N\O] |

TABLE 1-continued

| Compound Code | Compound Name | Structure |
| --- | --- | --- |
| N/A | Compound C1 | 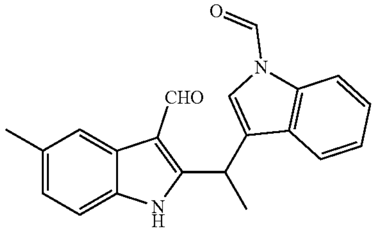 [SMILES: Cc1ccc2[nH]c(C(C)c3cn(C=O)c4ccccc34)c(C=O)c2c1] |
| N/A | Compound C2 | 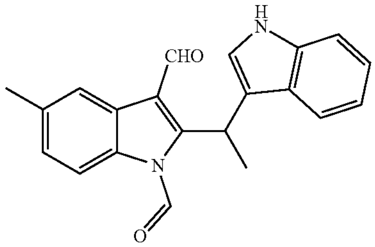 [SMILES: Cc1ccc2c(c1)c(C=O)c(C(C)c1c[nH]c3ccccc13)n2C=O] |

Example 2

Apoptosis-Inducing Activity of Indirubin and Indirubin Derivatives

Reagents

Alexa Fluor 488 Annexin V/Dead Cell Apoptosis Kit, Fetal Bovine Serum (FBS), 0.25% Trypsin-EDTA (lx), Caspase-Glo 3/7 Assay, RPMI 1640 Medium, Dulbecco's Modified Eagle Medium, and Antibiotic Antimycotic Solution (100×).

The cell lines MeWo (ATCC® HTB-65™), WM115 (ATCC® CRL-1675) and B16F1 (ATCC® CRL-6323) are maintained in the following culture media: culture medium for MeWo and B16F1: DMEM supplemented with 10% FBS; culture medium for WM115: RPMI 1640 supplemented with 10% FBS.

Experimental Methods

Cells are harvested and the cell number determined using a Countess Cell Counter. The cells are diluted with culture medium to the desired density. The final cell density may be, for example, 4,000 cells/well for 6 hr and 24 hr treatment, and 2,000 cells/well for 48 hr and 72 hr treatment. For the Annexin V assay, 384-well clear-bottom plates (Corning 3712) are employed, whereas 384-well solid white-bottom plates (Corning 3570) are used for the Caspase-Glo assays. All plates are covered with a lid and placed at 37° C. and 5% $CO_2$ overnight for cell attachment.

Test compounds are dissolved in DMSO to 30 mM stock. 10-fold dilutions are performed to generate 3 mM and 0.3 mM concentrations. 0.9 mM Staurosporine is employed as positive control, and DMSO is employed as negative control (NC). 132.5 nL of compounds is transferred from compound source plate to 384-well cell culture plate(s) using liquid handler Echo550. After the indicated incubation time, the plates are removed from the incubator for detection.

For the Annexin V assay, plates are removed from the incubator and culture media is removed. Cells are washed twice with 40 uL PBS and 15 uL of pre-mixed Annexin V-FITC and Hoechst 33342 dye working solution are added per well. Plates are incubated at room temperature for 20 minutes, sealed, and centrifuged for 1 minute at 1,000 rpm to remove bubbles. Plates are read using ImageXpress Nano.

For the Caspase-Glo assay, plates are removed from the incubator and equilibrated at room temperature for 15 minutes. Caspase-Glo 3/7 reagents also are thawed and equilibrated to room temperature before the experiment. Caspase-Glo reagent is added to the required wells at 1:1 ratio to the culture medium. Plates are incubated at room temperature for 15 minutes and read using EnSpire™ plate reader. Fold induction is calculated according to the following formula: Fold induction=$Lum_{Sample}/Lum_{NC}$.

Annexin V Assay and Caspase 3/7 Assay Results

It is expected that the compounds and compositions of the present invention, including indirubin and chemical analogs thereof, will induce cell death. Chemical analogs of indirubin are expected to exhibit, for example, more potent apoptosis-inducing activity compared to indirubin. Likewise, certain chemical analogs of indirubin are expected to demonstrate, for example, less effective apoptosis-inducing activity compared to indirubin. Such compounds may have more favorable toxicity profiles compared to more potent compounds.

Example 3

Cell Viability After Exposure to Indirubin and Indirubin Derivatives

Reagents

CellTiter-Glo® 2.0 assay.

Experimental Methods

For the CellTiter-Glo assay, test compounds are prepared in 10 mM DMSO solution. Compounds are serially diluted into 12 concentrations. 40 uL of cells from a 100,000 cell/mL suspension are dispensed into each well of a 384-well plate (Corning 3570). Plates are incubated overnight at 37° C., 5% $CO_2$, and 95% humidity. Test compounds are added, with DMSO as vehicle control. Plates are incubated at 37° C., 5% $CO_2$, and 95% humidity for 6, 24, or 48 hours, and 40 uL of CellTiter-Glo reagent is added to the wells to assess cell viability.

Results

It is expected that the compounds and compositions of the present invention, including indirubin and chemical analogs thereof, will induce cell death. Chemical analogs of indirubin are expected to exhibit, for example, more potent apoptosis-inducing activity compared to indirubin. Likewise, certain chemical analogs of indirubin are expected to demonstrate, for example, less effective apoptosis-inducing activity compared to indirubin. Such compounds may have more favorable toxicity profiles compared to more potent compounds.

Example 4

Arylhydrocarbon Receptor Activation Potential of Indirubin and Indirubin Derivatives Assay Procedures Culture media for stably transfected HepG2 cells is prepared by supplementing DMEM with high glucose and L-glutamine, as well as 10% FBS.

HepG2-AhR-Luc cells are cultured in T-75 flasks at 37° C., 5% $CO_2$, and 95% relative humidity. Cells are allowed to reach 80-90% confluence before detachment and splitting.

Cultivated cells are rinsed with 5 mL PBS. PBS is aspirated away, 1.5 mL trypsin is added to the flask, and cells are incubated at 37° C. for approximately 5 minutes or until the cells are detached and float. Trypsin is inactivated by adding excess serum-containing media.

The cell suspension is transferred to a conical tube and centrifuged at 120 g for 10 minutes to pellet the cells. Cells are resuspended in seeding media at a proper density. 40 μL of cells are transferred to a 384-well culture plate ($5\times10^3$ cells/well). Plates are placed in the incubator at 37° C. for 24 hours.

Afterward, stock solutions of test compounds and omeprazole positive control are prepared. Compound solutions are transferred into the assay plate using Echo550. The plate is then placed back into the incubator for compound treatment.

Later, after 24 hours of treatment, the plate is removed from the incubator and allowed to cool at ambient temperature. 30 μL One-Glo reagent equal to that of the culture medium is added in each well. Cells are allowed to lyse for at least 3 minutes, and then measured in a luminometer.

Dose responses are graphed using the non-linear regression analysis in XLfit, and $EC_{50}$ values are also calculated.

Results

It is expected that the compounds and compositions of the present invention, including indirubin and chemical analogs thereof, will modulate AhR activity. Chemical analogs of indirubin are expected to exhibit, for example, more potent AhR agonist activity compared to indirubin. Likewise, certain chemical analogs of indirubin are expected to demonstrate, for example, less effective AhR agonist activity compared to indirubin.

Example 5

MelanoDerm™ Assays

The purpose of this study was to evaluate the potential action of the test articles as a skin melanogenesis modulator in the MelanoDerm™ Skin Model after repeated test article exposures. Secondarily, the purpose of this study was to evaluate the potential dermal irritation of the test article to the MelanoDerm™ Skin Model after repeated exposures. Toxicity was determined by measuring the relative conversion of MTT (3-[4,5-dimethylthiazol-2-yl]-2,5-diphenyltetrazolium bromide) in the test article-treated tissues compared to the negative/solvent control-treated tissues. The potential impact on melanin production was determined by measuring the concentration of melanin produced by the test article-treated tissues compared to the negative/solvent control-treated tissues.

Identification of Test Substances and Assay Controls

TABLE 2

| Test Articles Tested in Diluted Form | | | |
|---|---|---|---|
| Test Article Designation | Sponsor Designation | Dosing Concentration | Preparation Instructions |
| 17AA70 | DMSO (solvent control) | 0.5% (v/v) | The test article was diluted (v/v) with EPI-100-LLMM to a final concentration of 0.5%; the diluted test article was vortexed for at least 1 minute and dosed onto the tissues using a dosing volume of 25 μL. A total volume of ~0.5 mL was prepared for each tissue treatment. |
| 17AD45 | Compound K (CV-8803) | 500 μM | Starting from the stock concentration provided, the test article was diluted (v/v) with EPI-100-LLMM to the final concentration of 500 μM. The test article dilution was vortexed for at least 1 minute, heated at 37° ± 1° C. (in a water bath) for 15 minutes, vortexed again for at least 1 minute and dosed on the tissues using a dosing volume of 25 μL. A total volume of ~0.5 mL was prepared for each tissue treatment. |
| 17AJ41 | Malassezin (CV-8684) | 500 μM | |
| 17AJ43 | Compound B (CV-8877) | 500 μM | |
| 17AJ44 | Compound E (AB12508) | 500 μM | |
| 18AA14 | AB17151 | 500 μM | |
| 18AD42 | Indirubin | 500 μM | Starting from the solid material provided, a stock solution of ~100 mM was prepared in DMSO. The stock dilution was stored at −15° C. to −25° C. From the stock concentrations thus prepared, the test article was further diluted with EPI-100-LLMM to the final concentration of 500 μM. The |

TABLE 2-continued

Test Articles Tested in Diluted Form

| Test Article Designation | Sponsor Designation | Dosing Concentration | Preparation Instructions |
|---|---|---|---|
| | | | test article dilution was vortexed for at least 1 minute, heated at 37° ± 1° C. (in a water bath) for 15 minutes, vortexed again for at least 1 minute and dosed on the tissues using a dosing volume of 25 µL. A total volume of ~0.5 mL was prepared for each tissue treatment. |

TABLE 3

Test Articles Tested As Combinations

| Test Article Designation | Sponsor Designation | Dosing Concentration | Preparation Instructions |
|---|---|---|---|
| 17AJ41 | Malassezin (CV-8684) | 250 µM | A total volume of ~1.0 mL of the combined test article was prepared for each tissue treatment as |
| 18AD42 | Indirubin | 250 µM | follows:<br>2 µL of 17AJ41 (100 mM)<br>2 µL of 18AD42 (100 mM)<br>796 µL of EPI-100-LLMM<br>The test article combination was vortexed for at least 1 minute, heated at 37° ± 1° C. (in a water bath) for 15 minutes, vortexed again for at least 1 minute and dosed on the tissues using a dosing volume of 25 µL. |
| 18AD42 | Indirubin | 250 µM | A total volume of ~1.0 mL of the combined |
| 18AA14 | AB17151 | 250 µM | test article was prepared for each tissue treatment as follows:<br>2 µL of 18AD42 (100 mM)<br>2 µL of 18AA14 (100 mM)<br>796 µL of EPI-100-LLMM<br>The test article combination was vortexed for at least 1 minute, heated at 37° ± 1° C. (in a water bath) for 15 minutes, vortexed again for at least 1 minute and dosed on the tissues using a dosing volume of 25 µL. |
| 17AJ44 | Compound E (AB12508) | 100 µM | A total volume of ~1.0 mL of the combined test article was prepared for each tissue |
| 17AJ43 | Compound B (CV-8877) | 100 µM | treatment as follows:<br>1 µL of 17AJ44 (100 mM)<br>1 µL of 17AJ43 (100 mM)<br>998 µL of EPI-100-LLMM<br>The test article combination was vortexed for at least 1 minute, heated at 37° ± 1° C. (in a water bath) for 15 minutes, vortexed again for at least 1 minute and dosed on the tissues using a dosing volume of 25 µL. |
| 17AJ43 | Compound B (CV-8877) | 100 µM | A total volume of ~1.0 mL of the combined test article was prepared for each tissue |
| 18AA14 | AB17151 | 100 µM | treatment as follows:<br>1 µL of 17AJ43 (100 mM)<br>1 µL of 18AA14 (100 mM)<br>998 µL of EPI-100-LLMM<br>The test article combination was vortexed for at least 1 minute, heated at 37° ± 1° C. (in a water bath) for 15 minutes, vortexed again for at least 1 minute and dosed on the tissues using a dosing volume of 25 µL. |

Assay controls include: positive control—1% Kojic Acid; negative control—sterile, deionized water; and solvent control—DMSO (dimethyl sulfoxide) prepared in EPI-100-LLMM.

For this study, a negative control was not used. Instead, the solvent control (17AA70) was used to correct the data pertaining to the positive control- and test article-treated tissues, respectively.

Additionally, the test article and controls were applied to groups of 4 tissues of which 2 were used for the Tissue Viability (MTT) endpoint and 2 for the Melanin endpoint, respectively.

Test System

The MelanoDerm™ Skin Model provided by MatTek Corporation (Ashland, MA) was used in this study. The MelanoDerm™ tissue consists of normal, human-derived epidermal keratinocytes (NHEK) and melanocytes (NHM)

which have been cultured to form a multilayered, highly differentiated model of the human epidermis. The NHMs within co-cultures undergo spontaneous melanogenesis leading to tissues of varying levels of pigmentation. The cultures were grown on cell culture inserts at the air-liquid interface, allowing for topical application of skin modulators. The MelanoDerm™ model exhibits in vivo-like morphological and ultrastructural characteristics. NHM localized in the basal cell layer of MelanoDerm™ tissue are dendritic and spontaneously produce melanin granules which progressively populate the layers of the tissue. Thus the test system is used to screen for materials which may inhibit or stimulate the production of melanin relative to the negative controls.

Experimental Design and Methodology

The experimental design of this study consisted of the determination of the pH of the neat test article if possible (and/or dosing solution as appropriate) and a definitive assay to determine the relative tissue viability and the potential action of the test article as a skin melanogenesis modulator to MelanoDerm™ Skin Model after repeated exposures. The test articles were exposed to the MelanoDerm™ Skin Model for a total of 7 days. The test articles were topically applied to the MelanoDerm™ Skin Model every 48 hours (within a timeframe of 48+2 hours from previous treatment). The toxicity of the test articles were determined by the NAD(P)H-dependent microsomal enzyme reduction of MTT (and, to a lesser extent, by the succinate dehydrogenase reduction of MTT) in control and test article-treated tissues. Data was presented in the form of relative survival (MTT conversion relative to the negative/solvent control). The potential impact on melanin production was evaluated by determining the concentration of melanin produced in the test article-treated tissues compared to the negative/solvent control-treated tissues. Data was presented in the form of concentration of melanin produced by the test article-treated tissues determined using a melanin standard curve. Alternatively, data may be presented as percent change in melanin concentration relative to the negative/solvent control-treated tissues.

The methods used are a modification of the procedures supplied by MatTek Corporation.

Media and Reagents

MelanoDerm™ Maintenance Medium (EPI-100-LLMM) was purchased from MatTek Corporation. MelanoDerm™ Skin Model (MEL-300-A) was purchased from MatTek Corporation. 1% Kojic acid (prepared in sterile, deionized water) was purchased from Sigma MTT (3-[4,5-dimethylthiazol-2-yl]-2,5-diphenyltetrazolium bromide) was purchased from Sigma. Dulbecco's Modified Eagle's Medium (DMEM) containing 2 mM L-glutamine (MTT Addition Medium) was purchased from Quality Biological. Extraction Solvent (Isopropanol) was purchased from Aldrich. Sterile Ca++ and Mg++ Free Dulbecco's Phosphate Buffered Saline (CMF-DPBS) was purchased from Invitrogen. Melanin was purchased from Sigma. Sterile deionized water was purchased from Quality Biological. Solvable was purchased from Perkin Elmer.

Preparation and Delivery of Test Article

Unless otherwise specified within this protocol, twenty five microliters of each test article were applied directly on the tissue so as to cover the upper surface. Depending on the nature of the test article (liquids, gels, creams, foams, etc.), the use of a dosing device, mesh or other aid to allow the uniform spreading of the test article over the surface of the tissue may have been necessary.

Route of Administration

The test articles were applied topically to the MelanoDerm™ tissue every 48 hours (within a timeframe of 48+2 hours from previous treatment) during a 7-day trial. Twenty five microliters of each test article were applied to each tissue. Twenty five microliters of the positive and negative/solvent controls, respectively, were applied to each tissue.

pH Determination

The pH of the neat liquid test article (and/or dosing solution as appropriate) was determined, if possible. The pH was determined using pH paper (for example, with a pH range of 0-14 to estimate, and/or a pH range of 5-10 to determine a more precise value). The typical pH increments on the narrower range pH paper were approximately 0.3 to 0.5 pH units. The maximum increment on the pH paper was 1.0 pH units.

Controls

The definitive assay included a negative control, a positive control and one solvent control (DMSO). The MelanoDerm™ tissues designated to the assay negative control were treated with 25 μL of sterile, deionized water. Twenty five microliters of 1% Kojic acid (prepared in sterile, deionized water and filtered at the time of preparation) was used to dose the tissues designated to the assay positive control. The 1% Kojic acid was stored in a tube covered with aluminum foil until used within 2 hours of preparation. The negative/solvent and positive control exposure times were identical to those used for the test articles. Untreated tissues were also used as controls.

Assessment of Direct Test Article Reduction of MTT

It was necessary to assess the ability of each test article to directly reduce MTT. A 1.0 mg/mL MTT solution was prepared in MTT Addition Medium. Approximately 25 μL of the test article was added to 1 mL of the MTT solution and the mixture was incubated in the dark at 37±1° C. for one to three hours. A negative control, 25 μL of sterile, deionized water, was tested concurrently. If the MTT solution color turned blue/purple, the test article was presumed to have reduced the MTT. Water insoluble test materials may have shown direct reduction (darkening) only at the interface between the test article and the medium.

Receipt of MelanoDerm™

Upon receipt of the MelanoDerm™ Skin Kit, the solutions were stored as indicated by the manufacturer. The MelanoDerm™ tissues were stored at 2-8° C. until used.

On the day of receiving (the day before dosing), an appropriate volume of MelanoDerm™ Maintenance Medium (EPI-100-LLMM) was removed and warmed to 37±1° C. Nine-tenths (0.9) mL of EPI-100-LLMM/well were aliquoted into the appropriate wells of 6-well plates. Each MelanoDerm™ tissue was inspected for air bubbles between the agarose gel and cell culture insert prior to opening the sealed package. Tissues with air bubbles greater than 50% of the cell culture insert area were not used. The 24-well shipping containers were removed from the plastic bag and the surface disinfected with 70% ethanol. An appropriate number of MelanoDerm™ tissues were transferred aseptically from the 24-well shipping containers into the 6-well plates. The MelanoDerm™ tissues were incubated at 37±1° C. in a humidified atmosphere of 5±1% $CO_2$ in air (standard culture conditions) overnight (at least 16 hours) to acclimate the tissues. Upon opening the bag, any unused tissues remaining on the shipping agar at the time of tissue transfer were briefly gassed with an atmosphere of 5% $CO_{2/95}$% air, and the bag was sealed and stored at 2-8° C. for subsequent use.

Definitive Assay

Tissue Exposure: At least 16 hours after initiating the cultures, five MelanoDerm™ tissues (considered untreated at Day 0) were photographed using a digital camera to aid in the visual assessment of the degree of pigmentation of the tissues at time zero of the assay. Two MelanoDerm™ tissues were rinsed with CMF-DPBS, blotted dry on sterile absorbent paper and cleared of excess liquid. The MelanoDerm™ tissues were transferred to the appropriate MTT containing wells after rinsing and processed in the MTT assay. Three MelanoDerm™ tissues were rinsed with CMF-DPBS, blotted dry on sterile absorbent paper and cleared of excess liquid. The MelanoDerm™ tissues were removed from the cell culture insert using sterile scalpels, placed in a labeled 1.5 mL microfuge tube, and stored at <−60° C. for subsequent melanin analysis.

At least 16 hours after initiating the cultures, the rest of the tissues were transferred on a new 6-well plate containing 0.9 mL/well of fresh, pre-warmed EPI-100-LLMM. The trial was conducted over a 7-day timeframe. Five tissues were treated topically on the first day, and every 48 hours (within a timeframe of 48+2 hours from previous treatment) with 25 µL, of each test article. The medium was refreshed daily (within a timeframe of 24+2 hours from previous refeeding); the tissues were transferred to a new 6-well plate containing 0.9 mL/well of fresh, pre-warmed EPI-100-LLMM.

Five tissues were treated topically on the first day, and every 48 hours (within a timeframe of 48+2 hours from previous treatment) with 25 µL of positive and negative/solvent controls, respectively. The medium was refreshed daily (within a timeframe of 24+2 hours from previous refeeding); the tissues were transferred to a new 6-well plate containing 0.9 mL/well of fresh, pre-warmed EPI-100-LLMM. The tissues were incubated at 37±1° C. in a humidified atmosphere of 5±1% $CO_2$ in air (standard culture conditions) for the appropriate exposure times.

On the days of dosing, the MelanoDerm™ tissue was first gently rinsed three times using ~500 µL of CMF-DPBS per rinse to remove any residual test article. The CMF-DPBS was gently pipetted into the well and then drawn off with a sterile aspirator. The tissues were transferred to a new 6-well plate containing 0.9 mL of fresh, pre-warmed EPI-100-LLMM and dosed with the appropriate test article, negative/solvent or positive control. The tissues were incubated at 37±1° C. in a humidified atmosphere of 5±1% $CO_2$ in air (standard culture conditions) for the appropriate exposure times.

At the end of the 7-day trial, the MelanoDerm™ tissues treated with the negative/solvent or positive control, and with each test article were photographed using a digital camera to aid in the visual assessment of the degree of pigmentation of the tissues at the end of the assay (Day 7). Then, the viability of two tissues treated with the positive and negative control, respectively, and with each test article, were determined by MTT reduction. At the end of the 7-day trial, the melanin produced by three tissues treated with each test article, the positive and negative/solvent control, respectively, was determined.

MTT Assay: A 10× stock of MTT prepared in PBS (filtered at time of batch preparation) was thawed and diluted in warm MTT Addition Medium to produce the 1.0 mg/mL solution no more than two hours before use. Three hundred µL of the MTT solution was added to each designated well of a prelabelled 24-well plate.

After the exposure time, each MelanoDerm™ tissue designated for the MTT assay was rinsed with CMF-DPBS (use of spray bottle acceptable for this step), blotted dry on sterile absorbent paper, and cleared of excess liquid. The MelanoDerm™ tissues were transferred to the appropriate MTT containing wells after rinsing. The 24-well plates were incubated at standard conditions for 3±0.1 hours.

After 3±0.1 hours, the MelanoDerm™ tissues were blotted on sterile absorbent paper, cleared of excess liquid, and transferred to a prelabelled 24-well plate containing 2.0 mL of isopropanol in each designated well. The plates were covered with parafilm and stored in the refrigerator (2-8° C.) until the last exposure time was harvested. If necessary, plates were stored overnight (or up to 24 hours after the last exposure time is harvested) in the refrigerator prior to extracting the MTT. Then the plates were shaken for at least 2 hours at room temperature. At the end of the extraction period, the liquid within the cell culture inserts was decanted into the well from which the cell culture insert was taken. The extract solution was mixed and 200 µL transferred to the appropriate wells of 96-well plate. Two hundred µL of isopropanol was added to the wells designated as blanks. The absorbance at 550 nm (OD550) of each well was measured with a Molecular Devices Vmax plate reader.

Melanin Assay: At the end of the appropriate exposure times, the MelanoDerm™ tissues designated for the melanin assay were gently rinsed at least three times using ~500 µL of CMF-DPBS per rinse to remove any residual test article or excess phenol red from culture medium, blotted dry on sterile absorbent paper and cleared of excess liquid. The MelanoDerm™ tissues were photographed using a digital camera at the end of the assay. The MelanoDerm™ tissues were removed from the cell culture insert using sterile scalpels or sterile punche(s), placed in a labeled 1.5 mL microfuge tube, and stored at <−60° C. for subsequent melanin analysis.

On the day of the melanin extraction assay, the excised tissues were thawed at room temperature for approximately 10 minutes. 250 µL Solvable was added to each microfuge tube and the tubes were incubated for at least 16 hours at 60+2° C. A 1 mg/mL Melanin standard stock solution was prepared by dissolving the Melanin in Solvable. A series of Melanin standards was prepared from the 1 mg/mL stock ranging from 0 mg/mL to 0.33 mg/mL. The standard series was prepared by adding 0.6 mL of the 1 mg/mL Melanin standard stock solution to 1.2 mL Solvable, and then making a series of five more dilutions (dilution factor of 3). Solvable was used as the zero standard. The Melanin standards series and the Solvable were incubated for at least 16 hours at 60+2° C.

At least 16 hours after initiating the melanin extraction, the tubes containing the samples (representing the melanin extracted from the MelanoDerm™ tissues) and the standards were cooled at room temperature and centrifuged at 13,000 rpm for 5 minutes at room temperature. 200 µL of samples (single wells) or standards (duplicate wells) were transferred to the appropriate wells of a 96-well plate. Two hundred µL of Solvable were added to the wells designated as blanks in duplicate wells. The absorbance at 490 nm (OD490) of each well was measured with a Molecular Devices Vmax plate reader (with Automix function selected).

Killed Controls for Assessment of Residual Test Article Reduction of MTT

To demonstrate that possible residual test article was not acting to directly reduce the MTT, a functional check was performed in the definitive assay to show that the test material was not binding to the tissue and leading to a false MTT reduction signal.

To determine whether residual test article was acting to directly reduce the MTT, a freeze-killed control tissue was used. Freeze killed tissue was prepared by placing untreated MelanoDerm™/EpiDerm™ (Melanoderm™ without melanocytes) tissues in the −20° C. freezer at least overnight, thawing to room temperature, and then refreezing. Once killed, the tissue may be stored indefinitely in the freezer. Freeze killed tissues may be received already prepared from MatTek Corporation, and stored in the −20° C. freezer until use. To test for residual test article reduction, killed tissues were treated with the test article in the normal fashion. All assay procedures were performed in the same manner as for the viable tissue. At least one killed control treated with sterile deionized water (negative killed control) was tested in parallel since a small amount of MTT reduction is expected from the residual NADH and associated enzymes within the killed tissue.

If little or no MTT reduction was observed in the test article-treated killed control, the MTT reduction observed in the test article-treated viable tissue may be ascribed to the viable cells. If there was appreciable MTT reduction in the treated killed control (relative to the amount in the treated viable tissue), additional steps must be taken to account for the chemical reduction or the test article may be considered untestable in this system.

Data Analysis

The mean OD550 value of the blank wells was calculated. The corrected mean OD550 value of the negative/solvent control(s) was determined by subtracting the mean OD550 value of the blank wells from their mean OD550 values. The corrected OD550 values of the individual test article exposures and the positive control exposures was determined by subtracting from each the mean OD550 value for the blank wells. All calculations were performed using an Excel spreadsheet. Although the algorithms discussed are performed to calculate the final endpoint analysis at the treatment group level, the same calculations can be applied to the individual replicates.

Corr. Test article exposure $OD_{550}$=Test article exposure $OD_{550}$−Blank mean $OD_{550}$ If killed controls (KC) were used, the following additional calculations were performed to correct for the amount of MTT reduced directly by test article residues. The raw OD550 value for the negative control killed control was subtracted from the raw OD550 values for each of the test article-treated killed controls, to determine the net OD550 values of the test article-treated killed controls.

Net OD550 for each test article KC=Raw OD550 test article KC−Raw $OD_{550}$ negative/solvent control KC The net OD550 values represent the amount of reduced MTT due to direct reduction by test article residues at specific exposure times. In general, if the net OD550 value is greater than 0.150, the net amount of MTT reduction will be subtracted from the corrected OD550 values of the viable treated tissues to obtain a final corrected OD550 value. These final corrected OD550 values will then be used to determine the % of Control viabilities.

Final Corrected OD550=Corrected test article OD550 (viable)−Net OD550 test article (KC)

Finally, the following % of Control calculations will be made:

% Viability=[(Final corrected $OD_{550}$ of Test Article or Positive Control)/(Corrected mean $OD_{550}$ of Negative/Solvent Control(s))]×100

Melanin Analysis: The raw absorbance data was captured, saved as a print-file and imported into an Excel spreadsheet. The OD490 value of each test sample (representing the melanin extracted from untreated MelanoDerm™ tissues at Day 0, MelanoDerm™ tissues treated with each test article, negative/solvent or positive controls at Day 7) and of the melanin standards was determined. The corrected OD490 value for the test samples and each melanin standard was determined by subtracting the mean OD490 value of the blank wells. The standard curve was plotted as the concentration of the standards in mg/mL (y-axis) versus the corresponding corrected absorbance. The amount of melanin in each individual tissue was interpolated from the standard curve (linear). Finally, the average of melanin concentration for each test article or control treatment groups, respectively, was calculated.

Results

FIG. 1 summarizes the mean tissue viability and melanin concentration results for the test articles, positive control, and untreated tissues. Preliminary results suggest that certain formulations applied to the carbazole compounds of the present invention may independently exhibit moderate skin brightening effects that dampen the skin darkening activity of the carbazoles.

FIG. 2 summarizes the mean tissue viability and melanin concentration results for the test articles and untreated tissues observed in a separate experiment. Combination treatments comprising, for example, malassezin and indirubin, exhibited more effective skin brightening effects than either compound on its own.

Example 6

Melanogenesis Potential of Indirubin and Indirubin Derivatives

The purpose of this study is to observe and report melanogenesis and viability of B16 melanocytes exposed to indirubin and indirubin derivatives.

Materials and Reagents

Plating media will include DMEM without L-glutamine, FBS, penicillin/streptomycin, and L-glutamine. Assay media will include DMEM without phenol red and L-glutamine, FBS, penicillin/streptomycin, L-glutamine, and aMSH. Other reagents will include Kojic Acid, DMSO, and MTT. Cells tested will be B16 cells (ATCC CRL-6475).

Protocol

B16 Melanocytes are cultured until 70% confluent and harvested. Cells are seeded in 96-well plates at a density of 4000 cells/well and are allowed to attach overnight. The following day, test articles and controls are diluted in B16 Assay media. Overnight media is aspirated and 200 ul of test articles and controls are applied. Cells are incubated at 37° C. and 10% $CO_2$ for 72 hours. Following 72-hour incubation, absorbance is read at 540 nm. Media is removed and replaced with 100 ul of plating media containing 1 mg/mL MTT and incubated for 2 hours at 37° C. and 10% $CO_2$. MTT media is removed and replaced with 200 ul of 95% Ethanol/5% Isopropanol and allowed to shake for 15 minutes. MTT absorbance then is read at 570 nm.

Results

It is expected that the compounds and compositions of the present invention, including indirubin and chemical analogs thereof, will inhibit melanogenesis. Chemical analogs of indirubin are expected to exhibit, for example, more potent melanogenesis-inhibiting activity compared to indirubin. Likewise, certain chemical analogs of indirubin are expected to demonstrate, for example, less effective melanogenesis-inhibiting activity compared to indirubin.

Example 7

In Vitro Efficacy

It is expected that the compounds and compositions of the present invention will induce melanocyte apoptosis and modulate melanocyte activity, melanin production, melanosome biogenesis, and/or melanosome transfer at least as potently as indirubin. It is also contemplated that certain of the compounds and compositions of the present invention will affect these biological processes less potently than indirubin. Such compounds and compositions may have more favorable toxicity profiles compared to more potent species.

Example 8

In Vivo Efficacy

It is expected that the compounds and compositions of the present invention will be at least as effective as indirubin for modulating skin pigmentation, including brightening skin, and improving hyperpigmentation/hypopigmentation caused by various disorders. It is further expected that the compounds and compositions of the present invention will exhibit favorable pharmacokinetic profiles in terms of, for example, half-life and absorption. Certain compounds will exhibit a longer half-life, whereas others will exhibit a shorter half-life. Similarly, certain compounds will exhibit different absorption profiles, with some compounds taking longer to be fully absorbed and others taking less time to be fully absorbed.

Example 9

Apoptosis-Inducing Activity of Compositions Containing *Malassezia*-Derived Compounds and/or Chemical Analogs Thereof Reagents Alexa Fluor 488 Annexin V/Dead Cell Apoptosis Kit, Fetal Bovine Serum (FBS), 0.25% Trypsin-EDTA (lx), Caspase-Glo 3/7 Assay, RPMI 1640 Medium, Dulbecco's Modified Eagle Medium, and Antibiotic Antimycotic Solution (100×).

The cell lines MeWo (ATCC® HTB-65™), WM115 (ATCC® CRL-1675) and B16F1 (ATCC® CRL-6323) are maintained in the following culture media: culture medium for MeWo and B16F1: DMEM supplemented with 10% FBS; culture medium for WM115: RPMI 1640 supplemented with 10% FBS.

Experimental Methods

Cells are harvested and the cell number determined using a Countess Cell Counter. The cells are diluted with culture medium to the desired density. The final cell density may be, for example, 4,000 cells/well for 6 hr and 24 hr treatment, and 2,000 cells/well for 48 hr and 72 hr treatment. For the Annexin V assay, 384-well clear-bottom plates (Corning 3712) are employed, whereas 384-well solid white-bottom plates (Corning 3570) are used for the Caspase-Glo assays. All plates are covered with a lid and placed at 37° C. and 5% $CO_2$ overnight for cell attachment.

Test compounds are dissolved in DMSO to 30 mM stock. 10-fold dilutions are performed to generate 3 mM and 0.3 mM concentrations. 0.9 mM Staurosporine is employed as positive control, and DMSO is employed as negative control (NC). 132.5 nL of compounds is transferred from compound source plate to 384-well cell culture plate(s) using liquid handler Echo550. After the indicated incubation time, the plates are removed from the incubator for detection.

Test compositions are dissolved DMSO, EPI-100-LLMM, or any appropriate solvent and may be prepared according to the instructions in Tables 2-7 below. Appropriate solvents are well known to those of skill in the art.

For the Annexin V assay, plates are removed from the incubator and culture media is removed. Cells are washed twice with 40 uL PBS and 15 uL of pre-mixed Annexin V-FITC and Hoechst 33342 dye working solution are added per well. Plates are incubated at room temperature for 20 minutes, sealed, and centrifuged for 1 minute at 1,000 rpm to remove bubbles. Plates are read using ImageXpress Nano.

For the Caspase-Glo assay, plates are removed from the incubator and equilibrated at room temperature for 15 minutes. Caspase-Glo 3/7 reagents also are thawed and equilibrated to room temperature before the experiment. Caspase-Glo reagent is added to the required wells at 1:1 ratio to the culture medium. Plates are incubated at room temperature for 15 minutes and read using EnSpire™ plate reader. Fold induction is calculated according to the following formula: Fold induction=$Lum_{Sample}/Lum_{NC}$.

Annexin V Assay and Caspase 3/7 Assay Results

It is expected that the compounds and compositions of the present invention, including Compositions #1-5, will induce cell death. Compositions of the present invention are expected to exhibit, for example, more potent apoptosis-inducing activity compared to at least one component compound alone. Likewise, compositions of the present invention are expected to demonstrate, for example, less effective apoptosis-inducing activity compared to at least one component compound alone. Such compositions may have more favorable toxicity profiles compared to more potent compositions.

Example 10

Cell Viability After Exposure to Compositions Containing *Malassezia*-Derived Compounds and/or Chemical Analogs Thereof Reagents CellTiter-Glo® 2.0 assay.

Experimental Methods

For the CellTiter-Glo assay, test compounds are prepared in 10 mM DMSO solution. Compounds are serially diluted into 12 concentrations. 40 uL of cells from a 100,000 cell/mL suspension are dispensed into each well of a 384-well plate (Corning 3570). Plates are incubated overnight at 37° C., 5% $CO_2$, and 95% humidity. Test compounds are added, with DMSO as vehicle control. Plates are incubated at 37° C., 5% $CO_2$, and 95% humidity for 6, 24, or 48 hours, and 40 uL of CellTiter-Glo reagent is added to the wells to assess cell viability.

Test compositions are dissolved DMSO, EPI-100-LLMM, or any appropriate solvent and may be prepared according to the instructions in Tables 4-9 below. Appropriate solvents are well known to those of skill in the art.

Results

It is expected that the compounds and compositions of the present invention, including Compositions #1-5, will induce cell death. Compositions of the present invention are expected to exhibit, for example, more potent apoptosis-inducing activity compared to at least one component compound alone. Likewise, compositions of the present invention are expected to demonstrate, for example, less effective apoptosis-inducing activity compared to at least one component compound alone. Such compositions may have more favorable toxicity profiles compared to more potent compositions.

Example 11

Arylhydrocarbon Receptor Activation Potential of Compositions Containing *Malassezia*-Derived Compounds and/or Chemical Analogs Thereof Assay Procedures Culture media for stably transfected HepG2 cells is prepared by supplementing DMEM with high glucose and L-glutamine, as well as 10% FBS.

HepG2-AhR-Luc cells are cultured in T-75 flasks at 37° C., 5% $CO_2$, and 95% relative humidity. Cells are allowed to reach 80-90% confluence before detachment and splitting.

Cultivated cells are rinsed with 5 mL PBS. PBS is aspirated away, 1.5 mL trypsin is added to the flask, and cells are incubated at 37° C. for approximately 5 minutes or until the cells are detached and float. Trypsin is inactivated by adding excess serum-containing media.

The cell suspension is transferred to a conical tube and centrifuged at 120 g for 10 minutes to pellet the cells. Cells are resuspended in seeding media at a proper density. 40 µL of cells are transferred to a 384-well culture plate ($5\times10^3$ cells/well). Plates are placed in the incubator at 37° C. for 24 hours.

Afterward, stock solutions of test compounds, test compositions, and omeprazole positive control are prepared. Compound and compositions solutions are transferred into the assay plate using Echo550. The plate is then placed back into the incubator for compound/composition treatment.

Later, after 24 hours of treatment, the plate is removed from the incubator and allowed to cool at ambient temperature. 30 µL One-Glo reagent equal to that of the culture medium is added in each well. Cells are allowed to lyse for at least 3 minutes, and then measured in a luminometer.

Dose responses are graphed using the non-linear regression analysis in XLfit, and $EC_{50}$ values are also calculated.

Results

It is expected that the compounds and compositions of the present invention, including Compositions #1-5, will modulate AhR activity. Compositions of the present invention are expected to exhibit, for example, more potent AhR agonist activity compared to at least one component compound alone. Likewise, compositions of the present invention are expected to demonstrate, for example, less effective AhR agonist activity compared to at least one component compound alone. Compositions of the present invention also are expected to exhibit, for example, more potent AhR antagonist activity compared to at least one component compound alone. Likewise, compositions of the present invention also are expected to demonstrate, for example, less effective AhR antagonist activity compared to at least one component compound alone.

Example 12

MelanoDerm™ Assays

The purpose of this study was to evaluate the potential action of the test articles as a skin melanogenesis modulator in the MelanoDerm™ Skin Model after repeated test article exposures. Secondarily, the purpose of this study was to evaluate the potential dermal irritation of the test article to the MelanoDerm™ Skin Model after repeated exposures. Toxicity was determined by measuring the relative conversion of MTT (3-[4,5-dimethylthiazol-2-yl]-2,5-diphenyltetrazolium bromide) in the test article-treated tissues compared to the negative/solvent control-treated tissues. The potential impact on melanin production was determined by measuring the concentration of melanin produced by the test article-treated tissues compared to the negative/solvent control-treated tissues.

Identification of Test Substances and Assay Controls

TABLE 4

Test Articles Tested in Diluted Form

| Test Article Designation | Sponsor Designation | Dosing Concentration | Preparation Instructions |
|---|---|---|---|
| 18AH47 | DMSO (solvent control) | 0.5% (v/v) | The solvent control was diluted (v/v) with EPI-100-LLMM to a final concentration of 0.5%; the diluted solvent control was vortexed for at least 1 minute and dosed onto the tissues using a dosing volume of 25 µL. A total volume of up to 0.5 mL was prepared for each tissue treatment. |
| 17AJ41 | Malassezin (CV-8684) (Positive control) | 500 µM | Starting from the stock concentration provided by the Sponsor/prepared from the solid material provided by the Sponsor, the test article/control was diluted (v/v) with EPI-100-LLMM to the |
| 17AJ55 | O52 | 650 µM | dosing concentration listed. The test article |
| 18AA21 | Malassezia Indole A | 650 µM | dilution was vortexed for at least 1 minute, heated at 37° ± 1° C. (in a water bath) for 15 minutes, |

TABLE 4-continued

| Test Article Designation | Sponsor Designation | Dosing Concentration | Preparation Instructions |
|---|---|---|---|
| Test Articles Tested in Diluted Form | | | |
| 18AF50 | AB17151 | 300 μM | vortexed again for at least 1 minute and dosed on the tissues using a dosing volume of 25 μL. A total volume of up ~0.5 mL was prepared for each tissue treatment. |
| 18AH15 | AB17590 | 300 μM | |
| 18AH21 | AB11644 | 650 μM | |
| 18AH38 | Indole-3-carbaldehyde | 500 μM | |
| 18AH39 | D-indole-3-lactic acid | 500 μM | |

TABLE 5

| Test Article Designation | Sponsor Designation | Preparation Instructions For Working Stock Solutions | Dosing Concentration | Preparation Instructions For Dilutions Used For Dosing of the Tissues |
|---|---|---|---|---|
| Composition #1 | | | | |
| 17AD42 | Indolo-carbazole (ICZ) | A working stock solution of 360 μM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 μM. The dilution was vortexed for at least 1 minute, heated at 37° ± 1° C. (in a water bath) for 15 minutes and vortexed again for at least 1 minute before being subsequently diluted. | The dosing concentration of each of the components was 18 μM. | Fifty (50) μL of each working stock solution was transferred into a new vial (combined volume of 700 μL) and mixed with 300 μL of EPI-100-LLMM to yield a total volume of 1000 μL. The dilution was vortexed for at least 1 minute before being applied onto the tissues. |
| 17AJ41 | Malassezin (CV-8684) (Positive control) | | | |
| 17AJ47 | Compound A5 (also known as Keto-Malassezin) | | | |
| 17AJ55 | O52 | | | |
| 18AA21 | Malassezia Indole A | | | |
| 18AA22 | Pityriacitrin | | | |
| 18AA24 | FICZ | | | |
| 18AD42 | Indirubin | | | |
| 18AH16 | Trypthantrin | | | |
| 18AH20 | Malassezia-lactic Acid | | | |
| 18AH24 | 2-hydroxy-1-(1H-indol-3-yl)ethanone | | | |
| 18AH38 | Indole-3-carbaldehyde | | | |
| 18AH39 | D-Indole-3-lactic acid | | | |
| 18AH44 | (Indol-3-yl)pyruvic acid | | | |

TABLE 6

| Test Article Designation | Sponsor Designation | Preparation Instructions For Working Stock Solutions | Dosing Concentration | Volume Needed (μL) | Preparation Instructions For Dilutions Used For Dosing of the Tissues |
|---|---|---|---|---|---|
| Composition #2 | | | | | |
| 17AD42 | Indolo-carbazole (ICZ) | A working stock solution of 360 μM | 12.6 μM | 35 | The volume of the dosing |

TABLE 6-continued

| Composition #2 | | | | | |
|---|---|---|---|---|---|
| Test Article Designation | Sponsor Designation | Preparation Instructions For Working Stock Solutions | Dosing Concentration | Volume Needed (μL) | Preparation Instructions For Dilutions Used For Dosing of the Tissues |
| 17AJ41 | Malassezin (CV-8684) (Positive control) | was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 μM. The dilution was vortexed for at least 1 minute, heated at 37° ± 1° C. (in a water bath) for 15 minutes and vortexed again for at least 1 minute before being subsequently diluted. | 50.4 μM | 140 | concentration listed for each component was transferred into a new vial and mixed with 297 μL of EPI-100-LLMM. The dilution was vortexed for at least 1 minute before being applied onto the tissues. |
| 17AJ47 | Compound A5 (also known as Keto-Malassezin) | | 10.1 μM | 28 | |
| 17AJ55 | O52 | | 10.1 μM | 28 | |
| 18AA21 | Malassezia Indole A | | 10.1 μM | 28 | |
| 18AA22 | Pityriacitrin | | 50.4 μM | 140 | |
| 18AA24 | FICZ | | 10.1 μM | 28 | |
| 18AD42 | Indirubin | | 24.5 μM | 68 | |
| 18AH16 | Trypthantrin | | 24.5 μM | 68 | |
| 18AH20 | Malassezia-lactic Acid | | 10.1 μM | 28 | |
| 18AH24 | 2-hydroxy-1-(1H-indol-3-yl)ethanone | | 10.1 μM | 28 | |
| 18AH38 | Indole-3-carbaldehyde | | 10.1 μM | 28 | |
| 18AH39 | D-Indole-3-lactic acid | | 10.1 μM | 28 | |
| 18AH44 | (Indol-3-yl)pyruvic acid | | 10.1 μM | 28 | |

TABLE 7

| Composition #3 | | | | | |
|---|---|---|---|---|---|
| Test Article Designation | Sponsor Designation | Preparation Instructions for Working Stock Solutions | Dosing Concentration (μM) | Volume Needed (μL) | Preparation Instructions for Dilutions Used for Dosing of the Tissues |
| 17AJ41 | Malassezin (CV-8684) (Positive control) | A working stock solution of 360 μM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 μM. The dilution was vortexed for at least 1 minute, heated at 37° ± 1° C. (in a water bath) | 50.4 | 140 | The volume of the dosing concentration listed for each component was transferred into a new vial and mixed with 568 μL of EPI-100-LLMM. The dilution was vortexed for at least 1 minute before being applied onto the tissues. |
| 17AD46 | Compound A5 (CV-8819) (also known as Keto-Malassezin) | | 10.1 | 28 | |
| 17AJ55 | O52 (AB12976) | | 10.1 | 28 | |
| 18AA21 | Malassezia Indole A (AB17011) | | 10.1 | 28 | |
| 18AD42 | Indirubin | | 24.5 | 68 | |
| 18AH20 | AB17227 (also known as Malassezia-lactic Acid) | | 10.1 | 28 | |
| 18AH24 | 2-hydroxy-1-(1H-indol-3-yl)ethanone | | 10.1 | 28 | |
| 18AH38 | Indole-3-carbaldehyde | | 10.1 | 28 | |
| 18AH39 | D-Indole-3-lactic acid | | 10.1 | 28 | |

TABLE 7-continued

| Composition #3 | | | | | |
|---|---|---|---|---|---|
| Test Article Designation | Sponsor Designation | Preparation Instructions for Working Stock Solutions | Dosing Concentration (μM) | Volume Needed (μL) | Preparation Instructions for Dilutions Used for Dosing of the Tissues |
| 18AH44 | (Indol-3-yl)pyruvic acid | for 15 minutes and vortexed again for at least 1 minute before being subsequently diluted. | 10.1 | 28 | |

TABLE 8

| Composition #4 | | | | | |
|---|---|---|---|---|---|
| Test Article Designation | Sponsor Designation | Preparation Instructions for Working Stock Solutions | Dosing Concentration (μM) | Volume Needed (μL) | Preparation Instructions for Dilutions Used for Dosing of the Tissues |
| 17AD42 | CV-8685 (also known as Indolo-carbazole or ICZ) | A working stock solution of 360 μM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 μM. The dilution was vortexed for at least 1 minute, heated at 37° ± 1° C. (in a water bath) for 15 minutes and vortexed again for at least 1 minute before being subsequently diluted. | 12.6 | 35 | The volume of the dosing concentration listed for each component was transferred into a new vial and mixed with 505 μL of EPI-100-LLMM. The dilution was vortexed for at least 1 minute before being applied onto the tissues. |
| 17AJ41 | Malassezin (CV-8684) (Positive control) | | 50.4 | 140 | |
| 17AD46 | Compound A5 (CV-8819) (also known as Keto-Malassezin) | | 10.1 | 28 | |
| 17AJ55 | O52 (AB12976) | | 10.1 | 28 | |
| 18AA21 | Malassezia Indole A (AB17011) | | 10.1 | 28 | |
| 18AA24 | FICZ | | 10.1 | 28 | |
| 18AD42 | Indirubin | | 24.5 | 68 | |
| 18AH20 | AB17227 (also known as Malassezia-lactic Acid) | | 10.1 | 28 | |
| 18AH24 | 2-hydroxy-1-(1H-indol-3-yl)ethanone | | 10.1 | 28 | |
| 18AH38 | Indole-3-carbaldehyde | | 10.1 | 28 | |
| 18AH39 | D-Indole-3-lactic acid | | 10.1 | 28 | |
| 18AH44 | (Indol-3-yl)pyruvic acid | | 10.1 | 28 | |

TABLE 9

| Composition #5 | | | | | |
|---|---|---|---|---|---|
| Test Article Designation | Sponsor Designation | Preparation Instructions for Working Stock Solutions | Dosing Concentration (µM) | Volume Needed (µL) | Preparation Instructions for Dilutions Used for Dosing of the Tissues |
| 17AD42 | CV-8685 (also known as Indolo-carbazole or ICZ) | A working stock solution of 360 µM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 µM. The dilution was vortexed for at least 1 minute, heated at 37° ± 1° C. (in a water bath) for 15 minutes and vortexed again for at least 1 minute before being subsequently diluted. | 74.9 | 208 | The volume of the dosing concentration listed for each component was transferred into a new vial and mixed with 306 µL of EPI-100-LLMM. The dilution was vortexed for at least 1 minute before being applied onto the tissues. |
| 17AJ41 | Malassezin (CV-8684) (Positive control) | | 10.1 | 28 | |
| 18AA22 | Pityriacitrin (AB17014) | | 10.1 | 28 | |
| 18AA24 | FICZ | | 74.9 | 208 | |
| 18AD42 | Indirubin | | 24.8 | 69 | |
| 18AH16 | Trypthantrin | | 10.1 | 28 | |
| 18AH24 | 2-hydroxy-1-(1H-indol-3-yl)ethanone | | 10.1 | 28 | |
| 18AH39 | D-Indole-3-lactic acid | | 24.8 | 69 | |
| 18AH44 | (Indol-3-yl)pyruvic acid | | 10.1 | 28 | |

Assay controls include: positive control—malassezin (CV-8684) (500 µM) (17AJ41) and solvent control—DMSO (dimethyl sulfoxide) prepared in EPI-100-LLMM.

Additionally, the test article and controls were applied to groups of 4 tissues of which 2 were used for the Tissue Viability (MTT) endpoint and 2 for the Melanin endpoint, respectively.

Test System

The MelanoDerm™ Skin Model provided by MatTek Corporation (Ashland, MA) was used in this study. The MelanoDerm™ tissue consists of normal, human-derived epidermal keratinocytes (NHEK) and melanocytes (NHM) which have been cultured to form a multilayered, highly differentiated model of the human epidermis. The NHMs within co-cultures undergo spontaneous melanogenesis leading to tissues of varying levels of pigmentation. The cultures were grown on cell culture inserts at the air-liquid interface, allowing for topical application of skin modulators. The MelanoDerm™ model exhibits in vivo-like morphological and ultrastructural characteristics. NHM localized in the basal cell layer of MelanoDerm™ tissue are dendritic and spontaneously produce melanin granules which progressively populate the layers of the tissue. Thus the test system is used to screen for materials which may inhibit or stimulate the production of melanin relative to the negative controls.

Experimental Design and Methodology

The experimental design of this study consisted of the determination of the pH of the neat test article if possible (and/or dosing solution as appropriate) and a definitive assay to determine the relative tissue viability and the potential action of the test article as a skin melanogenesis modulator to MelanoDerm™ Skin Model after repeated exposures. The test articles were exposed to the MelanoDerm™ Skin Model for a total of 7 days. The test articles were topically applied to the MelanoDerm™ Skin Model every 48 hours (within a timeframe of 48±2 hours from previous treatment). The toxicity of the test articles were determined by the NAD(P)H-dependent microsomal enzyme reduction of MTT (and, to a lesser extent, by the succinate dehydrogenase reduction of MTT) in control and test article-treated tissues. Data was presented in the form of relative survival (MTT conversion relative to the negative/solvent control). The potential impact on melanin production was evaluated by determining the concentration of melanin produced in the test article-treated tissues compared to the negative/solvent control-treated tissues. Data was presented in the form of concentration of melanin produced by the test article-treated tissues determined using a melanin standard curve. Alternatively, data may be presented as percent change in melanin concentration relative to the negative/solvent control-treated tissues.

The methods used are a modification of the procedures supplied by MatTek Corporation.

Media and Reagents

MelanoDerm™ Maintenance Medium (EPI-100-LLMM) was purchased from MatTek Corporation. MelanoDerm™ Skin Model (MEL-300-A) was purchased from MatTek Corporation. 1% Kojic acid (prepared in sterile, deionized water) was purchased from Sigma MTT (3-[4,5-dimethylthiazol-2-yl]-2,5-diphenyltetrazolium bromide) was purchased from Sigma. Dulbecco's Modified Eagle's Medium (DMEM) containing 2 mM L-glutamine (MTT Addition Medium) was purchased from Quality Biological. Extraction Solvent (Isopropanol) was purchased from Aldrich. Sterile Ca++ and Mg++ Free Dulbecco's Phosphate Buffered Saline (CMF-DPBS) was purchased from Invitrogen. Melanin was purchased from Sigma. Sterile deionized water was purchased from Quality Biological. Solvable was purchased from Perkin Elmer.

Preparation and Delivery of Test Article

Unless otherwise specified within this protocol, twenty five microliters of each test article were applied directly on the tissue so as to cover the upper surface. Depending on the nature of the test article (liquids, gels, creams, foams, and the like), the use of a dosing device, mesh or other aid to allow the uniform spreading of the test article over the surface of the tissue may have been necessary.

Route of Administration

The test articles were applied topically to the MelanoDerm™ tissue every 48 hours (within a timeframe of 48+2 hours from previous treatment) during a 7-day trial. Twenty five microliters of each test article were applied to each tissue. Twenty five microliters of the positive and negative/solvent controls, respectively, were applied to each tissue.

pH Determination

The pH of the neat liquid test article (and/or dosing solution as appropriate) was determined, if possible. The pH was determined using pH paper (for example, with a pH range of 0-14 to estimate, and/or a pH range of 5-10 to determine a more precise value). The typical pH increments on the narrower range pH paper were approximately 0.3 to 0.5 pH units. The maximum increment on the pH paper was 1.0 pH units.

Controls

The definitive assay included a negative control, a positive control and one solvent control (DMSO) or a positive control and a solvent control (DMSO). The MelanoDerm™ tissues designated to the assay negative/solvent control were treated with 25 μL of sterile, deionized water or DMSO. The tissues designated to the assay positive control were treated with 25 μL of 1% Kojic acid, Malassezin (CV-8684) (17AJ41) 500 μM, or Composition #2. The 1% Kojic acid was stored in a tube covered with aluminum foil until used within 2 hours of preparation. The negative/solvent and positive control exposure times were identical to those used for the test articles. Untreated tissues were also used as controls.

Assessment of Direct Test Article Reduction of MTT

It was necessary to assess the ability of each test article to directly reduce MTT. A 1.0 mg/mL MTT solution was prepared in MTT Addition Medium. Approximately 25 μL of the test article was added to 1 mL of the MTT solution and the mixture was incubated in the dark at 37±1° C. for one to three hours. A negative control, 25 μL of sterile, deionized water, or a solvent control, 25 μL of DMSO was tested concurrently. If the MTT solution color turned blue/purple, the test article was presumed to have reduced the MTT. Water insoluble test materials may have shown direct reduction (darkening) only at the interface between the test article and the medium.

Receipt of MelanoDerm™

Upon receipt of the MelanoDerm™ Skin Kit, the solutions were stored as indicated by the manufacturer. The MelanoDerm™ tissues were stored at 2-8° C. until used.

On the day of receiving (the day before dosing), an appropriate volume of MelanoDerm™ Maintenance Medium (EPI-100-LLMM) was removed and warmed to 37±1° C. Nine-tenths (0.9) mL of EPI-100-LLMM/well were aliquoted into the appropriate wells of 6-well plates. Each MelanoDerm™ tissue was inspected for air bubbles between the agarose gel and cell culture insert prior to opening the sealed package. Tissues with air bubbles greater than 50% of the cell culture insert area were not used. The 24-well shipping containers were removed from the plastic bag and the surface disinfected with 70% ethanol. An appropriate number of MelanoDerm™ tissues were transferred aseptically from the 24-well shipping containers into the 6-well plates. The MelanoDerm™ tissues were incubated at 37±1° C. in a humidified atmosphere of 5±1% $CO_2$ in air (standard culture conditions) overnight (at least 16 hours) to acclimate the tissues. Upon opening the bag, any unused tissues remaining on the shipping agar at the time of tissue transfer were briefly gassed with an atmosphere of 5% $CO_{2/95}$% air, and the bag was sealed and stored at 2-8° C. for subsequent use.

Definitive Assay

Tissue Exposure: At least 16 hours after initiating the cultures, five MelanoDerm™ tissues (considered untreated at Day 0) were photographed using a digital camera to aid in the visual assessment of the degree of pigmentation of the tissues at time zero of the assay. Two MelanoDerm™ tissues were rinsed with CMF-DPBS, blotted dry on sterile absorbent paper and cleared of excess liquid. The MelanoDerm™ tissues were transferred to the appropriate MTT containing wells after rinsing and processed in the MTT assay. Two or three MelanoDerm™ tissues were rinsed with CMF-DPBS, blotted dry on sterile absorbent paper and cleared of excess liquid. The MelanoDerm™ tissues were removed from the cell culture insert using sterile scalpels, placed in a labeled 1.5 mL microfuge tube, and stored at <−60° C. for subsequent melanin analysis.

At least 16 hours after initiating the cultures, the rest of the tissues were transferred on a new 6-well plate containing 0.9 mL/well of fresh, pre-warmed EPI-100-LLMM. The trial was conducted over a 7-day timeframe. Four or five tissues were treated topically on the first day, and every 48 hours (within a timeframe of 48+2 hours from previous treatment) with 25 μL, of each test article. The medium was refreshed daily (within a timeframe of 24+2 hours from previous refeeding); the tissues were transferred to a new 6-well plate containing 0.9 mL/well of fresh, pre-warmed EPI-100-LLMM.

Four or five tissues were treated topically on the first day, and every 48 hours (within a timeframe of 48+2 hours from previous treatment) with 25 μL of positive and negative/solvent controls, respectively. The medium was refreshed daily (within a timeframe of 24+2 hours from previous refeeding); the tissues were transferred to a new 6-well plate containing 0.9 mL/well of fresh, pre-warmed EPI-100-LLMM. The tissues were incubated at 37±1° C. in a humidified atmosphere of 5±1% $CO_2$ in air (standard culture conditions) for the appropriate exposure times.

On the days of dosing, the MelanoDerm™ tissue was first gently rinsed three times using ~500 μL of CMF-DPBS per rinse to remove any residual test article. The CMF-DPBS was gently pipetted into the well and then drawn off with a sterile aspirator. The tissues were transferred to a new 6-well plate containing 0.9 mL of fresh, pre-warmed EPI-100-LLMM and dosed with the appropriate test article, negative/solvent or positive control. The tissues were incubated at 37±1° C. in a humidified atmosphere of 5±1% $CO_2$ in air (standard culture conditions) for the appropriate exposure times.

At the end of the 7-day trial, the MelanoDerm™ tissues treated with the negative/solvent or positive control, and with each test article were photographed using a digital camera to aid in the visual assessment of the degree of pigmentation of the tissues at the end of the assay (Day 7). Then, the viability of two tissues treated with the positive and negative control, respectively, and with each test article, were determined by MTT reduction. At the end of the 7-day trial, the melanin produced by three tissues treated with each test article, the positive and negative/solvent control, respectively, was determined.

MTT Assay: A 10× stock of MTT prepared in PBS (filtered at time of batch preparation) was thawed and diluted in warm MTT Addition Medium to produce the 1.0 mg/mL solution no more than two hours before use. Three hundred μL of the MTT solution was added to each designated well of a prelabelled 24-well plate.

After the exposure time, each MelanoDerm™ tissue designated for the MTT assay was rinsed with CMF-DPBS (use of spray bottle acceptable for this step), blotted dry on sterile absorbent paper, and cleared of excess liquid. The MelanoDerm™ tissues were transferred to the appropriate MTT containing wells after rinsing. The 24-well plates were incubated at standard conditions for 3±0.1 hours.

After 3±0.1 hours, the MelanoDerm™ tissues were blotted on sterile absorbent paper, cleared of excess liquid, and transferred to a prelabelled 24-well plate containing 2.0 mL of isopropanol in each designated well. The plates were covered with parafilm and stored in the refrigerator (2-8° C.) until the last exposure time was harvested. If necessary, plates were stored overnight (or up to 24 hours after the last exposure time is harvested) in the refrigerator prior to extracting the MTT. Then the plates were shaken for at least 2 hours at room temperature. At the end of the extraction period, the liquid within the cell culture inserts was decanted into the well from which the cell culture insert was taken. The extract solution was mixed and 200 μL transferred to the appropriate wells of 96-well plate. Two hundred μL of isopropanol was added to the wells designated as blanks. The absorbance at 550 nm (OD550) of each well was measured with a Molecular Devices Vmax plate reader.

Melanin Assay: At the end of the appropriate exposure times, the MelanoDerm™ tissues designated for the melanin assay were gently rinsed at least three times using ~500 μL of CMF-DPBS per rinse to remove any residual test article or excess phenol red from culture medium, blotted dry on sterile absorbent paper and cleared of excess liquid. The MelanoDerm™ tissues were photographed using a digital camera at the end of the assay. The MelanoDerm™ tissues were removed from the cell culture insert using sterile scalpels or sterile punche(s), placed in a labeled 1.5 mL microfuge tube, and stored at <−60° C. for subsequent melanin analysis.

On the day of the melanin extraction assay, the excised tissues were thawed at room temperature for approximately 10 minutes. 250 μL Solvable was added to each microfuge tube and the tubes were incubated for at least 16 hours at 60+2° C. A 1 mg/mL Melanin standard stock solution was prepared by dissolving the Melanin in Solvable. A series of Melanin standards was prepared from the 1 mg/mL stock ranging from 0 mg/mL to 0.33 mg/mL. The standard series was prepared by adding 0.6 mL of the 1 mg/mL Melanin standard stock solution to 1.2 mL Solvable, and then making a series of five more dilutions (dilution factor of 3). Solvable was used as the zero standard. The Melanin standards series and the Solvable were incubated for at least 16 hours at 60+2° C.

At least 16 hours after initiating the melanin extraction, the tubes containing the samples (representing the melanin extracted from the MelanoDerm™ tissues) and the standards were cooled at room temperature and centrifuged at 13,000 rpm for 5 minutes at room temperature. 200 μL of samples (single wells) or standards (duplicate wells) were transferred to the appropriate wells of a 96-well plate. Two hundred μL of Solvable were added to the wells designated as blanks in duplicate wells. The absorbance at 490 nm (OD490) of each well was measured with a Molecular Devices Vmax plate reader (with Automix function selected).

Killed Controls for Assessment of Residual Test Article Reduction of MTT

To demonstrate that possible residual test article was not acting to directly reduce the MTT, a functional check was performed in the definitive assay to show that the test material was not binding to the tissue and leading to a false MTT reduction signal.

To determine whether residual test article was acting to directly reduce the MTT, a freeze-killed control tissue was used. Freeze killed tissue was prepared by placing untreated MelanoDerm™/EpiDerm™ (Melanoderm™ without melanocytes) tissues in the −20° C. freezer at least overnight, thawing to room temperature, and then refreezing. Once killed, the tissue may be stored indefinitely in the freezer. Freeze killed tissues may be received already prepared from MatTek Corporation, and stored in the −20° C. freezer until use. To test for residual test article reduction, killed tissues were treated with the test article in the normal fashion. All assay procedures were performed in the same manner as for the viable tissue. At least one killed control treated with sterile deionized water (negative killed control) was tested in parallel since a small amount of MTT reduction is expected from the residual NADH and associated enzymes within the killed tissue.

If little or no MTT reduction was observed in the test article-treated killed control, the MTT reduction observed in the test article-treated viable tissue may be ascribed to the viable cells. If there was appreciable MTT reduction in the treated killed control (relative to the amount in the treated viable tissue), additional steps must be taken to account for the chemical reduction or the test article may be considered untestable in this system.

Data Analysis

The mean OD550 value of the blank wells was calculated. The corrected mean OD550 value of the negative/solvent control(s) was determined by subtracting the mean OD550 value of the blank wells from their mean OD550 values. The corrected OD550 values of the individual test article exposures and the positive control exposures was determined by subtracting from each the mean OD550 value for the blank wells. All calculations were performed using an Excel spreadsheet. Although the algorithms discussed are performed to calculate the final endpoint analysis at the treatment group level, the same calculations can be applied to the individual replicates.

Corr. Test article exposure OD550=Test article exposure OD550−Blank mean OD550

If killed controls (KC) were used, the following additional calculations were performed to correct for the amount of MTT reduced directly by test article residues. The raw OD550 value for the negative control killed control was subtracted from the raw OD550 values for each of the test article-treated killed controls, to determine the net OD550 values of the test article-treated killed controls.

Net $OD_{550}$ for each test article KC=Raw $OD_{550}$ test article KC−Raw $OD_{550}$ negative/solvent control KC The net OD550 values represent the amount of reduced MTT due to direct reduction by test article residues at specific exposure times. In general, if the net OD550 value is greater than 0.150, the net amount of MTT reduction will be subtracted from the corrected OD550 values of the viable treated tissues to obtain a final corrected OD550 value. These final corrected OD550 values will then be used to determine the % of Control viabilities.

Final Corrected OD550=Corrected test article OD550 (viable)−Net OD550 test article (KC)

Finally, the following % of Control calculations will be made:

% Viability=[(Final corrected $OD_{550}$ of Test Article or Positive Control)/(Corrected mean $OD_{550}$ of Negative/Solvent Control(s))]×100

Melanin Analysis: The raw absorbance data was captured, saved as a print-file and imported into an Excel spreadsheet. The OD490 value of each test sample (representing the melanin extracted from untreated MelanoDerm™ tissues at Day 0, MelanoDerm™ tissues treated with each test article, negative/solvent or positive controls at Day 7) and of the melanin standards was determined. The corrected OD490 value for the test samples and each melanin standard was determined by subtracting the mean OD490 value of the blank wells. The standard curve was plotted as the concentration of the standards in mg/mL (y-axis) versus the corresponding corrected absorbance. The amount of melanin in each individual tissue was interpolated from the standard curve (linear). Finally, the average of melanin concentration for each test article or control treatment groups, respectively, was calculated.

Results

FIG. 4 summarizes the mean tissue viability and melanin concentration results for the test articles, test compositions, positive control, and solvent control. The compounds comprising compositions #1 and #2 demonstrated synergistic effects when combined in a single composition.

FIG. 5 summarizes the mean tissue viability and melanin concentration results for the test articles, test compositions, positive control, and solvent control. The compounds comprising compositions #2, #3, #4, and #5 demonstrated synergistic effects when combined in a single composition.

Example 13

Melanogenesis Potential of Compositions Containing *Malassezia*-Derived Compounds and/or Chemical Analogs Thereof The purpose of this study is to observe and report melanogenesis and viability of B16 melanocytes exposed to compositions containing *Malassezia*-derived compounds and/or chemical analogs thereof.

Materials and Reagents

Plating media will include DMEM without L-glutamine, FBS, penicillin/streptomycin, and L-glutamine. Assay media will include DMEM without phenol red and L-glutamine, FBS, penicillin/streptomycin, L-glutamine, and aMSH. Other reagents will include Kojic Acid, DMSO, and MTT. Cells tested will be B16 cells (ATCC CRL-6475).

Protocol

B16 Melanocytes are cultured until 70% confluent and harvested. Cells are seeded in 96-well plates at a density of 4000 cells/well and are allowed to attach overnight. The following day, test articles, test compositions, and controls are diluted in B16 Assay media. Overnight media is aspirated and 200 ul of test articles and controls are applied. Cells are incubated at 37° C. and 10% $CO_2$ for 72 hours. Following 72-hour incubation, absorbance is read at 540 nm. Media is removed and replaced with 100 ul of plating media containing 1 mg/mL MTT and incubated for 2 hours at 37° C. and 10% $CO_2$. MTT media is removed and replaced with 200 ul of 95% Ethanol/5% Isopropanol and allowed to shake for 15 minutes. MTT absorbance then is read at 570 nm.

Results

It is expected that the compounds and compositions of the present invention, including Compositions #1-5, will inhibit melanogenesis. Compositions of the present invention are expected to exhibit, for example, more potent melanogenesis-inhibiting activity compared to at least one component compound. Likewise, certain compositions are expected to demonstrate, for example, less effective melanogenesis-inhibiting activity compared to at least one component compound.

Example 14

In Vitro Efficacy

It is expected that the compounds and compositions of the present invention will induce melanocyte apoptosis and modulate melanocyte activity, melanin production, melanin concentration, melanosome biogenesis, and/or melanosome transfer. It is also contemplated that certain of the compounds and compositions of the present invention will affect these biological processes less potently. Such compounds and compositions may have more favorable toxicity profiles compared to more potent species.

Example 15

In Vivo Efficacy

It is expected that the compounds and compositions of the present invention will modulate skin pigmentation, including brightening skin, and improving hyperpigmentation/hypopigmentation caused by various disorders. It is further expected that the compounds and compositions of the present invention will exhibit favorable pharmacokinetic profiles in terms of, for example, half-life and absorption. Certain compounds will exhibit a longer half-life, whereas others will exhibit a shorter half-life. Similarly, certain compounds will exhibit different absorption profiles, with some compounds taking longer to be fully absorbed and others taking less time to be fully absorbed.

Example 16

Synthesis of Chemical Analogs of Malassezin and Indirubin

Synthesis of AB17590

As shown in FIG. 6A, to a solution of compound 1a (25.0 g, 0.357 mol, 1.0 eq) in tetrahydrofuran (250 mL) was added ethynylmagnesium bromide (0.5 M in THF, 1.07 L, 0.535 mol, 1.5 eq) at 0° C. and the reaction mixture was warmed to room temperature and stirred for 2 h. Then the mixture was quenched with saturated aqueous of ammonium chloride and extracted with ethyl acetate. The organic layer was dried over anhydrous $Na_2SO_4$ and concentrated under reduced pressure. The residue was purified by silica gel chromatography (0-10% ethyl acetate in petroleum ether) to give compound 1b (9.5 g, 27%). TLC: PE:EA=20:1, 254 nm; $R_f$ (Compound 1a)=0.3; $R_f$ (Compound 1b)=0.7.

To a mixture of compound 1b (9.5 g, 98.96 mmol, 1.0 eq) in tetrahydrofuran (100 mL) was added a solution of 60% sodium hydride (4.7 g, 0.119 mol, 1.2 eq) in dimethylformamide (50 mL) at 0° C. under nitrogen atmosphere. After 30 minutes, dimethyl sulphate (22.4 g, 0.178 mol, 1.8 eq) was added at 0° C. After the addition the reaction mixture was allowed to warm to room temperature and stirred at room temperature for 30 min and then acetic acid (1 ml) was added slowly. The product was distilled directly from the reaction mixture. There was thus obtained compound 1c (10.0 g, 91% yield).

To a solution of compound 1 (8.0 g, 24.02 mmol, 1.0 eq) and compound 1c (2.9 g, 26.43 mmol, 1.1 eq) in triethylamine (80 mL) was added cuprous iodide (456 mg, 2.40 mmol, 0.1 eq) and $Pd(PPh_3)_2Cl_2$ (337 mg, 0.480 mmol, 0.02 eq) at room temperature under nitrogen atmosphere. The mixture was stirred at room temperature for 2 h. The progress of the reaction mixture was monitored by TLC. The reaction mixture was diluted with water and extracted with ethyl acetate. The organic layer was dried over anhydrous sodium sulfate and concentrated under reduced pressure. The residue was purified by silica gel chromatography (0~10% ethyl acetate in petroleum ether) to give compound 2 (7.0 g, 92%). TLC: PE:EA=10:1, 254 nm; $R_f$ (compound 1)=0.8; $R_f$ (compound 2)=0.6.

To an oven-dried flask was added a mixture of platinum dichloride (694 mg, 2.06 mmol, 0.1 eq), sodium carbonate (3.3 g, 30.95 mmol, 1.5 eq), tris (pentafluorophenyl) phosphine (2.2 g, 4.13 mmol, 0.2 eq), 6-methyl indole (4.8 g, 41.27 mmol, 2.0 eq) and compound 2 (6.5 g, 20.63 mmol, 1.0 eq) in dioxane (650 mL). The flask was degassed with nitrogen, sealed and heated to 100° C. for 16 h. The progress of the reaction mixture was monitored by TLC. The solvent was concentrated under reduced pressure. The residue was diluted with ethyl acetate and extracted with water, saturated brine. The organic layer was dried over anhydrous sodium sulfate and concentrated under reduced pressure. The residue was purified by silica gel chromatography (0-10% ethyl acetate in petroleum ether) to give compound 3 (3.0 g, 36%). TLC: PE:EA=10:1, 254 nm; $R_f$ (compound 2)=0.6; $R_f$ (compound 3)=0.2.

To a solution of compound 3 (3.0 g, 7.50 mmol, 1.0 eq) in tetrahydrofuran (30 mL) was added sodium methanolate (5 M in MeOH, 6.0 mL, 29.98 mmol, 4.0 eq) at 0° C. The reaction mixture was allowed to warm to room temperature and stirred for 2 h. The progress of the reaction mixture was monitored by TLC. The reaction mixture was concentrated under reduced pressure. The residue was purified by silica gel chromatography (0-10% ethyl acetate in petroleum ether) to give compound 4 (1.5 g, 66%). TLC: PE:EA=5:1, 254 nm; $R_f$ (compound 3)=0.7; $R_f$ (compound 4)=0.4.

To a dried 500 mL three-neck round-bottom flask under argon at 0° C., dimethylformamide (10 mL) was added. Then phosphorus oxychloride (1.2 g, 7.60 mmol, 1.2 eq) was slowly added while maintaining the internal temperature below 5° C. over 10 min. After stirring at 0° C. for 30 min, a solution of compound 4 (1.9 g, 6.33 mmol, 1.0 eq) in dimethylformamide (20 mL) was slowly added while maintaining the internal temperature below 5° C. over 10 min. The resulting mixture was stirred at room temperature for 16 h. After the reaction was complete (monitored by TLC using 20% ethyl acetate in hexanes), the reaction mixture was poured into saturated aqueous sodium bicarbonate (50 mL) and stirred for 1 h. Resulting mixture was extracted with ethyl acetate (2×100 mL). The combined organic layers were washed with water, saturated brine and dried over sodium sulfate. The solvent was filtered and concentrated under reduced pressure. The residue was purified by silica gel chromatography (10-50% ethyl acetate in petroleum ether) to obtain compound 5 (1.8 g, 89%). TLC: PE:EA=1:1, 254 nm; $R_f$ (compound 4)=0.8; $R_f$ (compound 5)=0.5.

To a solution of compound 5 (1.8 g, 5.49 mmol, 1.0 eq) in tetrahydrofuran (20 mL) was added Di-tert-butyl dicarbonate (3.0 g, 13.72 mmol, 2.5 eq) and 4-Dimethylaminopyridine (1.4 g, 11.25 mol, 2.05 eq) at 0° C. The reaction mixture was warmed to room temperature and stirred for 3 h. The progress of the reaction mixture was monitored by TLC. The reaction mixture was concentrated under reduced pressure and the residue was diluted with ethyl acetate and washed with 1N hydrochloric acid, saturated aqueous sodium bicarbonate (300 mL) and brine (300 mL). The organic layers were separated and dried over anhydrous sodium sulfate, filtered and concentrated. The residue was purified by silica gel chromatography (0-10% ethyl acetate in petroleum ether) to obtain compound 6 (2.4 g, 82%). TLC: PE:EA=10:1, 254 nm; $R_f$ (compound 5)=0.1; $R_f$ (compound 6)=0.5.

To a solution of compound 6 (2.4 g, 4.55 mmol, 1.0 eq) in tert-Butanol (60 mL) was added 2-methyl-2-butene (30 mL) followed by addition of sodium chlorite (8.2 g, 90.91 mmol, 20.0 eq), sodium phosphate monobasic (14.2 g, 90.91 mmol, 20.0 eq) and water (60 mL) at 0° C. The mixture was slowly warmed to room temperature and stirred at room temperature for 15 h. The progress of the reaction mixture was monitored by TLC. The reaction mixture was diluted with dichloromethane (100 mL) and separated. The organic layer was washed with water (80 mL), brine (80 mL), dried over anhydrous sodium sulfate and concentrated under reduced pressure to obtain crude compound 7 (2.5 g, 99%). TLC: PE:EA=2:1, 254 nm; $R_f$ (compound 6)=0.7; $R_f$ (compound 7)=0.3.

To a solution of compound 7 (2.5 g, 4.60 mmol, 1.0 eq) in dimethylformamide (30 mL) was added potassium carbonate (952 mg, 6.89 mmol, 1.5 eq) and methyl iodide (978 mg, 6.89 mmol, 1.5 eq) at 0° C. The reaction mixture was warmed to room temperature and stirred for 2 h. The progress of the reaction mixture was monitored by TLC. The reaction mixture was diluted with ethyl acetate (100 mL) and washed with water (100 mL) and brine (100 mL). The organic layer was dried over anhydrous sodium sulfate and concentrated under reduced pressure. The residue was purified by silica gel chromatography (5-17% ethyl acetate in petroleum ether) to obtain compound 8 (2.3 g, 89%). TLC: PE:EA=5:1, 254 nm; $R_f$ (compound 7)=0.1; $R_f$ (compound 8)=0.6.

A mixture of compound 8 (1.3 g, 2.33 mmol, 1.0 eq) in hydrochloric acid (3 M in EA, 30 mL) was stirred at room temperature for 16 h. The reaction was monitored by TLC. Then the mixture was concentrated under reduced pressure. The residue was purified by silica gel chromatography (10-25% ethyl acetate in petroleum ether) to give compound AB17590 (502 mg, 61%) as a yellow solid. TLC: PE:EA=3:1, 254 nm; $R_f$ (compound 8)=0.8; $R_f$ (compound AB17590)=0.5; LC-MS: 359 (M+1)+; $^1$H NMR (400 MHz, $CDCl_3$) δ 8.12 (d, J=19.7 Hz, 2H), 7.94 (s, 1H), 7.42 (s, 1H), 7.35 (d, J=8.1 Hz, 1H), 7.13 (t, J=7.8 Hz, 1H), 7.04 (d, J=8.2 Hz, 1H), 6.93 (dd, J=15.7, 8.6 Hz, 2H), 5.04 (d, J=9.1 Hz, 1H), 3.95 (s, 3H), 2.45 (s, 3H), 1.42 (d, J=8.4 Hz, 1H), 0.78-0.68 (m, 1H), 0.62 (d, J=4.8 Hz, 1H), 0.54-0.41 (m, 2H).

Synthesis of AB17653

Figure 6B:
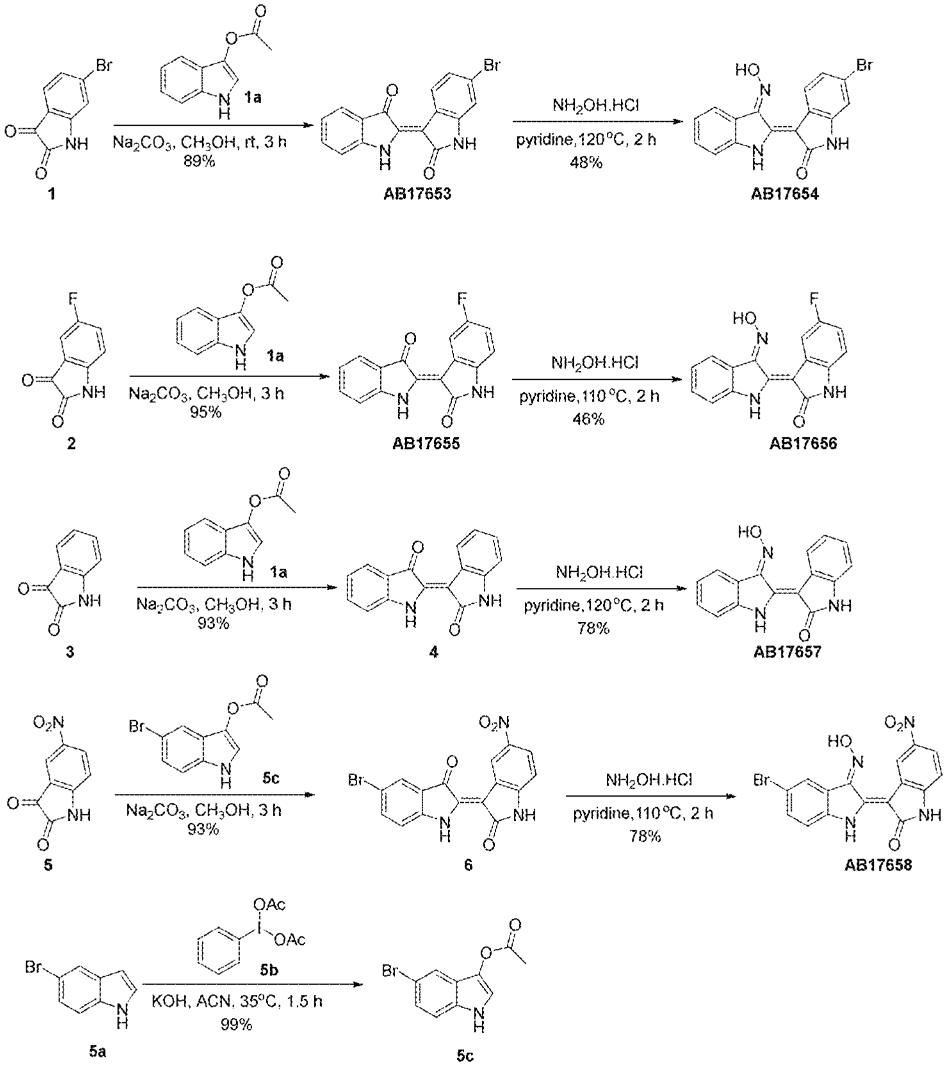

As shown in FIG. 6B, a mixture of compound 1 (721 mg, 3.20 mmol, 1.0 eq), compound 1a (560 mg, 3.20 mmol, 1.0 eq) and sodium carbonate (866 mg, 8.17 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound AB17653 (979 mg, 89%) as a red solid. TLC: PE/EA=3/1, 254 nm; $R_f$ (Compound 1)=0.6; $R_f$ (Compound AB17653)=0.4; LC-MS: 338.95 $(M-1)^-$; $^1$H NMR (400 MHz, d6-DMSO) δ11.01 (d, J=21.5 Hz, 2H), 8.64 (d, J=8.3 Hz, 1H), 7.62 (d, J=7.7 Hz, 1H), 7.55 (t, J=7.6 Hz, 1H), 7.39 (d, J=8.1 Hz, 1H), 7.18 (d, J=8.4 Hz, 1H), 7.00 (dd, J=8.8, 4.6 Hz, 2H).

Synthesis of AB17654

As shown in FIG. 6B, a mixture of compound AB17653 (979 mg, 2.88 mmol, 1.0 eq) and hydroxylamine hydrochloride (520 mg, 7.49 mmol, 2.6 eq) in pyridine (30 mL) was stirred at 120° C. for 2 h under nitrogen atmosphere. The progress of the reaction mixture was monitored by LCMS. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17654 (500 mg, 48%) as a red solid. LC-MS: 357.95 $(M+1)^+$; $^1$H NMR (400 MHz, d6-DMSO) δ 13.59 (s, 1H), 11.71 (s, 1H), 10.82 (s, 1H), 8.53 (d, J=8.4 Hz, 1H), 8.19 (d, J=7.7 Hz, 1H), 7.42-7.35 (m, 2H), 7.11-6.96 (m, 3H).

Synthesis of AB17655

As shown in FIG. 6B, a mixture of compound 2 (637 mg, 3.86 mmol, 1.0 eq), compound 1a (676 mg, 3.86 mmol, 1.0 eq) and sodium carbonate (1044 mg, 9.84 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound AB17655 (1027 mg, 95%) as a red solid. LC-MS: 281.05 $(M+1)^+$; $^1$H NMR (400 MHz, d6-DMSO) δ11.06 (s, 1H), 10.86 (s, 1H), 8.54 (dd, J=10.5, 2.7 Hz, 1H), 7.67-7.53 (m, 2H), 7.41-7.38 (m, 1H), 7.09-6.98 (m, 2H), 6.85 (dd, J=8.5, 4.8 Hz, 1H).

Synthesis of AB17656

As shown in FIG. 6B, a mixture of compound AB17655 (1027 mg, 3.67 mmol, 1.0 eq) and hydroxylamine hydrochloride (663 mg, 9.54 mmol, 2.6 eq) in pyridine (30 mL) was stirred at 110° C. for 2 h under nitrogen atmosphere. The progress of the reaction mixture was monitored by LCMS. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17656 (500 mg, 48%) as a red solid. LC-MS: 296.00 $(M+1)^+$; $^1$H NMR (400 MHz, d6-DMSO) δ13.60 (s, 1H), 11.77 (s, 1H), 10.69 (s, 1H), 8.43 (s, 1H), 8.20 (d, J=7.7 Hz, 1H), 7.39 (d, J=5.7 Hz, 2H), 7.02 (s, 1H), 6.91 (s, 1H), 6.83 (d, J=4.9 Hz, 1H).

Synthesis of AB17657

As shown in FIG. 6B, a mixture of compound 3 (362 mg, 2.46 mmol, 1.0 eq), compound 1a (431 mg, 2.46 mmol, 1.0 eq) and sodium carbonate (666 mg, 6.28 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound 4 (606 mg, 93%). TLC: PE/EA=1/1, 254 nm; $R_f$ (Compound 3)=0.7; $R_f$ (Compound 4)=0.5.

A mixture of compound 4 (606 mg, 2.31 mmol, 1.0 eq) and hydroxylamine hydrochloride (418 mg, 6.01 mmol, 2.6 eq) in pyridine (20 mL) was stirred at 120° C. for 2 h under nitrogen atmosphere. The progress of the reaction mixture was monitored by TLC. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17657 (500 mg, 78%) as a brown solid. TLC: PE/EA=1/1, 254 nm; $R_f$ (Compound 4)=0.5; $R_f$ (Compound AB17657)=0.4; LC-MS: 278.10 $(M+1)^+$; $^1$H NMR (400 MHz, d6-DMSO) δ13.60 (s, 1H), 11.77 (s, 1H), 10.69 (s, 1H), 8.43 (s, 1H), 8.20 (d, J=7.7 Hz, 1H), 7.39 (d, J=5.7 Hz, 2H), 7.02 (s, 1H), 6.91 (s, 1H), 6.83 (d, J=4.9 Hz, 1H).

Synthesis of AB17658

As shown in FIG. 6B, a mixture of compound 5a (337 mg, 1.73 mmol, 1.0 eq), compound 5b (554 mg, 1.73 mmol, 1.0 eq) and potassium hydroxide (1114 mg, 3.46 mmol, 2.0 eq) in acetonitrile (10 mL) was stirred at 35° C. for 1.5 h under nitrogen atmosphere. The progress of the reaction mixture was monitored by TLC. After completion of the reaction, the mixture was concentrated under reduced pressure and the residue was purified by silica gel chromatography to afford compound 5c (436 mg, 99%). TLC: PE/EA=1/1, 254 nm; $R_f$ (Compound 5a)=0.8; $R_f$ (Compound 5c)=0.5.

A mixture of compound 5 (330 mg, 1.72 mmol, 1.0 eq), compound 5c (436 mg, 1.72 mmol, 1.0 eq) and sodium carbonate (465 mg, 4.38 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound 6 (617 mg, 93%). TLC: PE/EA=1/1, 254 nm; $R_f$ (Compound 5)=0.5; $R_f$ (Compound 6)=0.4.

A mixture of compound 6 (617 mg, 1.60 mmol, 1.0 eq) and hydroxylamine hydrochloride (290 mg, 4.17 mmol, 2.6 eq) in pyridine (20 mL) was stirred at 110° C. for 2 h under nitrogen atmosphere. The progress of the reaction mixture was monitored by TLC. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17658 (500 mg, 78%) as a red solid. TLC: PE/EA=1/1, 254 nm; $R_f$ (Compound 6)=0.4; $R_f$(Compound AB17658)=0.3; LC-MS: 402.95 $(M+1)^+$; $^1H$ NMR (400 MHz, d6-DMSO) δ11.86 (s, 1H), 11.39 (s, 1H), 9.40 (d, J=2.2 Hz, 1H), 8.33 (d, J=1.8 Hz, 1H), 8.06 (dd, J=8.6, 2.4 Hz, 1H), 7.59 (dd, J=8.4, 2.0 Hz, 1H), 7.43 (d, J=8.6 Hz, 1H), 7.02 (d, J=8.6 Hz, 1H).

Example 17

In Vivo Assessment of the Photoprotective Properties of Malassezin, Other *Malassezia*-Derived Compounds, and Chemical Analogs Thereof Malassezin 1% Formulation The Malassezin 1% formulation used in this study contained the following ingredients: Water (aqua)—65.939%; Dimethyl isosorbide—20.000%; Olive Oil Glycereth-8 Esters—3.000%; Glycerin—2.991%; Coconut Alkanes—2.700%; Hydroxyethyl Acrylate/Sodium Acryloyldimethyl Taurate Copolymer—1.700%; Malassezin—1.000%; Pentylene Glycol—1.000%; Phenoxyethanol—0.640%; Coco-Caprylate/Caprate—0.300%; Caprylyl Glycol—0.200%; Chlorphenesin—0.160%; Sorbitan Isostearate—0.140%; Tocopherol—0.100%; Polysorbate 60-0.080%; and Disodium EDTA—0.050%.

Experimental Design

A 39-year-old Skin Type IV female was included in this Proof of Concept study.

Figure 7:
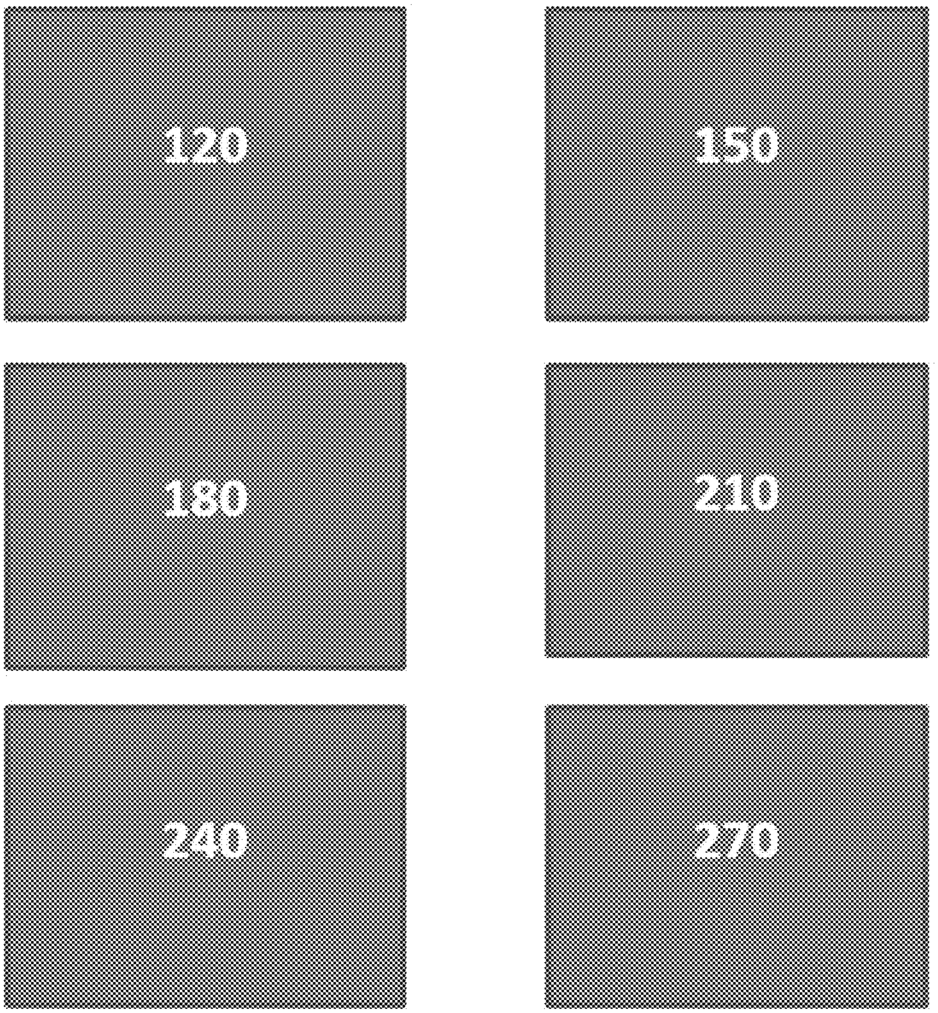
FIG. 7 is a schematic showing a skin treatment template for Skin Type IV patients. Values indicate UV dose for a given area in mJ/cm$^2$.

On Day 1 of the experiment, the subject was evaluated to determine Minimal Erythema Dosing ("MED") using a targeted broad band Dualight UVB device. A template of 6 squares was placed on the lower left back (1.5 cm×1.5 cm) of the test subject. See FIG. 7.

Figure 12:
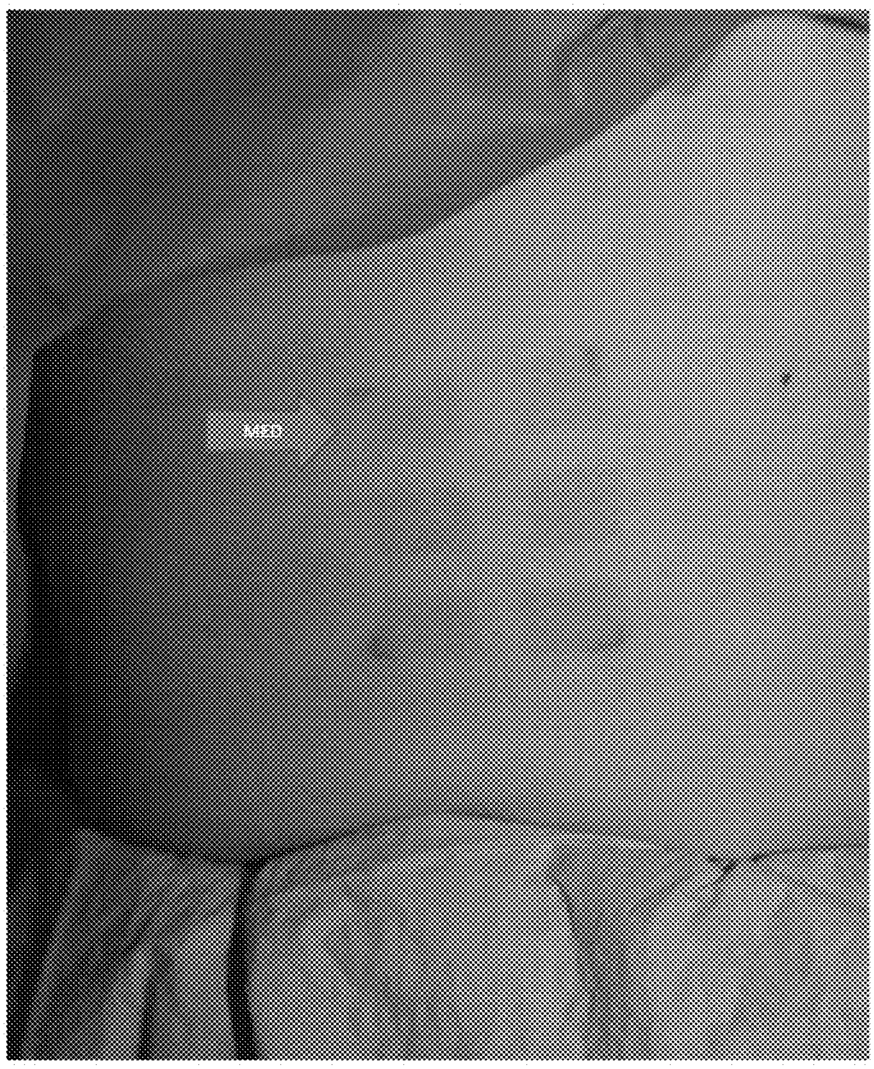
FIG. 12 is a photograph showing a subject's skin 24 hours after irradiation with various levels of UV according to the skin treatment template shown in FIG. 7. The minimal erythema dose ("MED") was 120 mJ UVB 24 hours after irradiation.

The MED photo test doses for the subject's skin type are listed in FIG. 8 in mJ/$cm^2$ units. Twenty-four hours after irradiation, the subject returned for MED assessment. As shown in FIG. 12, the subject's MED was 120 mJ.

Figure 13:
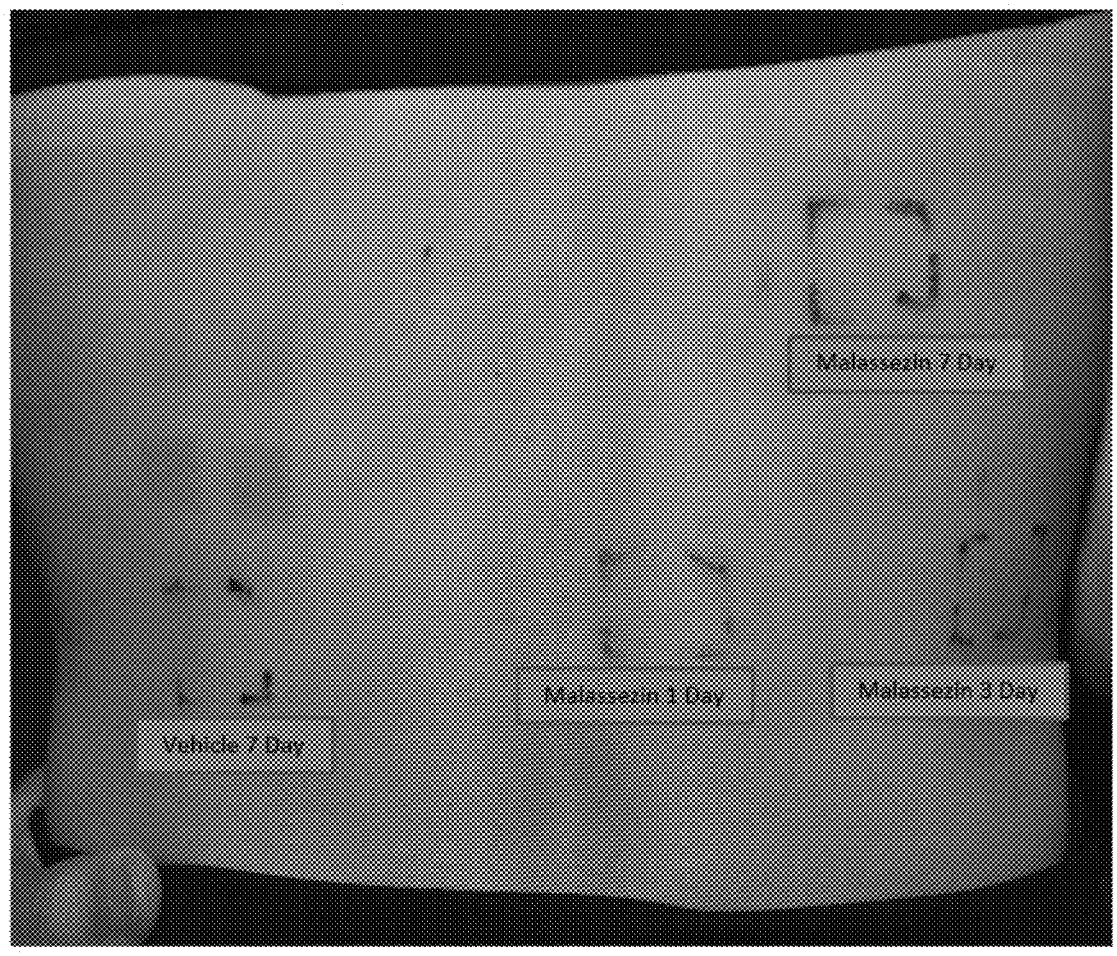
FIG. 13 is a photograph showing test sites on a subject's skin at Day 7.

Subsequently, the subject applied Malassezin 1% in the superior test square of the right back twice daily for 7 days. A second right lower square was treated twice daily from day 4 to day 7, and a third medial square for one application on day 7. The product vehicle was applied for 7 days twice daily on the left back. See FIG. 13. The subject returned to the research center for irradiation on day 7. See FIG. 9. Each test site was irradiated with 120 mJ of UVB exposure. The subject returned in 24 hours for assessment of phototoxicity/photoprotection. See FIG. 14.

Figure 15:
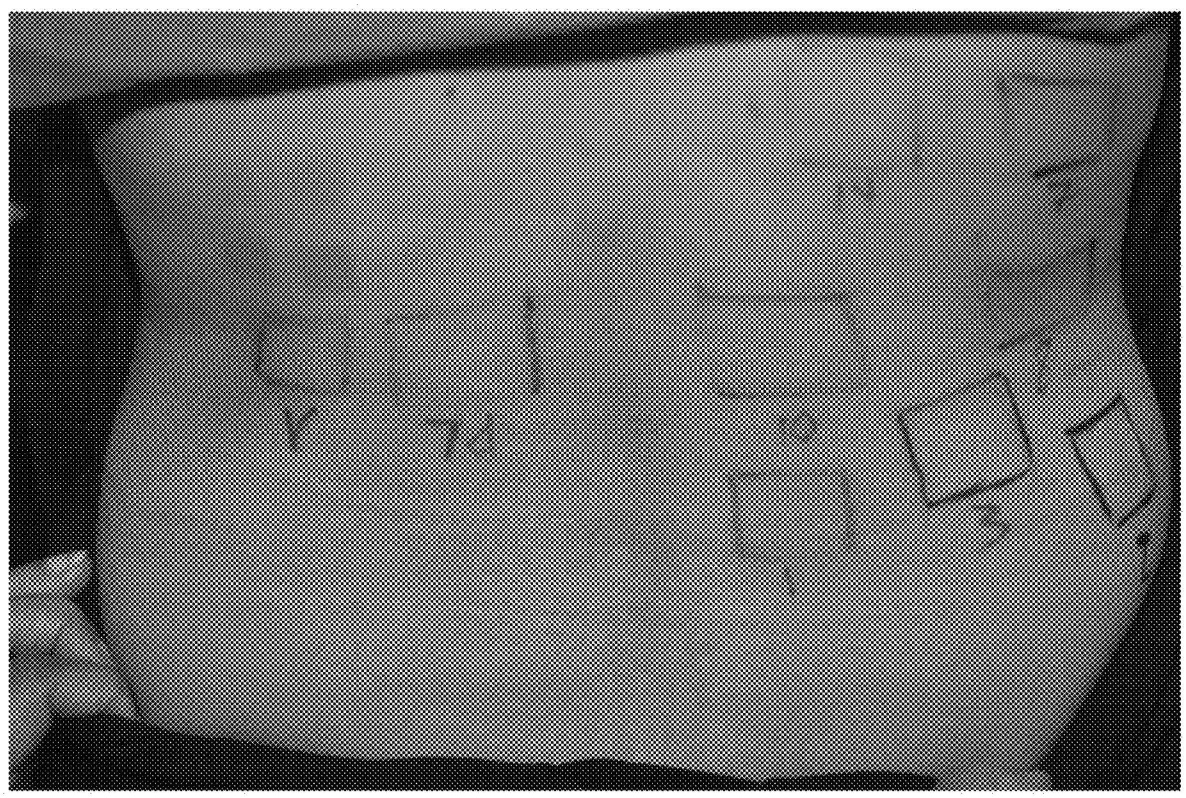
FIG. 15 is a photograph showing test sites on a subject's skin at Day 14 after an additional week of Malassezin therapy. Treatment areas were dosed with 120 mJ UVB.
Figure 16:
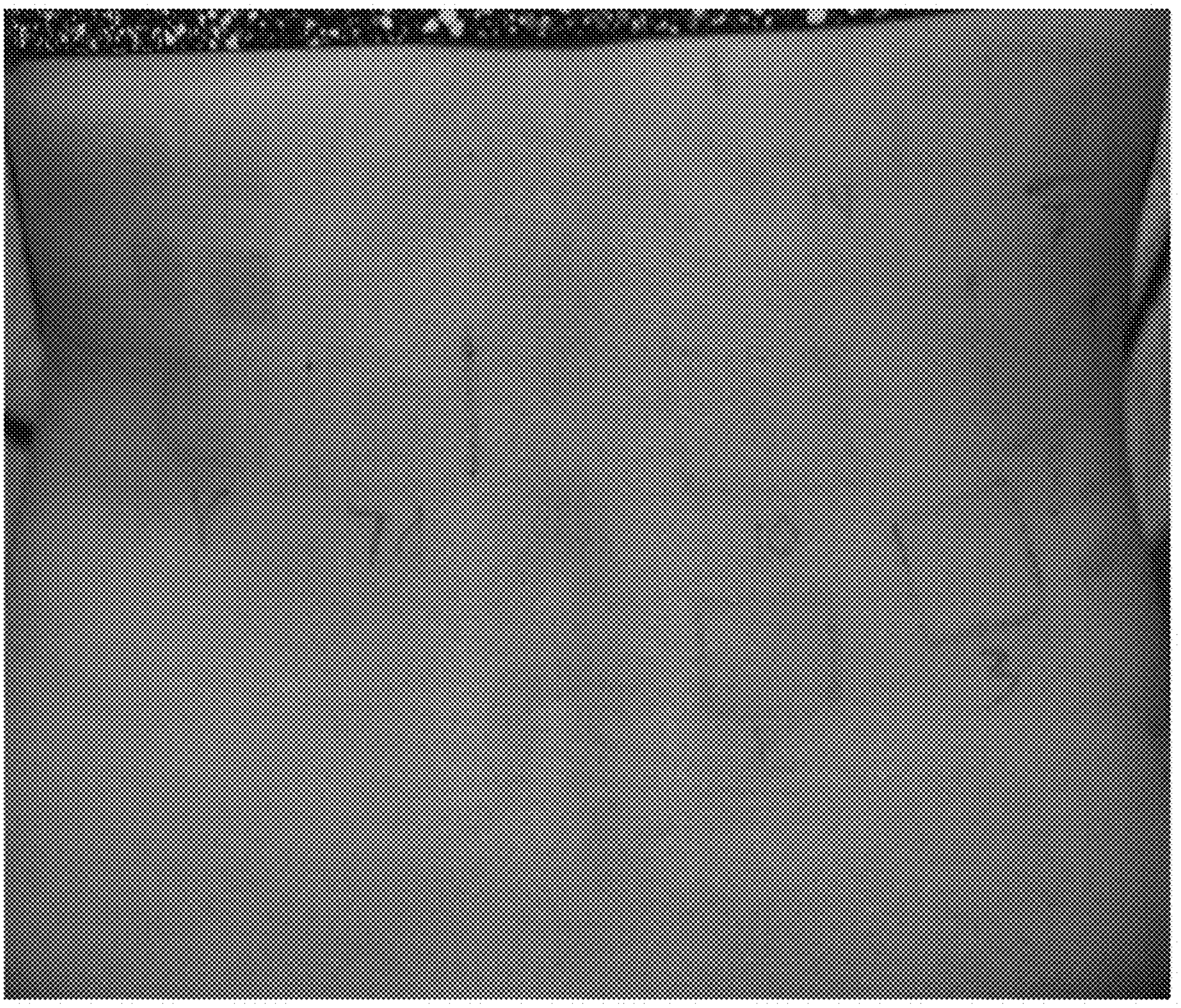
FIG. 16 is a photograph showing test sites on a subject's skin at Day 15, 24 hours post-irradiation with 120 mJ UVB. Note erythema at vehicle site for Days 7 and 9. Also note minimal to mild erythema at Malassezin 1%-treated sites for Day 14, 10, and 8, with trace erythema at Days 1 and 3.

The subject continued the experiment, receiving Malassezin 1% for a total of 14 days. FIGS. 15-16 show regions of the subject's skin exposed to the following treatments: on site 14, Malassezin 1% was applied twice a day for 14 days; on site 10, Malassezin 1% was applied twice a day for 11 days; on site 8, Malassezin 1% was applied twice a day for 8 days; on site 3, Malassezin 1% was applied twice a day for 3 days; on site 1, Malassezin 1% was applied once; and, on the vehicle sites, vehicle was applied twice a day for 7 and 9 days, respectively.

Results

Figure 14:
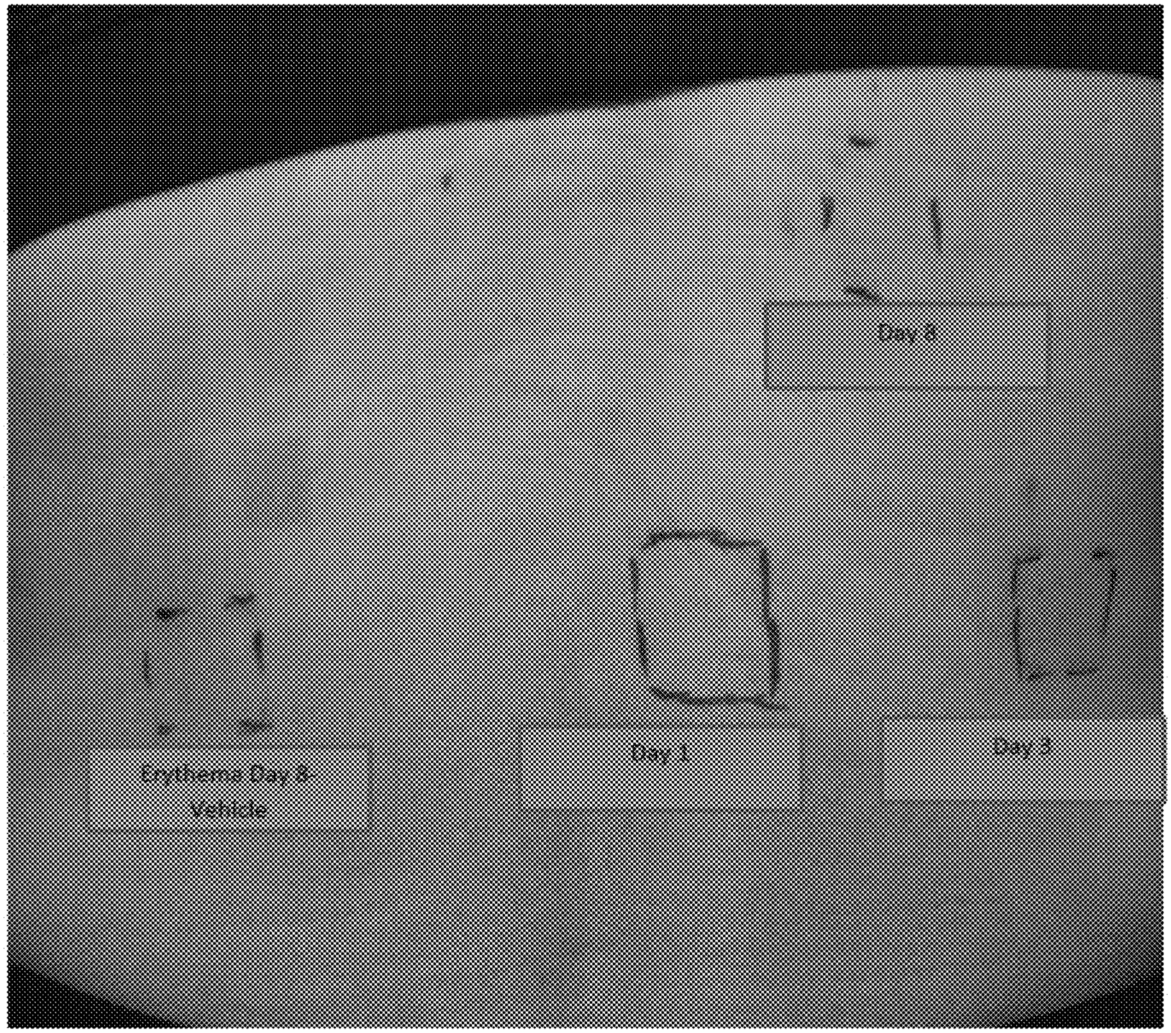
FIG. 14 is a photograph showing test sites on a subject's skin at Day 8, 24 hours post-irradiation with 120 mJ UVB.

As shown in FIG. 14, 24 hours after UVB exposure, the subject exhibited 1 plus to 2 plus erythema at the vehicle test site. See FIG. 11 for erythema scale. In contrast, there was less erythema (mild) noted at the Malassezin 1% 7-day treatment site. Evaluation of sites treated for 3 days showed minimal erythema and none for the 1-day application site. Colorimetry measurements were taken from each site using the Mexameter MX16 and supported clinical observations. Maximal erythema readings were observed in the vehicle site followed by the Malassezin 7-day-treated site. The lowest values were observed for the Malassezin day 3 and day 1 site, respectively. See FIG. 9.

The subject continued the experiment and returned for a repeat UVB irradiation at 14 days with interpretation at day 15. See FIG. 15. Clinical evaluation at day 15 revealed moderate erythema at the vehicle site for day 7 and significantly less at day 9. See FIG. 16. Less erythema (mild) was noted at the Malassezin 1%-treated sites, including the day 14, day 10, and day 8 sites Minimal erythema was noted at Malassezin 1% sites for days 1 and day 3. Colorimetry readings were taken from each site to measure erythema and the melanin index. Results supported clinical observations of less erythema at the Malassezin 1%-treated sites. See FIG. 10.

Biopsies were taken from the vehicle site at 9 days and the Malassezin 1%-treated sites for days 1 and 3. Specimens were analyzed for Hematoxylin and Eosin, Fontana Masson staining and MART I for quantification of melanocytes and affymetrix studies.

Diagnosis: (A) Skin—Day 1 Treated (Malassezin 1%): Basket weave stratum corneum, normal appearing melanocytes (confirmed by immunoperoxidase staining with Mart-1), and epidermal melanin (confirmed by immunoperoxidase staining with Fontana Masson).

Diagnosis: (B) Skin—Day 3 Treated (Malassezin 1%): Basket weave stratum corneum, less dendritic melanocytes (confirmed by immunoperoxidase staining with MART-1/Melan A) when compared to C and D, and with a slight decrease in epidermal melanin, as skip areas (confirmed by immunoperoxidase staining with Fontana Masson).

Diagnosis: (C) Skin—Vehicle: Normal appearing epidermal melanocytes (confirmed by immunoperoxidase staining with Mart-1) and epidermal melanin (confirmed by immunoperoxidase staining with Fontana Masson).

Diagnosis: (D) Skin—Normal: Normal appearing epidermal melanocytes (confirmed by immunoperoxidase staining with Mart-1) and epidermal melanin (confirmed by immunoperoxidase staining with Fontana Masson).

Conclusions

The results of this Proof of Concept study demonstrate the UV-protective properties of Malassezin.

It is envisioned that further studies involving additional patients will demonstrate equivalent or more effective UV-protective properties of Malassezin. It also is envisioned that additional studies will elucidate molecular signaling pathways associated with Malassezin-induced photoprotection.

DOCUMENTS

Berridge, M. V., Tan, A. S., McCoy, K. D., Wang, R. The Biochemical and Cellular Basis of Cell Proliferation Assays That Use Tetrazolium Salts. Biochemica 4:14-19 (1996).

Black, et al. Athymic Nude Mice and Human Skin Grafting. In: Maibach, et al. (eds.). Models in Dermatology Vol. 1. Karger, Basel, 1985, 228-39.

Costin, G.-E., Raabe, R. Optimized in vitro pigmentation screening assay using a reconstructed three dimensional human skin model. Rom. J. Biochem. 50 (1), 15-27 (2013).

Donato, et al. A Microassay for Measuring Cytochrome P450IA1 and P450IIB1 Activities in Intact Human and Rat Hepatocytes Cultured on 96-Well Plates. Anal Biochem. 1993; 213(1):29-33.

Elmore. Apoptosis: A Review of Programmed Cell Death Toxicologic Pathology 2007; 35:495-516.

Fitzpatrick, et al. The Validity and Practicality of Sun-Reactive Skin Types I Through VI. Arch Dermatol. 1988; 124(6):869-871.

Gaitanis, et al. Skin Diseases Associated With *Malassezia* Yeasts: Facts and Controversies. Clinics in Dermatology 2013; 31:455-463.

Gambichler, et al. Quantification of Ultraviolet Protective Effects of Pityriacitrin in Humans Archives of Dermatological Research 2007; 299(10):517-520.

Guého, et al. The Genus *Malassezia* With Description of Four New Species. Antonie Van Leeuwenhoek 1996; 69:337-55.

Karchner, et al. Identification and Functional Characterization of Two Highly Divergent Aryl Hydrocarbon Receptors (AHR1 and AHR2) in the Teleost *Fundulus heteroclitus*. The Journal of Biological Chemistry 1999; 274 (47):33814-24.

Krämer, et al. Malassezin, A Novel Analyst of the Aryl Hydrocarbon Receptor From The Yeast *Malassezia furfur*, Induces Apoptosis in Primary Human Melanocytes. ChemBioChem 2005; 6:860-5.

Lee, et al. Comparison of Gene Expression Profiles Between Keratinocytes, Melanocytes and Fibroblasts. Ann Dermatol. 2013; 25(1):35-45.

Machowinski, et al. Pityriacitrin-A Potent UV filter Produced by *Malassezia furfur* and its Effect on Human Skin Microflora. Mycoses 2006; 49(5):388-392.

Manning, et al. Maintenance of Skin Xenografts of Widely Divergent Phylogenetic Origin on Congenitally Athymic (Nude) Mice. J Exp Med 1973; 138:488-94.

Mayser, et al. Pityriacitrin—An Ultraviolet-Absorbing Indole Alkaloid from the Yeast *Malassezia furfur*. Archives of Dermatological Research 2002; 294(3):131-134.

Mayser, et al. Pityrialactone-A New fluorochrome from the Tryptophan Metabolism of *Malassezia furfur*. Antonie van Leeuwenhoek 2003; 84(3):185-191.

Nazzaro-Porro, et al. Identification of Tyrosinase Inhibitors in Cultures of *Pityrosporum*. The Journal of Investigative Dermatology 1978; 71:205-208.

Noakes. The Aryl Hydrocarbon Receptor: A Review of Its Role in the Physiology and Pathology of the Integument and Its Relationship to the Tryptophan Metabolism. Journal of Tryptophan Research 2015; 8: 17-18.

Otulakowski, et al. Use of a Human Skin-Grafted Nude Mouse Model for the Evaluation of Topical Retinoic Acid Treatment. J Invest Dermatol 1994; 102:515-8.

Park, J. I., Lee, H. Y., Lee, J. E., Myung, C. H., Hwang, J S Inhibitory effect of 2-methyl-naphtho[1,2,3-de]quinolin-8-one on melanosome transport and skin pigmentation. Sci. Rep. July 6:6:29189. Doi: 10.1038/srep29189 (2016).

Plenat, et al. Host-Donor Interactions in Healing of Human Split-Thickness Skin Grafts Onto Nude Mice: In Situ Hybridization, Immunohistochemical and Histochemical Studies. Transplantation 1992; 53:1002-10. Reed, et al. Long-Term Maintenance of Normal Human Skin on Congenitally Athymic (Nude) Mice. Proc Soc Exp Biol Med 1973; 143:350-3.

Scott, et al. The Permeability of Grafted Human Transplant Skin in Athymic Mice. J Pharm Pharmacol 1988; 40:128-9.

Song, et al. A Ligand For The Aryl Hydrocarbon Receptor Isolated From Lung. PNAS 2002; 99(23):14694-9.

Taylor, et al. The Taylor Hyperpigmentation Scale: a new visual assessment tool for the evaluation of skin color and pigmentation. Cutis. 2005 October; 76(4):270-4.

Wang, et al. Stress-Induced RNASET2 Overexpression Mediates Melanocyte Apoptosis Via The TRAF2 Pathway In Vitro. Cell Death and Disease 2014; 5:e1022

Wasmeier, et al. Melanosomes At A Glance. Journal of Cell Science 2008; 121:3995-3999.

Wille, et al. Malassezin—A Novel Agonist of the Arylhydrocarbon Receptor From The Yeast *Malassezia furfur*. Bioorganic & Medicinal Chemistry 2001; 9:955-60.

Winston-McPherson, et al. Synthesis and Biological Evaluation of 2,3'-diindolylmethanes as Agonists of Aryl Hydrocarbon Receptor. Bioorganic & Medicinal Chemistry Letters 2014; 24:4023-4025.

Whyte, et al. Ethoxyresorufin-O-deethylase (EROD) Activity in Fish As A Biomarker of Chemical Exposure. Critical Reviews in Toxicology 2000; 30(4):347-570.

Yamaguchi, et al. Melanocytes and Their Diseases. Cold Spring Harb Perspect Med 2014; 4:a017046.

Zonios, et al. Skin Melanin, Hemoglobin, and Light Scattering Properties can be Quantitatively Assessed In Vivo Using Diffuse Reflectance Spectroscopy. J Invest Dermatol. 2001; 117:1452-1457.

Zhang, et al. Environmental Adaptability for Quorum Sensing: Regulating Iron Uptake During Biofilm Formation in *Paracoccus* Denitrifications. Applied and Environmental Microbiology, AEM. 00865-18 (2018).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A composition comprising one or more compounds selected from the group consisting of:

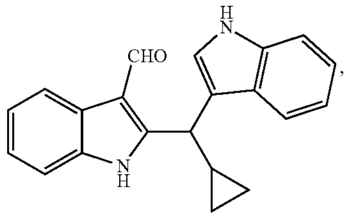
,

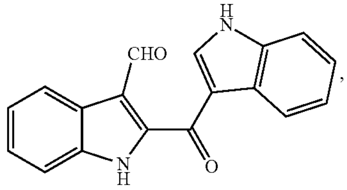
,

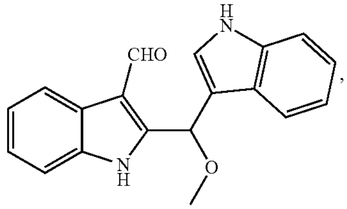
,

-continued
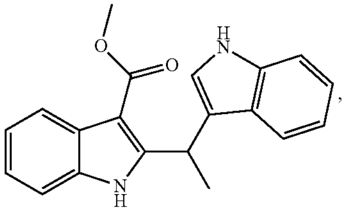
,
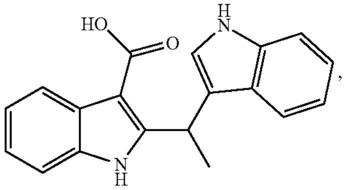
,
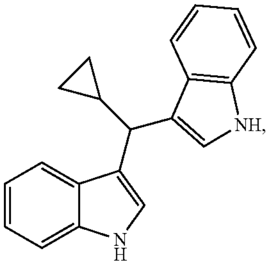
,
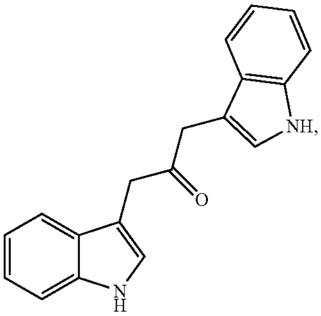
,
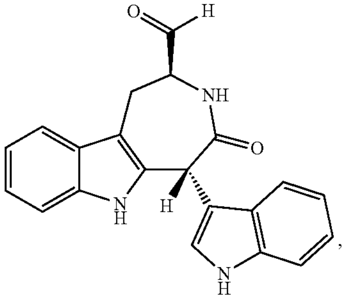
,
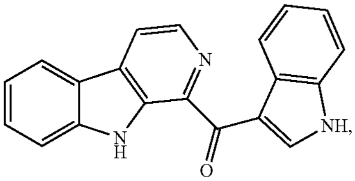
,
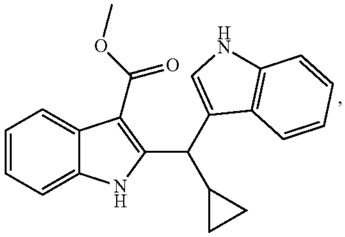
,
-continued
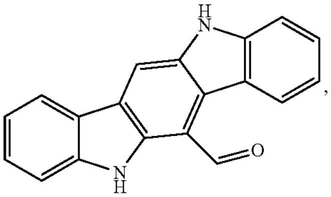
,
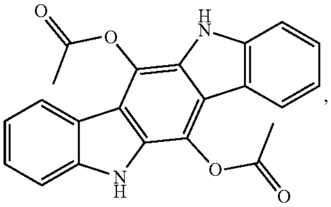
,
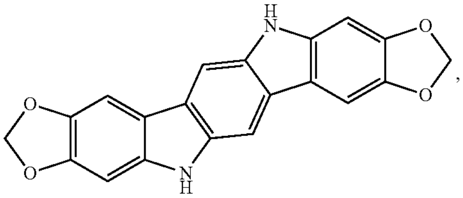
,
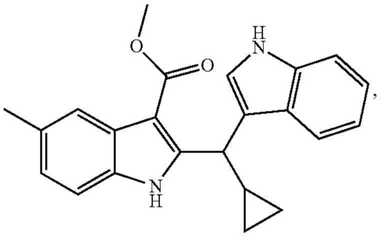
,
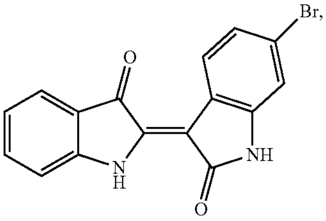
,
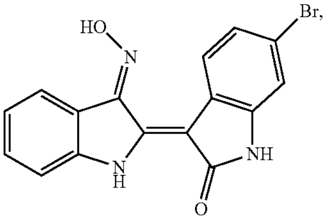
,
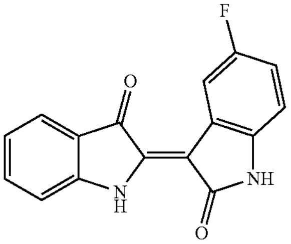
, -continued
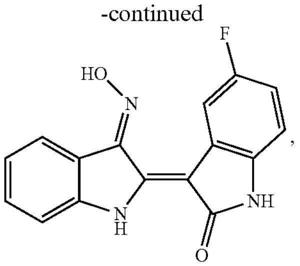
,
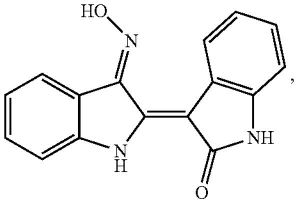
,
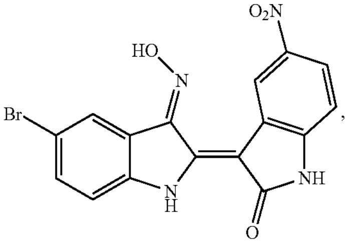
,
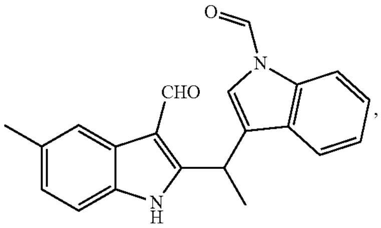
,
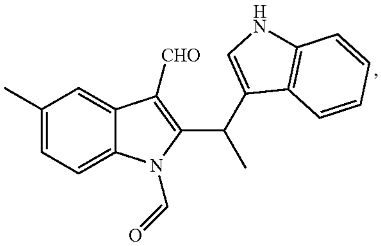
,
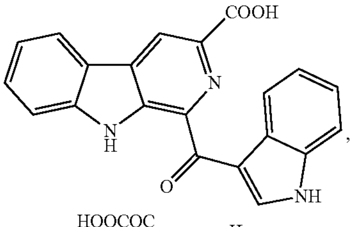
,
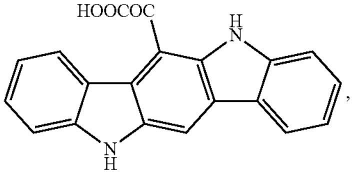
,
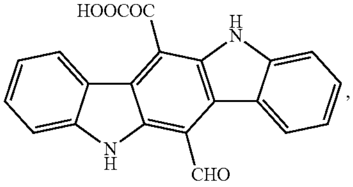
,
-continued
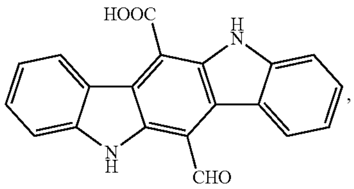
,
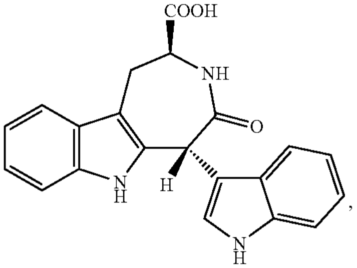
,
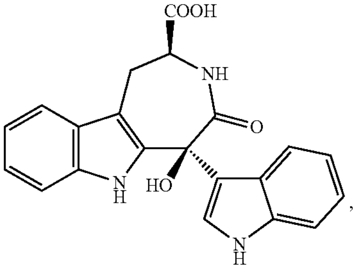
,
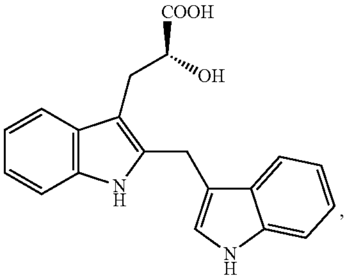
,
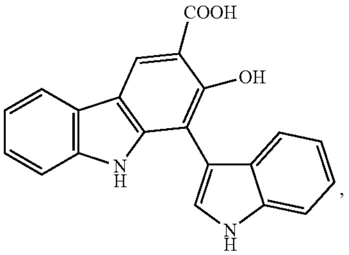
,
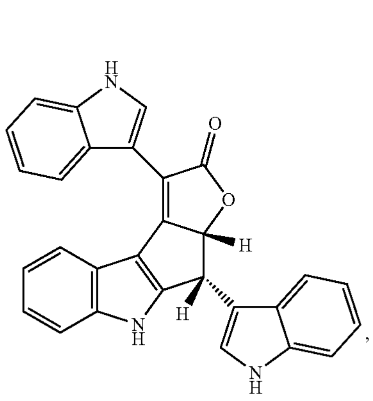
, -continued
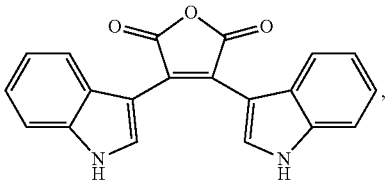
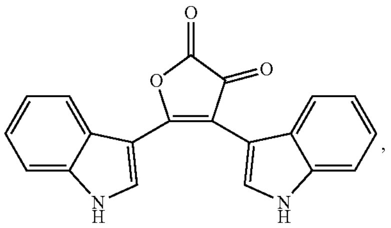
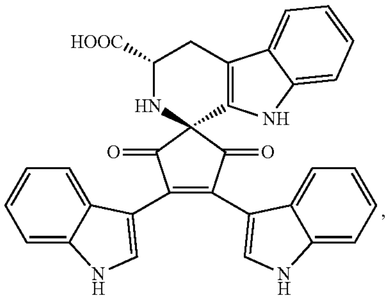
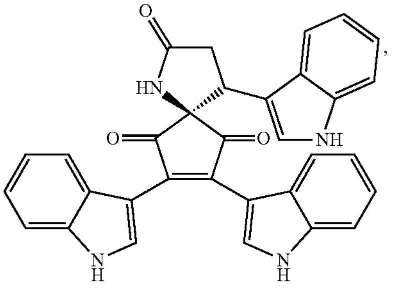
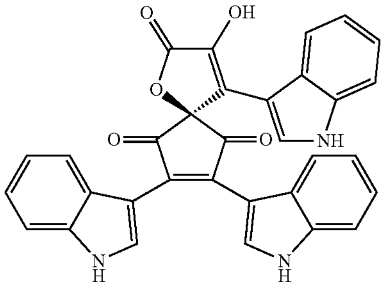
and
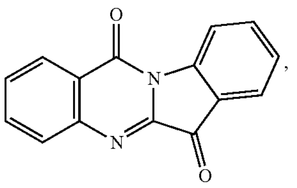
or a crystalline form, hydrate, or pharmaceutically or cosmetically acceptable salt thereof, and a cosmetically or pharmaceutically acceptable vehicle, diluent or carrier.
2. The composition of claim 1, wherein the composition comprises a compound selected from the group consisting of:
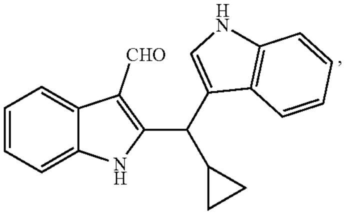
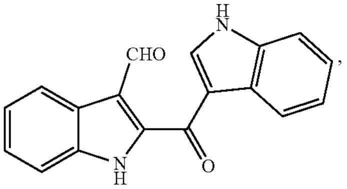
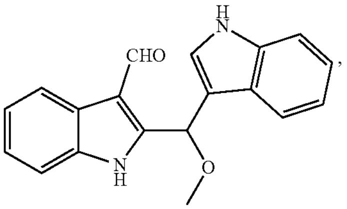
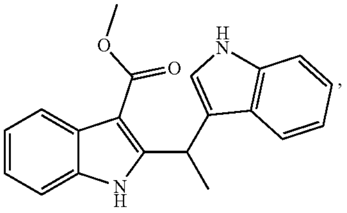
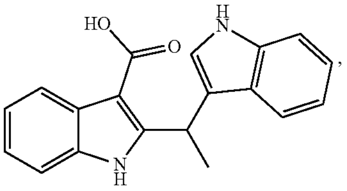
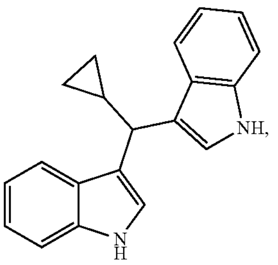
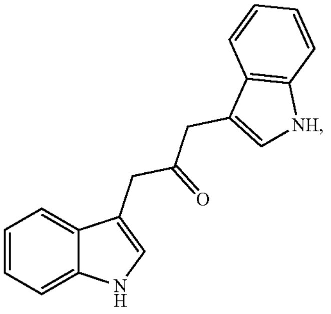

-continued
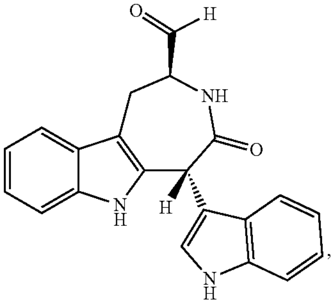
,
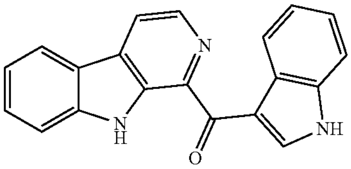
,
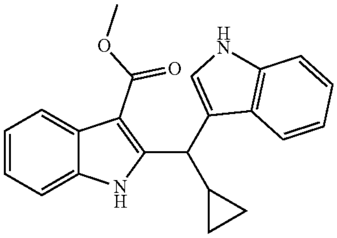
,
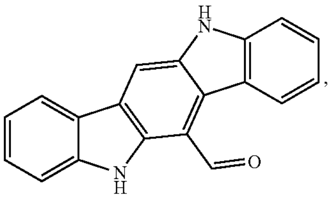
,
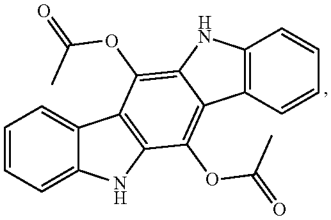
,
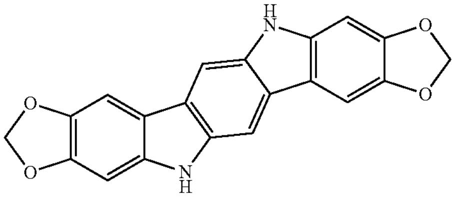
,
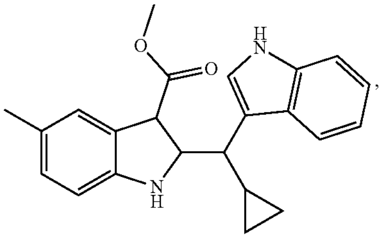
,
-continued
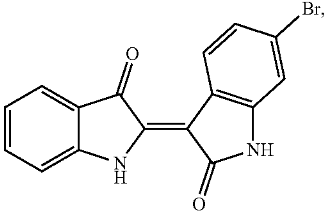
,
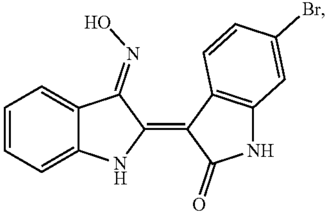
,
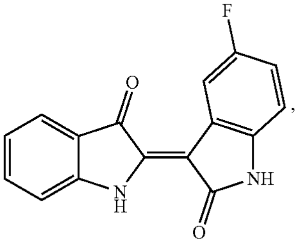
,
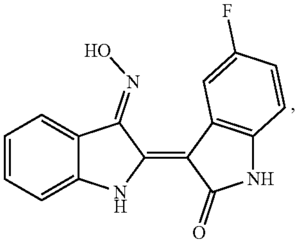
,
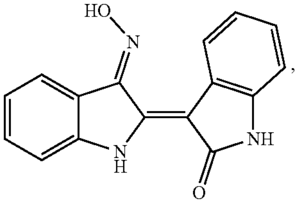
,
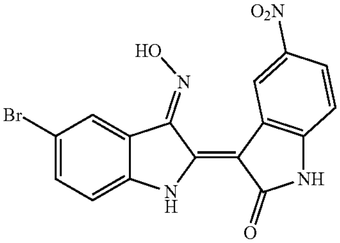
,
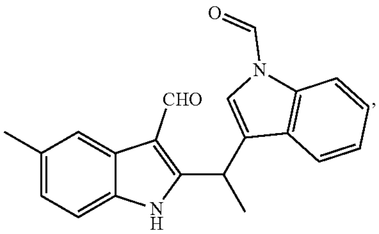
, -continued
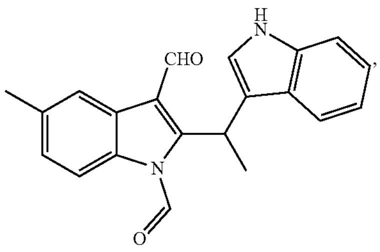
,
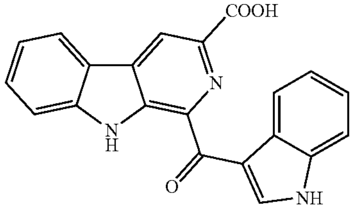
,
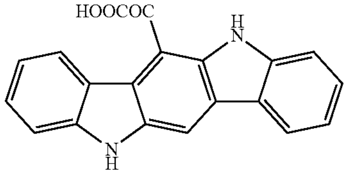
,
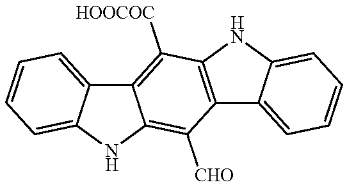
,
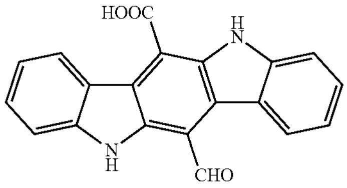
,
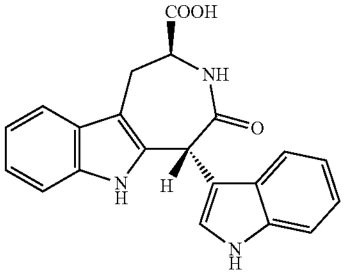
,
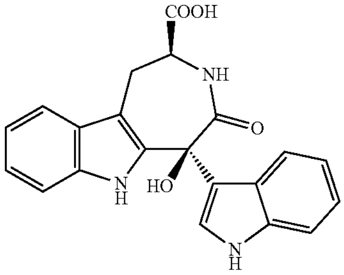
,
-continued
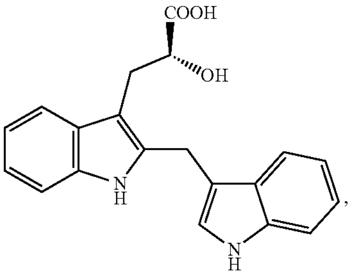
,
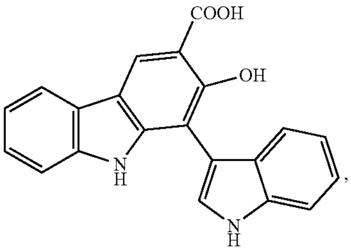
,
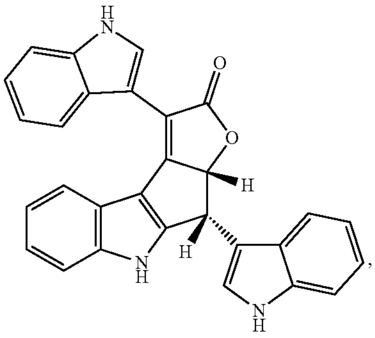
,
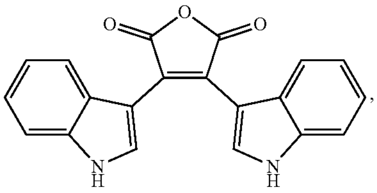
,
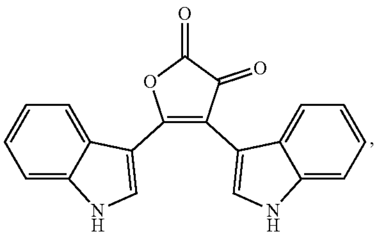
,
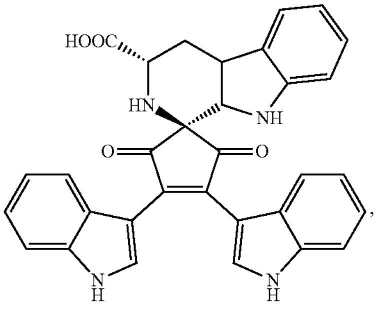
, -continued
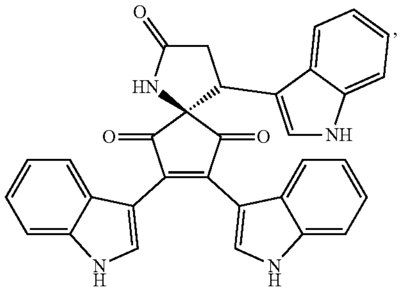,
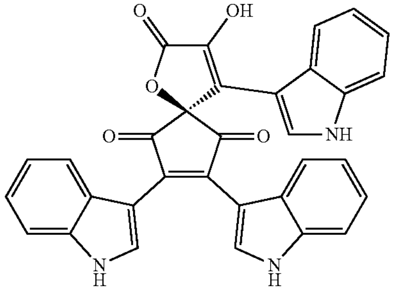
and
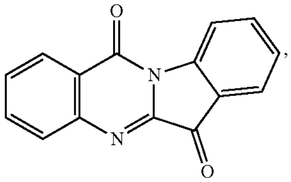,
or a crystalline form, hydrate, or pharmaceutically or cosmetically acceptable salt thereof, and a cosmetically or pharmaceutically acceptable vehicle, diluent or carrier.
3. The composition of claim 1, wherein the composition comprises a compound selected from the group consisting of:
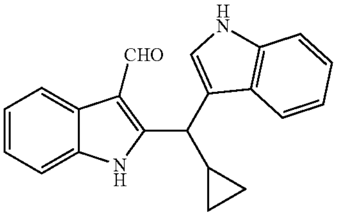,
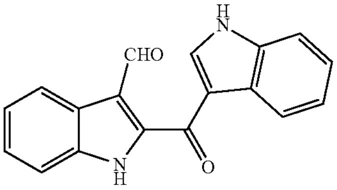,
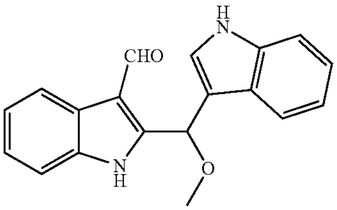,
-continued
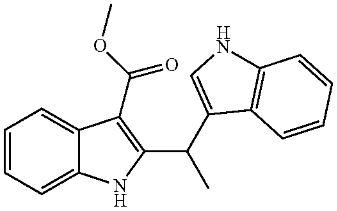,
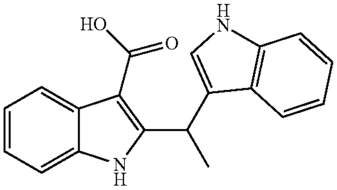,
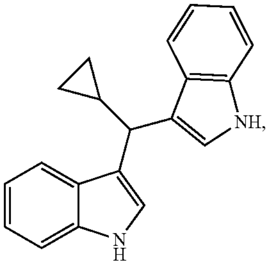
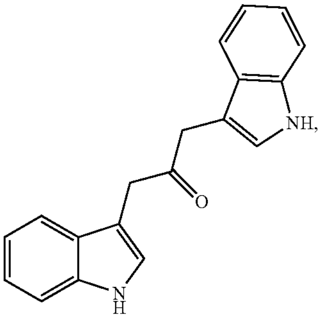
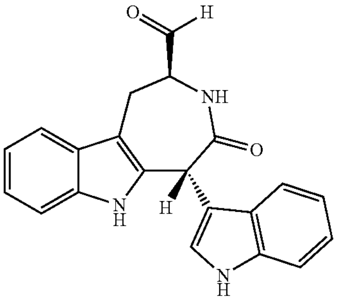,
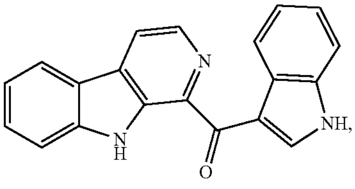
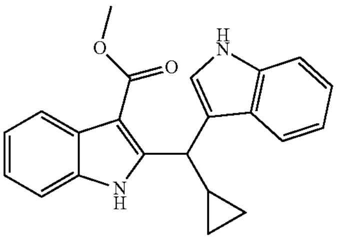, -continued
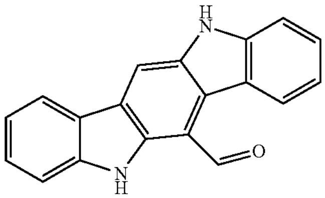
,
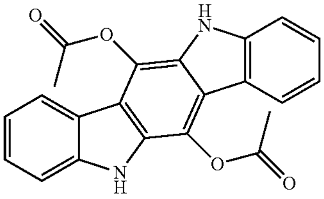
,
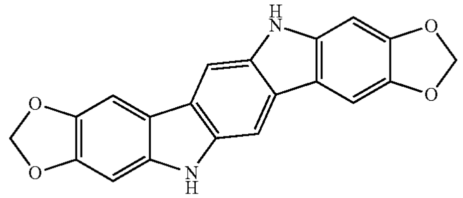
,
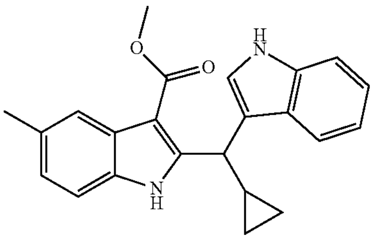
,
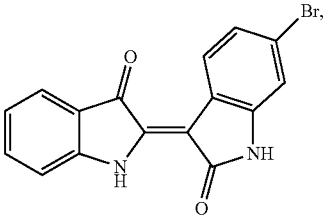
,
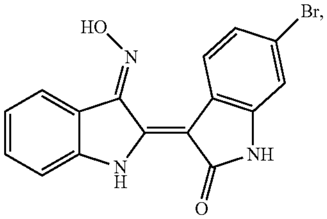
,
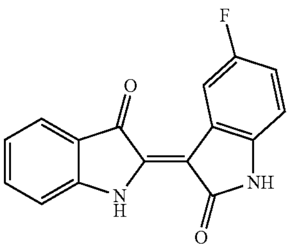
,
-continued
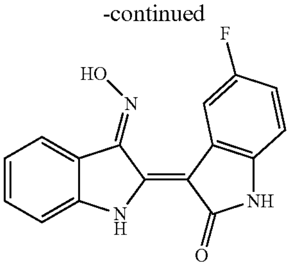
,
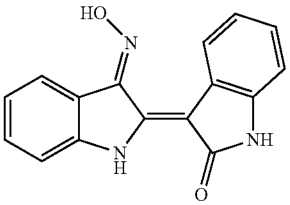
,
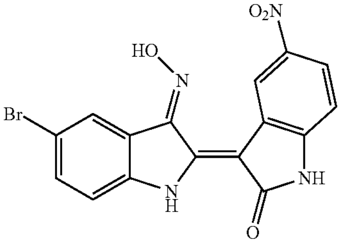
,
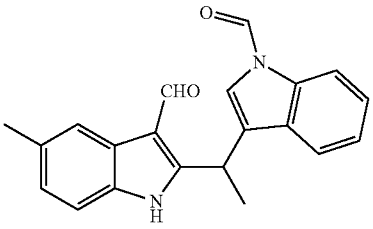
,
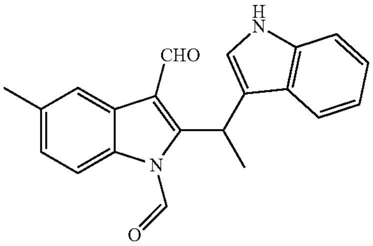
,
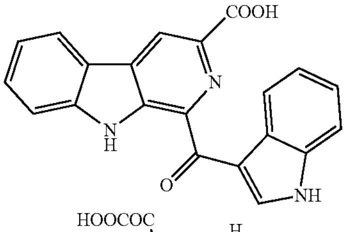
,
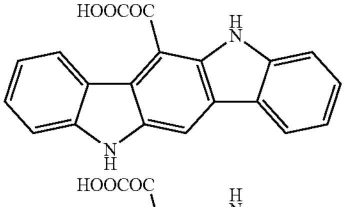
,
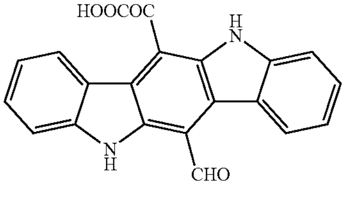
, -continued
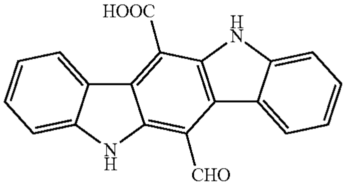
,
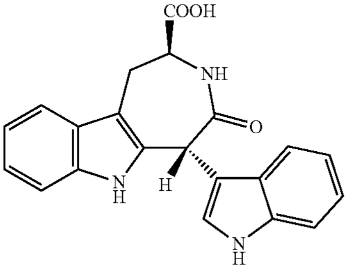
,
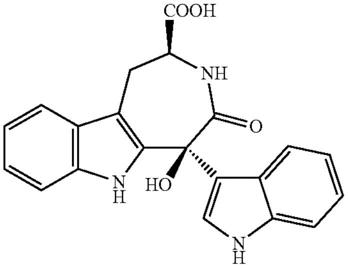
,
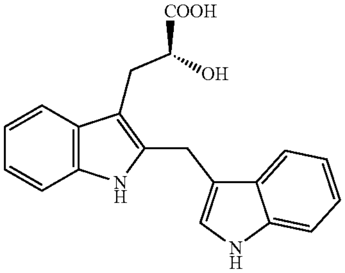
,
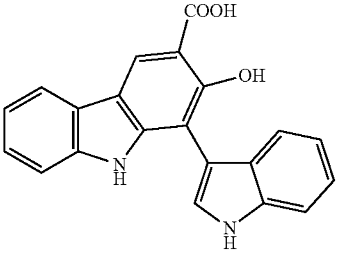
,
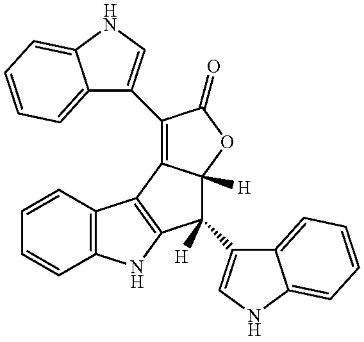
,
-continued
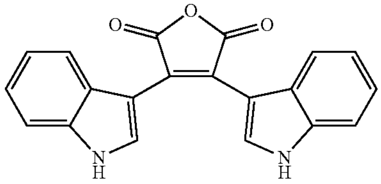
,
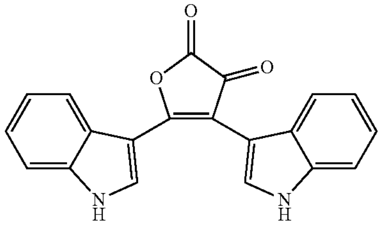
,
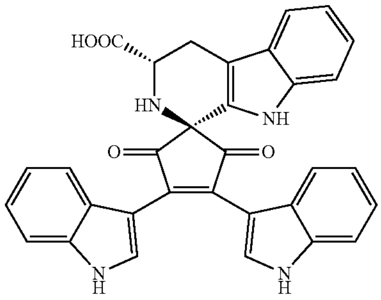
,
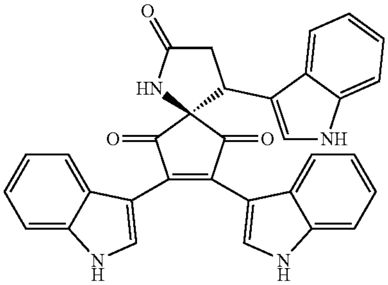
,
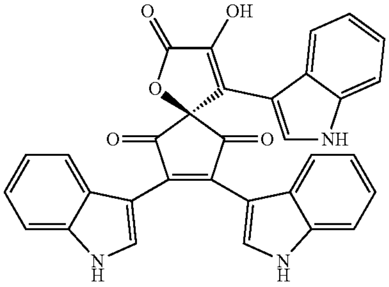
and
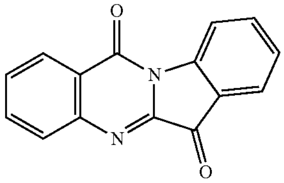
,
or a pharmaceutically or cosmetically acceptable salt thereof, and a cosmetically or pharmaceutically acceptable vehicle, diluent or carrier.

4. The composition of claim 1, wherein the composition comprises a compound selected from the group consisting of:

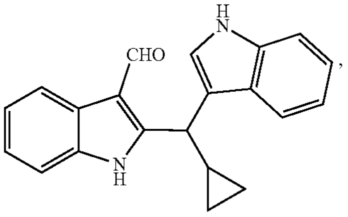

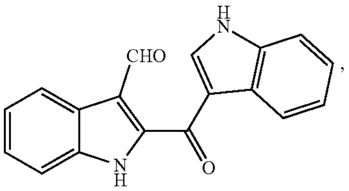

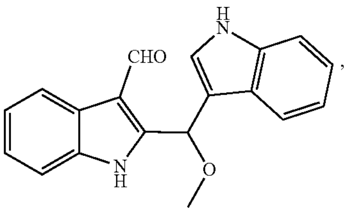

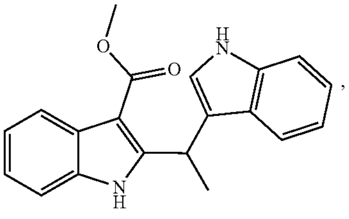

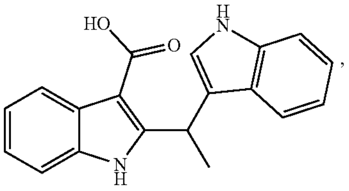

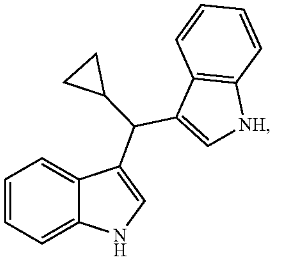

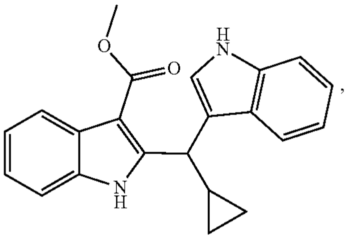

-continued

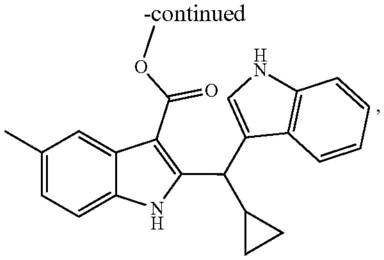

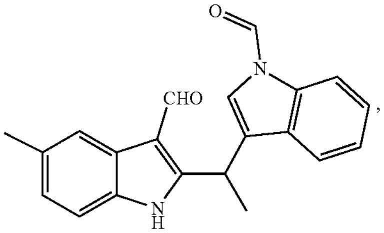

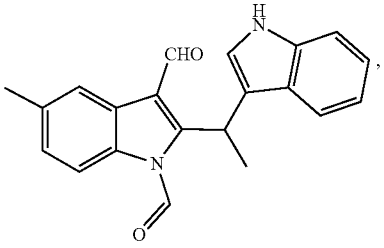

or a pharmaceutically or cosmetically acceptable salt thereof, and a cosmetically or pharmaceutically acceptable vehicle, diluent or carrier.

5. The composition of claim 1, wherein the composition comprises a compound of the following structure:

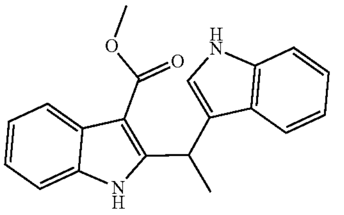 [SMILES: COC(=O)c1c(C(C)c2c[nH]c3ccccc23)[nH]c2ccccc12]

or a pharmaceutically or cosmetically acceptable salt thereof, and a cosmetically or pharmaceutically acceptable vehicle, diluent or carrier.

6. The composition of claim 5, wherein the composition further comprises one or more of a perfume, a pigment, estrogen, vitamin A, vitamin C, vitamin E, alpha-hydroxy or alpha-keto acids, lanolin, vaseline, aloe vera, methyl paraben, and propyl paraben.

7. The composition of claim 5, wherein the composition is a powder, spray, paste, solution, patch, drop, emulsion, suspension, aerosol, inhalant, liquid, cream, oil, lotion, ointment, gel, or solid.

8. The composition of claim 7, wherein the composition is a topical composition.

9. The composition of claim 5, wherein the composition is a capsule, cachet, pill, tablet, dragee, powder, granule, an aqueous solution, a non-aqueous solution, an aqueous suspension, a non-aqueous suspension, an oil-in-water liquid emulsion, a water-in-oil liquid emulsion, a microemulsion, an elixir, a syrup, a pastille, a bolus, an electuary or a paste.

10. The composition of claim 9, wherein the composition is an oral composition.

11. The composition of claim 9, wherein the composition is an oral, liquid dosage form.

12. The composition of claim 11, wherein the composition further comprises one or more of a wetting agent, emulsifying agent, suspending agent, sweetening agent, flavoring agent, coloring agent, perfuming agent and preservative agent.

13. A compound of the following structure:

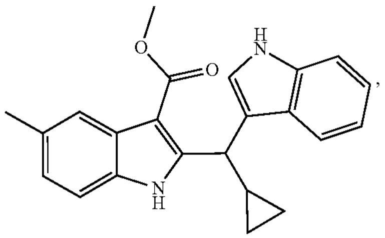 [SMILES: COC(=O)c1c(C(c2c[nH]c3ccccc23)C2CC2)[nH]c2ccc(C)cc12]

or a pharmaceutically or cosmetically acceptable salt thereof.

14. The composition of claim 4, wherein the composition further comprises one or more of a perfume, a pigment, estrogen, vitamin A, vitamin C, vitamin E, alpha-hydroxy or alpha-keto acids, lanolin, vaseline, aloe vera, methyl paraben, and propyl paraben.

15. The composition of claim 4, wherein the composition is a powder, spray, paste, solution, patch, drop, emulsion, suspension, aerosol, inhalant, liquid, cream, oil, lotion, ointment, gel, or solid.

16. The composition of claim 15, wherein the composition is a topical composition.

17. The composition of claim 4, wherein the composition is a capsule, cachet, pill, tablet, dragee, powder, granule, an aqueous solution, a non-aqueous solution, an aqueous suspension, a non-aqueous suspension, an oil-in-water liquid emulsion, a water-in-oil liquid emulsion, a microemulsion, an elixir, a syrup, a pastille, a bolus, an electuary or a paste.

18. The composition of claim 17, wherein the composition is an oral composition.

19. The composition of claim 17, wherein the composition is an oral, liquid dosage form.

20. The composition of claim 19, wherein the composition further comprises one or more of a wetting agent, emulsifying agent, suspending agent, sweetening agent, flavoring agent, coloring agent, perfuming agent and preservative agent.

21. The composition of claim 4, wherein the composition further comprises one or more of pyruvic acid, lactic acid, and glycolic acid.

22. The composition of claim 5, wherein the composition further comprises one or more of pyruvic acid, lactic acid, and glycolic acid.

* * * * *